(12) United States Patent
Le et al.

(10) Patent No.: US 10,934,162 B2
(45) Date of Patent: Mar. 2, 2021

(54) MICRORNA INITIATED DNAZYME MOTOR OPERATING IN LIVING CELLS

(71) Applicant: The Govenors of the University of Alberta, Edmonton (CA)

(72) Inventors: X. Chris Le, Edmonton (CA);
Hongquan Zhang, Ottawa (CA);
Hanyong Peng, Edmonton (CA);
Xing-Fang Li, Edmonton (CA)

(73) Assignee: THE GOVERNORS OF THE UNIVERSITY OF ALBERTA, Edmonton (CA)

(*) Notice: Subject to any disclaimer, the term of this patent is extended or adjusted under 35 U.S.C. 154(b) by 0 days.

(21) Appl. No.: 15/814,206

(22) Filed: Nov. 15, 2017

(65) Prior Publication Data

US 2018/0134549 A1 May 17, 2018

Related U.S. Application Data

(60) Provisional application No. 62/422,418, filed on Nov. 15, 2016, provisional application No. 62/422,476, filed on Nov. 15, 2016.

(51) Int. Cl.
| | |
|---|---|
| *B82Y 5/00* | (2011.01) |
| *C12N 15/113* | (2010.01) |
| *A61K 48/00* | (2006.01) |
| *C12N 15/62* | (2006.01) |

(52) U.S. Cl.
CPC .......... *B82Y 5/00* (2013.01); *A61K 48/0008* (2013.01); *C12N 15/113* (2013.01); *C12N 15/625* (2013.01); *C12N 2310/127* (2013.01); *C12N 2310/14* (2013.01); *C12N 2310/351* (2013.01); *C12N 2310/3517* (2013.01); *C12N 2310/531* (2013.01); *C12N 2320/32* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 9,725,757 B2* | 8/2017 | Bone | C12Q 21/682 |
| 2016/0083785 A1* | 3/2016 | Bone | C12Q 21/682 |
| | | | 435/6.11 |

FOREIGN PATENT DOCUMENTS

WO   WO-2013188912 A1 * 12/2013 ............. C12Q 1/682

OTHER PUBLICATIONS

Yashin, et al. (2007) J.Am.Chem.Soc., v.129, No. 50:15581-4. (Year: 2007).*
Niazov, et al. (2004) "DNAzyme-Functionalized Au Nanoparticles for the Amplified Detection of DNA or Telomerase Activity", Nano Letters, v.4, No. 9:1683-1687. (Year: 2004).*
Bath et al., "A Free Running DNA Motor Powered by a Nicking Enzyme," Angewandte Chemie International Edition, Jul. 2005, vol. 44 (28), pp. 4358-4361.
Bath et al., "DNA Nanomachines," Nature Nanotechnology, May 2007, vol. 2 (5), pp. 275-284.
Brown et al., "A Lead-Dependent DNAzyme with a Two-Step Mechanism," Biochemistry, Jun. 2003, vol. 42 (23), pp. 7152-7161.
Buxbaum et al., "In the Right Place at the Right Time: Visualizing and Understanding mRNA Localization," Nature Reviews Molecular Cell Biology, Feb. 2015, vol. 16 (2), pp. 95-109.
Cepeda-Plaza et al., "Metal ion as both a Cofactor and a Probe of Metal-Binding Sites in a Uranyl-Specific Dnazyme: A Uranyl Photocleavage Study," Nucleic Acids Research, Nov. 2013, vol. 41 (20), pp. 9361-9370.
Cha et al., "A Synthetic DNA Motor That Transports Nanoparticles Along Carbon Nanotubes," Nature Nanotechnology, Jan. 2014, vol. 9 (1), pp. 39-43.
Cha et al., "Design Principles of DNA Enzyme Based Walkers: Translocation Kinetics and Photoregulation," Journal of the American Chemical Society, Jul. 2015, vol. 137 (29), pp. 9429-9437.
Cha et al., "Optical Nanosensor Architecture for Cell Signaling Molecules Using DNA Aptamer-Coated Carbon Nanotubes," American Chemical Society nano, May 2011, vol. 5 (5), pp. 4236-4244.
Chen et al., "An Autonomous DNA Nanomotor Powered by a DNA Enzyme," Angewandte Chemie International Edition, Jul. 2004, vol. 43 (27), pp. 3554-3557.
Chen et al., "DNA Nanotechnology from the Test Tube to the Cell," Nature Nanotechnology, Sep. 2015, vol. 10 (9), pp. 748-760.
Dykman et al., "Uptake of Engineered Gold Nanoparticles into Mammalian Cells," Chemical Reviews, Jan. 2014, vol. 114 (2), pp. 1258-1288.
Giljohann et al., "Oligonucleotide Loading Determines Cellular Uptake of DNA-Modified Gold Nanoparticles," Nano letters, Dec. 2007, vol. 7 (12), pp. 3818-3821.
Gu et al., "A Proximity-Based Programmable DNA Nanoscale Assembly Line," Nature, May 2010, vol. 465 (7295), pp. 202-205.
Hancock., "Bidirectional Cargo Transport: Moving Beyond Tug of War," Nature Reviews Molecular Cell Biology, Sep. 2014, vol. 15 (9), pp. 615-628.
He et al., "Autonomous Multistep Organic Synthesis in a Single Isothermal Solution Mediated by a DNA Walker," Nature Nanotechnology, Oct. 2010, vol. 5, pp. 778-782.
Hirokawa et al., "Kinesin Superfamily Motor Proteins and Intracellular Transport," Nature Reviews Molecular Cell Biology, Oct. 2009, vol. 10 (10), pp. 682-696.
Hwang et al., "Photocaged DNAzymes as a General Method for Sensing Metal Ions in Living Cells," Angewandte Chemie International Edition, Dec. 2014, vol. 53 (50), pp. 13798-13802.
Jung et al., "A Stochastic DNA Walker that Traverses a Microparticle Surface," Nature Nanotechnology, Nov. 2015, vol. 11, pp. 157-163.
Kim et al., "Recognition-Mediated Activation of Therapeutic Gold Nanoparticles Inside Living Cells," Nature Chemistry, Nov. 2010, vol. 2 (11), pp. 962-966.

(Continued)

*Primary Examiner* — Sean McGarry
(74) *Attorney, Agent, or Firm* — Borden Ladner Gervals LLP; Mark F. Vickers

(57) ABSTRACT

There is described herein a nanomotor system and methods of use.

20 Claims, 34 Drawing Sheets

Specification includes a Sequence Listing.

(56) References Cited

OTHER PUBLICATIONS

Lim et al., "Gold Nanoparticles in Cancer Therapy," Acta pharmacologica Sinica, Aug. 2011, vol. 32 (8), pp. 983-990.
Lund et al., "Molecular Robots Guided by Prescriptive Landscapes," Nature, May 2010, vol. 465 (7295), pp. 206-210.
Ma et al., "Tumour Invasion and Metastasis Initiated by Microrna-10b in Breast Cancer," Nature, 2007, vol. 449, pp. 682-688.
Maguire et al., "Magnesium Chemistry and Biochemistry," Biometals, Sep. 2002, vol. 15 (3), pp. 203-210.
M'Hamed et al., "Identification of miR-10b, miR-26a, miR-146a and miR-153 as Potential Triple-Negative Breast Cancer Biomarkers," Cellular Oncology, Dec. 2015, vol. 38 (6), pp. 433-442.
Muscat et al., "A Programmable Molecular Robot," Nano Letters, Mar. 2011, vol. 11 (3), pp. 982-987.
Nofiele et al., "Noninvasive Manganese-Enhanced Magnetic Resonance Imaging for Early Detection of Breast Cancer Metastatic Potential," Molecular Imaging, Jan. 2014, vol. 13 (1), doi: 10.2310/7290.2013.00071.
Pan et al., "Recent Progress on DNA Based Walkers," Current Opinion in Biotechnology, Aug. 2015, vol. 34, pp. 56-64.
Rock et al., "Myosin VI is a Processive Motor With a Large Step Size," Proceedings of the National Academy of Sciences of the United States of America, Nov. 2001, vol. 98 (24), pp. 13655-13659.
Santoro et al., "Mechanism and Utility of an RNA-Cleaving DNA Enzyme," Biochemistry, Sep. 1998, vol. 37 (38), pp. 13330-13342.
Seferos et al., "Nano-Flares: Probes for Transfection and mRNA Detection in Living Cells," Journal of the American Chemical Society, Dec. 2007, vol. 129 (50), pp. 15477-15479.
Sherman et al., "A Precisely Controlled DNA Biped Walking Device," Nano Letters, 2004, vol. 4 (7), pp. 1203-1207.
Shin et al., "A Synthetic DNA Walker for Molecular Transport," Journal of the American Chemical Society, Sep. 2004, vol. 126 (35), pp. 10834-10835.
Tang et al., "The Role of MicroRNAs in Breast Cancer Migration, Invasion and Metastasis," International Journal of Molecular Sciences, Oct. 2012, vol. 13 (10), pp. 13414-13437.
Tian et al., "A DNAzyme that Walks Processively and Autonomously along a One-Dimensional Track," Angewandte Chemie (International ed. in English), Jul. 2005, vol. 44 (28), pp. 4355-4358.
Vale., "The Molecular Motor Toolbox for Intracellular Transport," Cell, Feb. 2003, vol. 112 (4), pp. 467-480.
Venkataraman et al., "An Autonomous Polymerization Motor Powered by DNA Hybridization," Nature Nanotechnology, Aug. 2007, vol. 2 (8), pp. 490-494.
Wang et al., "DNA Machines: Bipedal Walker and Stepper," Nano Letters, Jan. 2011, vol. 11 (1), pp. 304-309.
Wickham et al., "A DNA-based Molecular Motor That Can Navigate a Network of Tracks," Nature Nanotechnology, Jan. 2012, vol. 7 (3), pp. 169-173.
Wickham et al., "Direct Observation of Stepwise Movement of a Synthetic Molecular Transporter," Nature Nanotechnology, Mar. 2011, vol. 6, pp. 166-169.
Wolf et al., "Cell (Patho)Physiology of Magnesium," Clinical Science, Jan. 2008, vol. 114 (1), pp. 27-35.
Yang et al., "Enzyme-Powered Three-Dimensional DNA Nanomachine for DNA Walking, Payload Release, and Biosensing," ACS Nano, Feb. 2016, vol. 10 (2), pp. 2324-2330.
Yehl et al., "High-Speed DNA-Based Rolling Motors Powered by RNase H," Nature Nanotechnology, Feb. 2016, vol. 11 (2), pp. 184-190.
Yildiz et al., "Kinesin Walks Hand-Over-Hand," Science, Jan. 2004, vol. 303 (5658), pp. 676-678.
Yin et al., "A Unidirectional DNA Walker that moves Autonomously along a Track," Angewandte Chemie (International ed.), Sep. 2004, vol. 43 (37), pp. 4906-4911.
You et al., "An Autonomous and Controllable Light-Driven DNA Walking Device," Angewandte Chemie International Edition, Mar. 2012, vol. 51 (10), pp. 2457-2460.
Yurke et al., "A DNA-Fuelled Molecular Machine Made of DNA," Nature, Aug. 2000, vol. 406 (6796), pp. 605-608.
Zhang et al., "Binding-Induced DNA Nanomachines Triggered by Proteins and Nucleic Acids," Angewandte Chemie International Edition, Nov. 2015, vol. 54 (48), pp. 14326-14330.
Zhang et al., "Dynamic DNA Nanotechnology Using Strand-displacement Reactions," Nature Chemistry, Feb. 2011, vol. 3 (2), pp. 103-113.
Zhang et al., "Optimizing the Specificity of Nucleic Acid Hybridization," Nature Chemistry, Jan. 2012, vol. 4 (3), pp. 208-214.
Zhang et al., "Structural DNA Nanotechnology: State of the Art and Future Perspective," Journal of the American Chemical Society, Aug. 2014, vol. 136 (32), pp. 11198-11211.
Zhou et al., "A Plasmonic Nanorod That Walks on DNA Origami," Nature Communications, Aug. 2015, vol. 6, doi:10.1038/ncomms9102.
Zhou et al., "DNAzyme Hybridization, Cleavage, Degradation, and Sensing in Undiluted Human Blood Serum," Apr. 2015, vol. 87 (7), pp. 4001-4007.

* cited by examiner

MICRORNA INITIATED DNAZYME MOTOR OPERATING IN LIVING CELLS

CROSS-REFERENCE TO RELATED APPLICATIONS

This application claims priority to U.S. 62/422,418, filed Nov. 15, 2016, and U.S. 62/422,476, filed Nov. 15, 2016, the contents both of which are hereby incorporated by reference in their entirety.

FIELD

The present disclosure relates generally to a microRNA initiated DNAzyme motor operating in living cells.

BACKGROUND

Cells use protein motors to transport molecules and organelles along cytoskeleton tracks, allowing a high degree of spatial and temporal organization of cellular molecules and organelles[1-3]. Protein motors require energy to accomplish intracellular transport along specific tracks[4]. For instance, three well-known protein motors, myosin, kinesin, and dynein, use the energy from hydrolysis of ATP to perform the autonomous and processive movement along actin filaments or microtubules[5, 6].

Researchers have recently constructed various synthetic DNA motors to mimic the functions of protein motors[7-12]. The remarkable specificity and predictability of Watson-Crick base pairing make DNA an appealing construction material to build the synthetic motor systems[13-16].

Although various synthetic DNA motors have been tested in vitro, an ultimate goal of introducing them into cells to perform specific biological functions has not yet been achieved[33-35].

SUMMARY

In one aspect there is described a nanomotor system, comprising:
a support;
a substrate strand comprising a first end conjugated to said support; a second end, said second end optionally comprising a first label and/or a moiety; and a substrate portion positioned between said first end and said second end;
a motor strand comprising a first end conjugated to the support; a second end; and a catalytic core positioned between said first end and said second end; said catalytic core is switchable between an active state and an inactive state, in said active state said catalytic core is operable to cleave said substrate portion of said substrate strand; and
a locking strand comprising a first end; a second end; and a locking region positioned between said first end and said second end, said locking region adapted to removably bind to said motor strand, said locking strand optionally comprising a label and/or a moiety at said first end or said second end,
wherein when said locking strand binds to said motor strand, said catalytic core is in the inactive state,
wherein when said locking strand is absent or is displaced from said motor strand by a target, said catalytic core is in the active state.

In one example said support comprises a noble metal.
In one example said support is gold or nanoparticle gold.
In one example said support comprises a metal nanoparticle.
In one example said support comprises, silica nanoparticle or microparticle.
In one example said substrate strand comprises a nucleotide sequence.
In one example said substrate strand comprises a DNA: RNA chimeric sequence.
In one example said substrate strand comprises a DNA: RNA chimeric sequence, said substrate portion comprises a RNA nucleotide flanked by a first DNA domain and a second DNA domain.
In one example the first end of said substrate strand comprises a spacer, wherein said spacer is conjugated to said support.
In one example said spacer comprises a polynucleotide spacer.
In one example said spacer comprises a poly-thymine spacer.
In one example said spacer comprises a 14-thymine spacer.
In one example said substrate strand comprises a label and/or a moiety at said second end.
In one example said label comprises a chemiluminescent group, a chromophore, a dye, a fluorophore, a quencher, a radiolabel, metals, metal nanoparticles, colloidal metal, non-metal nanoparticle, core-shell nanoparticles, such as nanoparticles comprising a dielectric coated with metal, FAM, Cy5, biotin or tag peptides, coumarin, cyanine, benzofuran, a quinoline, a quinazolinone, an indole, a benzazole, a borapolyazaindacene and xanthenes including fluoroscein, rhodamine and rhodol as well as semiconductor nanocrystals and other fluorophores, a radioactive nuclide (e.g., 125I, 3H, 14C, 32P).
In one example the substrate strand can be hybridized to a quencher-containing and hairpin-forming further strand.
In one example said moiety comprises an anthracycline, such as doxorubicin, epirubicin, or daunorubicin, capecitabine, carboplatin, cisplatin, cyclophosphamide, eribulin, fluorouracil, gemcitabine, ixabepilone, methotrexate, mitoxantrone, mutamycin, a taxane such as paclitaxel, and docetaxel (Taxotere), thiotepa, vincristine, and vinorelbine, trastuzumab, lapatinib, bevacizumab, pertuzumab and everolimus, selective estrogen receptor modulators (SERMs), such as tamoxifen, raloxifene, endoxifene, toremifene, lasofoxifene, pipendoxifene, bazedoxifene, and ospemifene, aromatase inhibitors, such anastrozole, letrozole, exemestane, formestane, fadrozole, aminoglutethimide, and testolactone, a HER2 intervention drug, such as a HER2 inhibitor, such as Herceptin, pertuzumab, and lapatinib, and estrogen-receptor downregulators, such as fulvestrant, and combinations thereof.
In one example said catalytic core comprises a DNAzyme.
In one example said DNAzyme is a truncated form of 8 17E DNAzyme.
In one example said first end of said motor strand comprises a spacer, wherein said spacer is conjugated to said support.
In one example said spacer comprises a polynucleotide spacer.
In one example said spacer comprises a poly-thymine spacer.
In one example said spacer comprises a 42-thymine spacer.
In one example said motor strand comprises a locking region adjacent said spacer, said locking region comprising a first domain (T*1) and a first arm (Arm2); and a second arm (Arm1), said catalytic core positioned between said first arm and said second arm.

In one example said locking region on said locking strand comprises a target binding domain and a sequestering domain, wherein said target binding domain comprises a sequence which removable binds to said target sequence, wherein said sequestering domain comprises a sequence which removable binds to said first arm of said motor strand.

In one example said locking region on said locking strand comprises a target binding domain and a sequestering domain, wherein said target binding domain comprises a sequence which is complementary to said target sequence, wherein said sequestering domain comprises a sequence complementary to said first arm of said motor strand.

In one example there is a plurality of said substrate strands and a plurality of said motor strands on said support.

In one example there is a plurality of said substrate strands and a plurality of said motor strands on said support, and wherein there are more of said substrate strands than said motor strands.

In one aspect there is described a method for treating a subject having, or suspected of having, cancer, comprising: administering a nanomotor system according to any preceding claim.

In one example said cancer is breast cancer.

In one example there is described a use of a nanomotor system according to any preceding claim for treating a subject having, or suspected of having, a cancer.

In one aspect there is described a use of a nanomotor system according to any preceding claim for the manufacture of a medicament for treating a subject having, or suspected of having, a cancer.

In one example said cancer is breast cancer.

In one aspect there is described a method of detecting a target in a sample, comprising: contacting a said sample with a nanomotor system according to any preceding claim.

In one example said target is a small molecule, a protein, nucleic acid (DNA or RNA), including mRNA, miRNA, and DNA, microRNA, miR-10b, an analyte or analyte of interest, a metabolite, an amino acid, a herbicide, a pesticide, an environmental pollutant, an analyte, a veterinary drug, a drug, a drug of abuse, an antigen, a receptor, a receptor ligand, or a peptide, a lipoprotein, a glycoprotein, a ribo- or deoxyribonucleoprotein, a polysaccharide, a lipopolysaccharide, a lipid, a fatty acid, a vitamin, a pharmaceutical compound (e.g., tranquilizers, barbiturates, opiates, alcohols, tricyclic antidepressants, benzodiazepines, anti-virals, anti-fungals, steroids, cardiac glycosides, or a metabolite of any of the preceding), a hormone, a growth factor, an enzyme, a coenzyme, an apoenzyme, haptens, lechtins, a substrate, a cellular metabolite, a cellular component or organelle (e.g., a membrane, a cell wall, a ribosome, a chromosome, a mitochondria, or a cytoskeleton component).

In one aspect there is described a kit comprising a nanomotor system of any preceding claims, and instructions for use.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

a substrate strand comprising a first end conjugated to said support; a second end, said second end optionally comprising a first label and/or a moiety; and a substrate portion positioned between said first end and said second end;

a motor strand comprising a first end conjugated to the support; a second end; and a catalytic core positioned between said first end and said second end; said catalytic core is switchable between an active state and an inactive state, in said active state said catalytic core cleaves said substrate portion of said substrate; and a locking strand comprising a first end; a second end; and a locking region positioned between said first end and said second end, said locking region adapted to removably bind to said motor strand, said locking strand optionally comprising a label and/or a moiety at said first end or said second end, wherein when said locking strand binds to said motor strand, said catalytic core is in the inactive position, wherein when said locking strand is absent or is displaced from said motor strand by a target, said catalytic core is in the active position.

It will be appreciated that the kit may comprise one or more of the individual components, namely: a support a substrate strand comprising a first end which may be conjugated to said support; a second end, said second end optionally comprising a first label and/or a moiety; and a substrate portion positioned between said first end and said second end; a motor strand comprising a first end which may be conjugated to the support; a second end; and a catalytic core positioned between said first end and said second end; said catalytic core is switchable between an active state and an inactive state, in said active state said catalytic core cleaves said substrate portion of said substrate; and a locking strand comprising a first end; a second end; and a locking region positioned between said first end and said second end, said locking region adapted to removably bind to said motor strand, said locking strand optionally comprising a label and/or a moiety at said first end or said second end.

To gain a better understanding of the invention described herein, the following examples are set forth. It should be understood that these examples are for illustrative purposes only. Therefore, they should not limit the scope of this invention in anyway.

Figure 15:
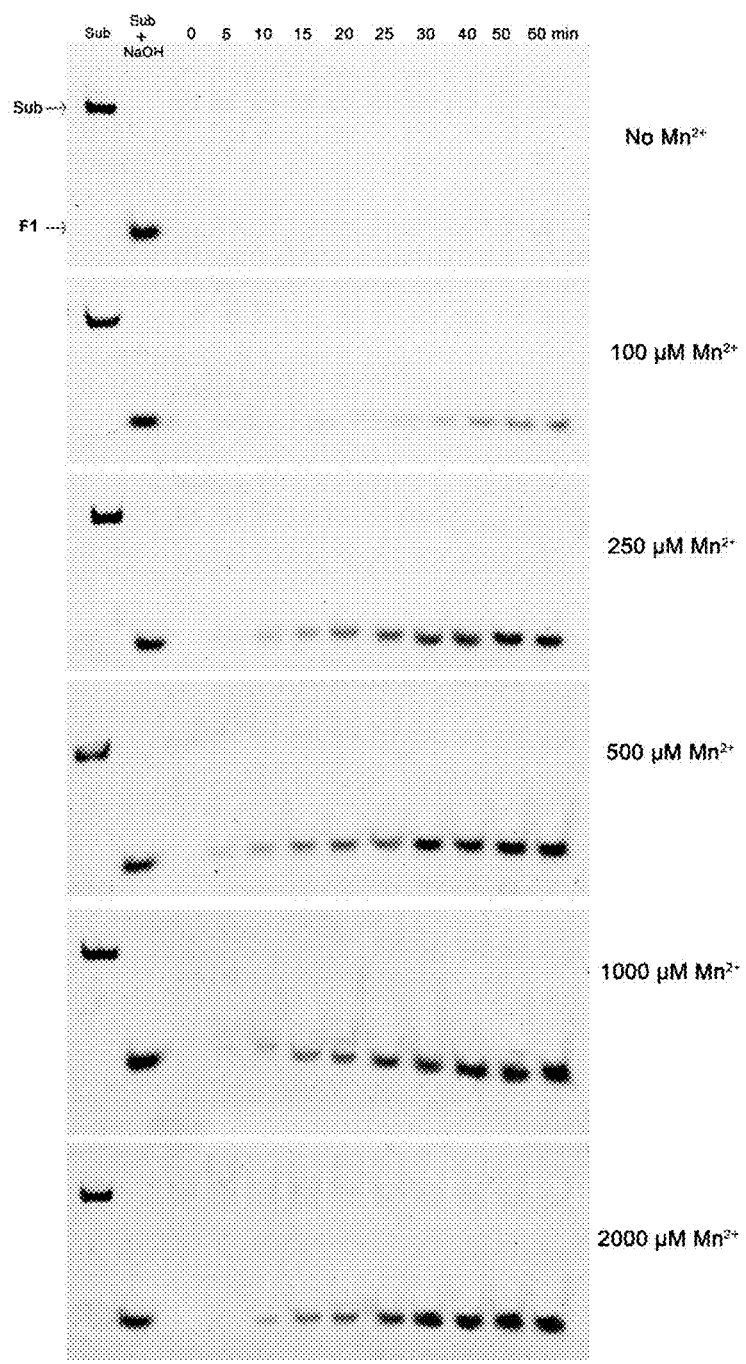

FIG. 15 depicts gel images showing no cleavage of the fluorescent substrate by a mutated DNAzyme motor (top gel) and the various amounts of the fluorescent substrate fragment (F1) cleaved by the DNAzyme motor in the presence of different concentrations of the cofactor Mn2+. The DNAzyme or mutated DNAzyme motor system at a concentration equivalent to 7 nM AuNPs was mixed with 16 nM target DNA sequence in autoclaved buffer (pH 8.0) containing 25 mM Tris-acetate and 200 mM NaCl. After incubation at room temperature for 20 min, 0, 100, 250, 500, 1000, or 2000 µM $Mn^{2+}$ was added to initiate the catalytic cleavage of the substrate. From 0 min to 60 min after the addition of $Mn^{2+}$, 5 µL of the reaction solution was repeatedly sampled, to which 5 µL of 50 mM EDTA was added to chelate the cofactor $Mn^{2+}$ and thus stop the catalytic reaction. The reaction solution was analyzed by gel electrophoresis. The far left lane is from the FAM-substrate in the autoclaved buffer. No cleavage product is detectable, suggesting that the substrate is stable in the autoclaved buffer. The second lane from left is the control showing the fluorescent substrate fragment (F1) obtained by hydrolysis of the ribonucleotide bond of the substrate using 2M NaOH.

Figure 3:
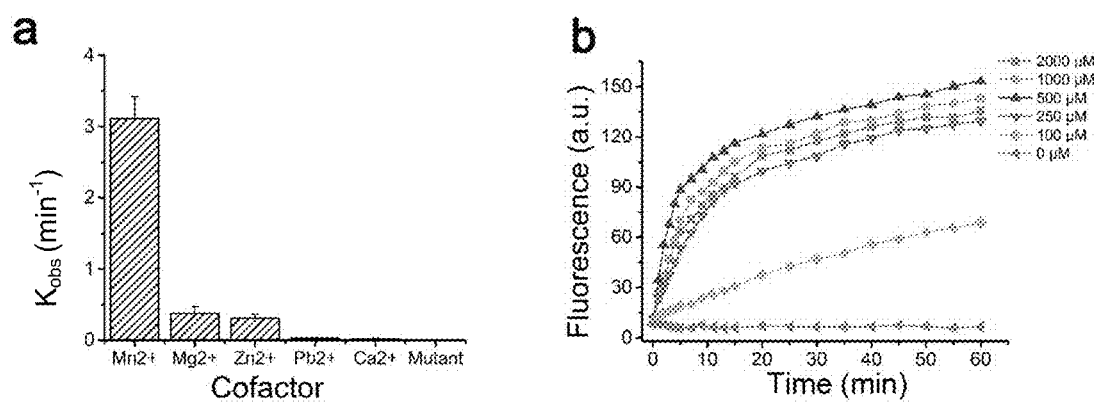
FIG. 3 depicts effect of the cofactors on the operation of the DNAzyme motor. (Panel a) Multiple-turnover cleavage rate ($K_{obs}$) of the DNAzyme motor tested using 200 pM target DNA and different divalent metal ions as cofactors. The concentrations of metal ions were 0.5 mM $Mn^{2+}$, 10 mM $Mg^{2+}$ and $Ca^{2+}$, 0.01 mM $Zn^{2+}$, and 0.2 mM $Pb^{2+}$. A mutant DNAzyme motor (sequence in Table 1) was also tested using 200 pM target DNA and 0.5 mM $Mn^{2+}$. (Panel b) Real-time fluorescence generated by the DNAzyme motor that was initiated by 200 pM target DNA and activated by different concentrations of the cofactor $Mn^{2+}$. The relative standard deviations from replicate experiments were 2.4-6.6%.
Figure 16:
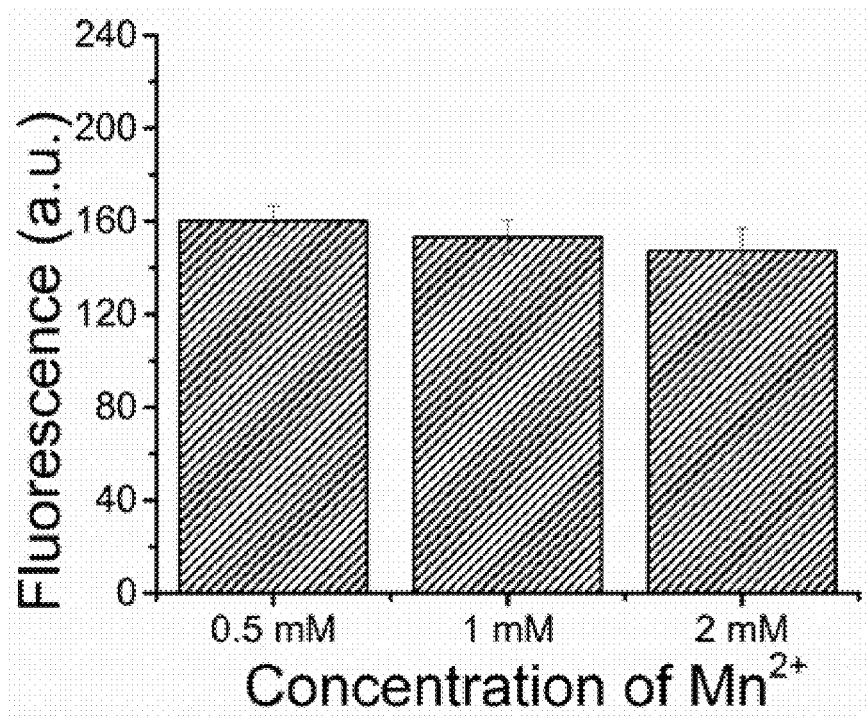

FIG. 16 depicts the effect of $Mn^{2+}$ concentration on the fluorescence intensity of FAM-labeled substrate. The concentration of the FAM-labeled substrate is 10 nM. In a comparison of the fluorescence generated by the DNAzyme motor that was initiated by 200 pM target DNA and activated by different concentrations of the cofactor $Mn^{2+}$ (FIG. 3b), The fluorescence intensity from the use of 1 mM and 2 mM of $Mn^{2+}$ was slightly lower than that from the use of 0.5 mM $Mn^{2+}$ (FIG. 3b). The slightly lower fluorescence intensity of the cleaved fluorescent substrate (F1) is probably because of a combination of the following: (i) the higher $Mn^{2+}$ concentration decreased the cleavage rate (Fig. S7) by slowing down the dissociation of DNAzyme from the cleavage product F2; and (ii) a reduced fluorescence intensity of F1 due to fluorescence quenching (Fig. S8).

Figure 17:
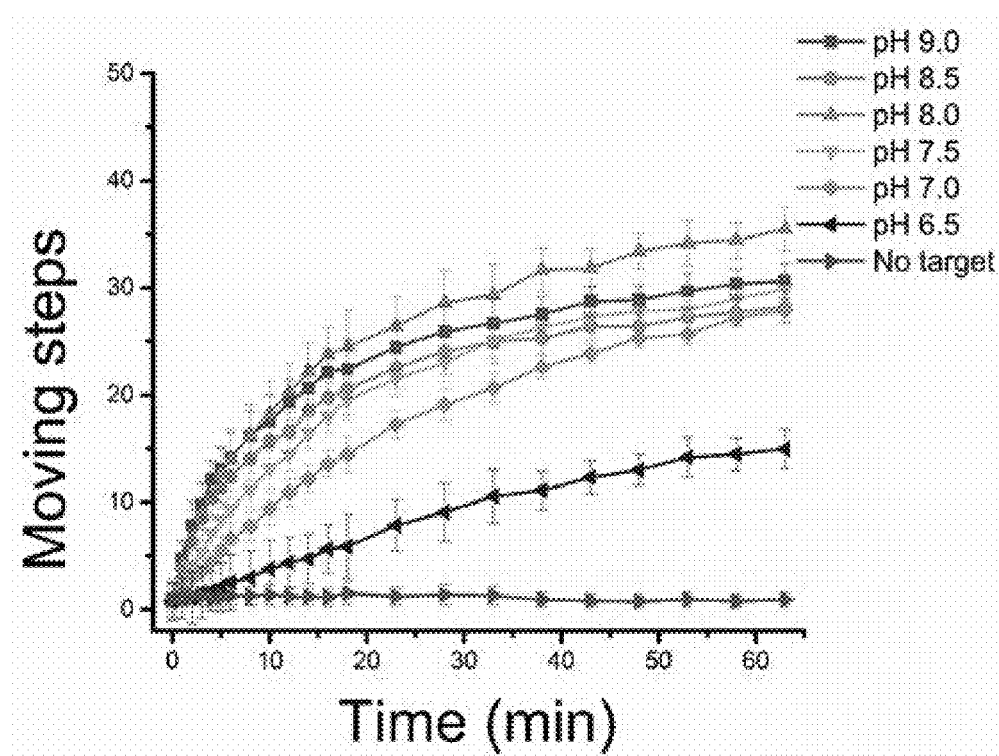

FIG. 17 depicts operating curves of the DNAzyme motor under different pH conditions. The concentration of $Mn^{2+}$ is 500 µM, and the concentration of the DNA target is 200 pM (or 0 pM for the control). Note that at higher pH (e.g., >8.5), $Mn^{2+}$ could precipitate as $Mn(OH)_2$, according to $K_{sp}$ of $Mn(OH)_2$ which is $1.9 \times 10^{-13}$.

Figure 18:
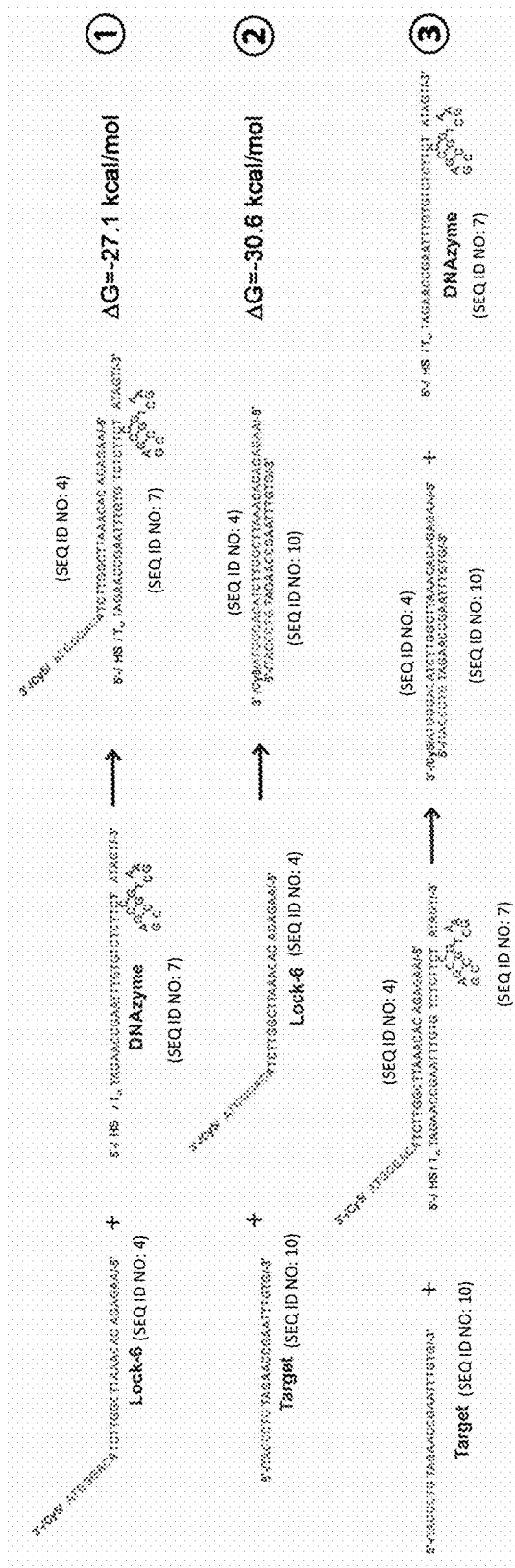

FIG. 18 depicts schematics showing the pertinent hybridization reactions. CD ① Hybridization between Lock-6 and DNAzyme strand; ② Hybridization reaction between Lock-6 and target DNA; ③ Toehold-mediated strand exchange reaction between the target DNA and the duplex of Lock-6 and DNAzyme strand.

Figure 19:
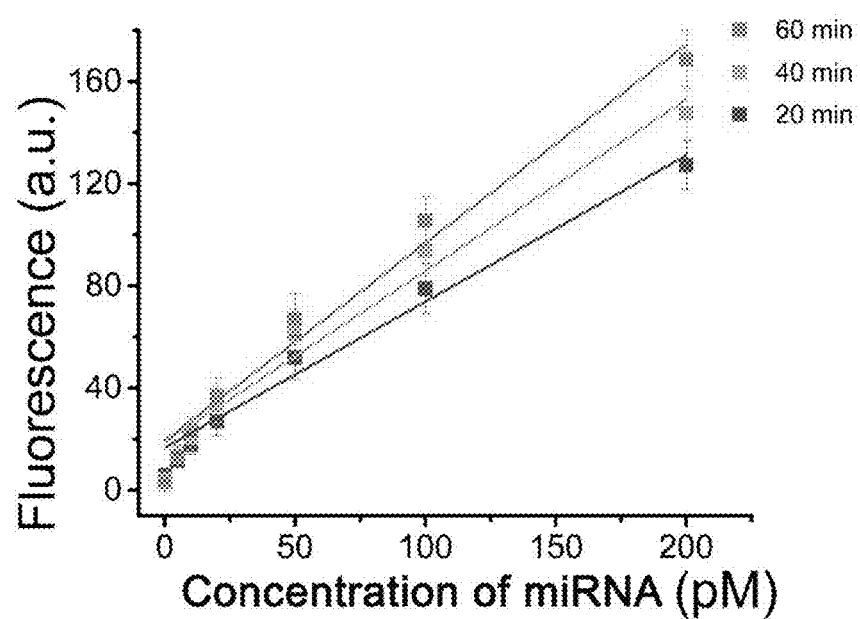

FIG. 19 depicts intensity of fluorescence generated by the DNAzyme motor in response to various concentrations of the target miRNA. The fluorescence intensity (arbitrary unit) was measured at 20, 40, and 60 min after the activation by the cofactor $Mn^{2+}$.

Figure 20:
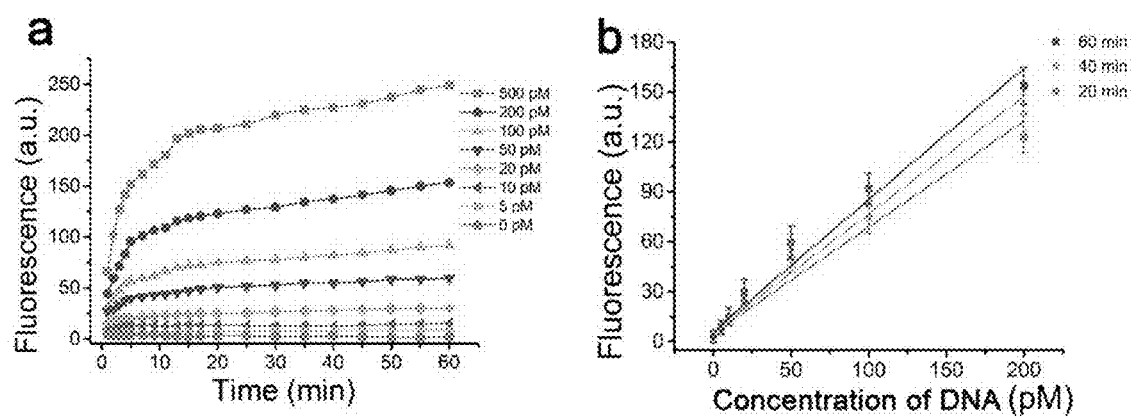

FIG. 20 depicts intensity of fluorescence generated by the DNAzyme motor in response to varying concentrations (0-500 pM) of the target DNA. Duplicate experiments were carried out for all tests and relative standard deviations (RSDs) were in the range of 2.7-8.6%. (Panel a) Real-time monitoring of fluorescence generated by the DNAzyme motor in response to varying concentrations (0-500 pM) of the target DNA. Time 0 refers to when the cofactor $Mn^{2+}$ was added to activate the motor. (Panel b) Relationships between the concentration of the target DNA and fluorescence intensity (arbitrary unit) measured at 20, 40, and 60 min after the addition of the cofactor $Mn^{2+}$.

Figure 21:
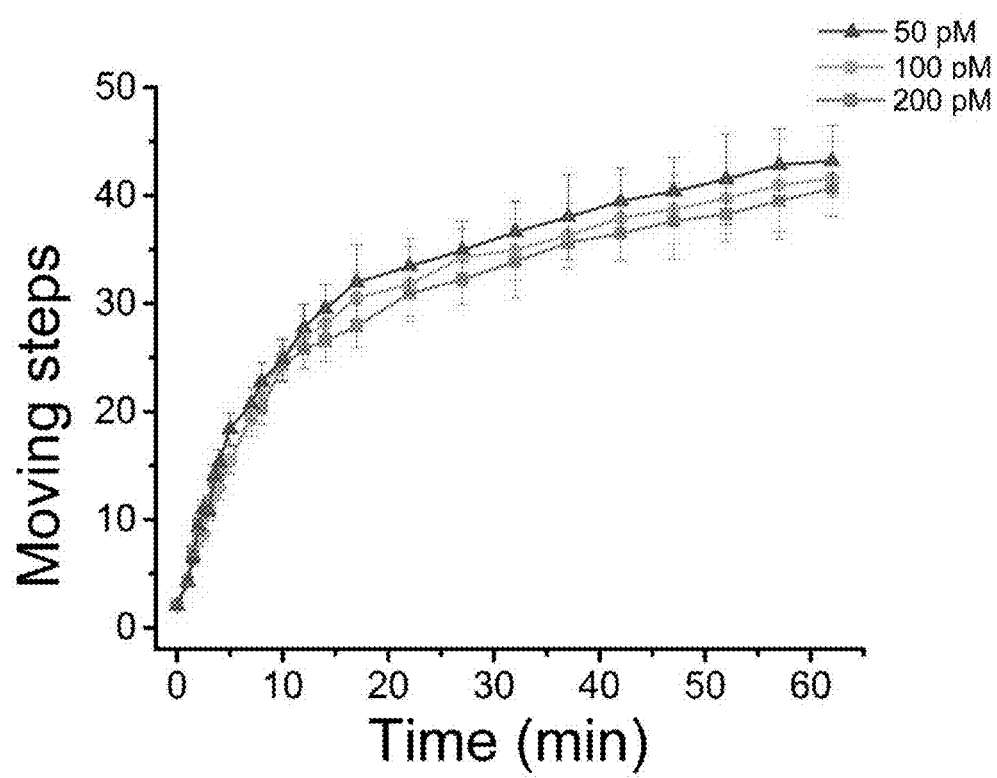

FIG. 21 depicts moving steps of DNAzyme motors, initiated by 50, 100, and 200 pM target miRNA. The moving steps were estimated from measuring the fluorescence of the cleaved fluorescent substrate (F1). The concentration of the cleaved fluorescent substrate fragment (F1) was determined against a calibration curve that was constructed by using standard solutions of FAM-labeled substrate. For example, from the calibration, the concentration of the cleaved fluorescent substrate fragment (F1) after 27 min of the motor operation was determined to be 6.2 nM. This was initiated by 200 pM target miRNA. Because the concentration of miRNA is lower than that of the DNAzyme motor, each target miRNA molecule activates a single DNAzyme motor. Each walking step of the motor generates a substrate fragment (F1). Therefore, the detected overall 6.2 nM substrate fragment (F1) is a result of 31 average walking steps of each DNAzyme motor initiated by 200 pM (0.2 nM) target miRNA (6.2 nM/0.2 nM=31).

Figure 22:
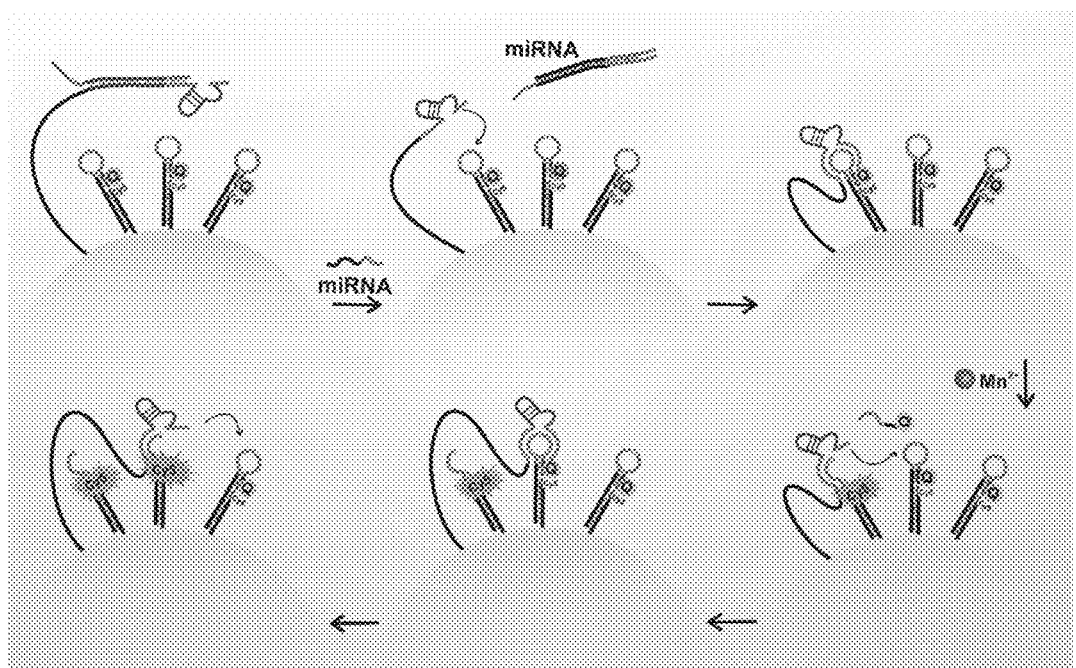

FIG. 22 depicts a schematic showing the operation of the DNAzyme motor designed to trace the walking of the DNAzyme motor on individual AuNPs. The substrate strand is designed to enable each walking step of the motor to turn on the fluorescence of a Cy5 molecule on the AuNP. The substrate strand contains a hairpin structure with a long single-stranded overhang at 5'-end that hybridizes to a Cy5-labeled DNA strand. The 3'-end of the substrate strand is labeled with a black hole quencher so that hybridization of the substrate strand to the Cy5-labeled strand quenches the fluorescence of Cy5 by the quencher in close proximity. The motor system is constructed by conjugating each AuNPs with dozens of locked DNAzyme strands and hundreds of hybrids between the hairpin substrate and the Cy5-labeled strands. 50-nm AuNPs are used to construct the motor system for practical detection by total internal reflection fluorescence microscopy (TIRFM). In the presence of the target miRNA sequence, the locked DNAzyme is activated to cleave the substrate at the single-ribonucleotide junction in the hairpin loop. The cleavage disrupts the hairpin structure and releases a quencher-containing fragment from the AuNP, restoring the fluorescence of the Cy5 molecule. The DNAzyme dissociates from the cleaved substrate and hybridizes to the next substrate strand, enabling the walking of the DNAzyme motor from one substrate strand to the next. Each walking step restores the fluorescence of one Cy5 molecule that is attached onto the AuNP through a double-stranded DNA between the substrate overhang and the Cy5-labeled strand. Quenching of Cy5 fluorescence by AuNP is moderate because of the double-stranded DNA between Cy5 and AuNP. The estimated distance from Cy5 to the surface of the AuNP is about 11 nm (32 bp). Therefore, operation of the DNAzyme motor on individual AuNPs can be traced by measuring fluorescence increase of each AuNP.

Figure 23:
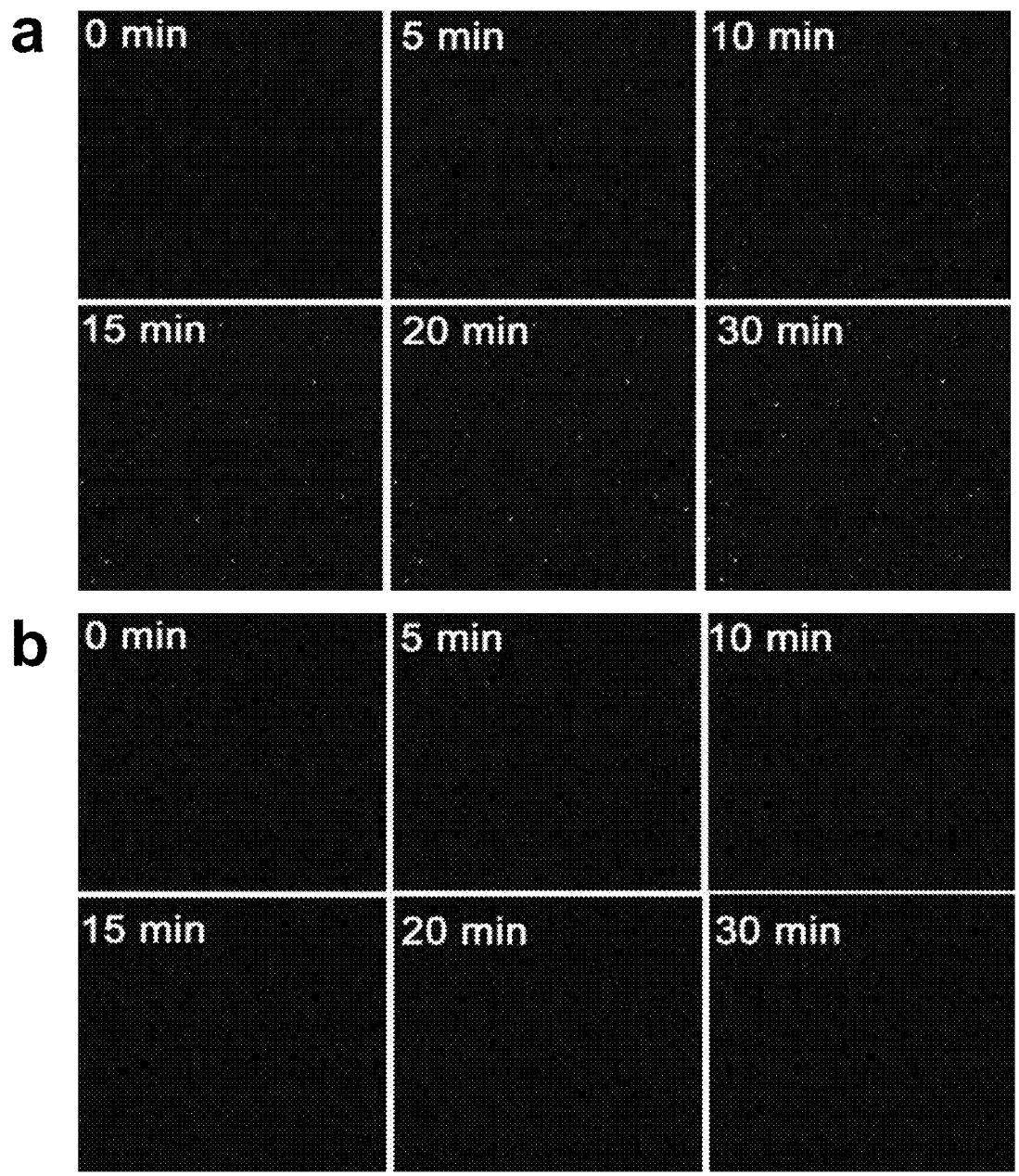

FIG. 23 depicts fluorescence images showing operation of the DNAzyme motor on individual AuNPs in the presence (Panel a) or absence (Panel b) of target miRNA sequence. The frames were extracted from a video. The white dots on black background in (a) are due to fluorescent Cy5 on the AuNPs as depicted in FIG. 22. Forty five microliters of the operating solutions contained either 300 pM target miRNA (a) or no target miRNA (b), the DNAzyme motor (FIG. 22) at an equivalent concentration of 30 pM functionalized AuNP, 25 mM Tris-acetate buffer (pH 8.0), and 200 mM NaCl. After incubation at room temperature for 20 min, 0.5 mM $MnCl_2$ solution was added to initiate the operation of the motor. The time 0 min in the figure refers to when the $MnCl_2$ was added. One µL of the incubation mixture was transferred onto a microscope slide (25×76×1.0 mm, Fisherbrand). A micro coverglass (diameter: 18 mm, thickness: 0.16-0.19 mm; Electron Microscopy Sciences) was placed over the solution on top of the slide. The AuNPs sandwiched between the microscope slide and the coverglass were then imaged using a DeltaVision OMX Imaging System (GE Healthcare Life Sciences). A 60×/1.49 TIRF objective (Nikon) was used, and a 647-nm laser provided excitation. 120 frames were acquired in 30 min with 10% laser power and 100 ms exposure time for each frame.

Figure 24:
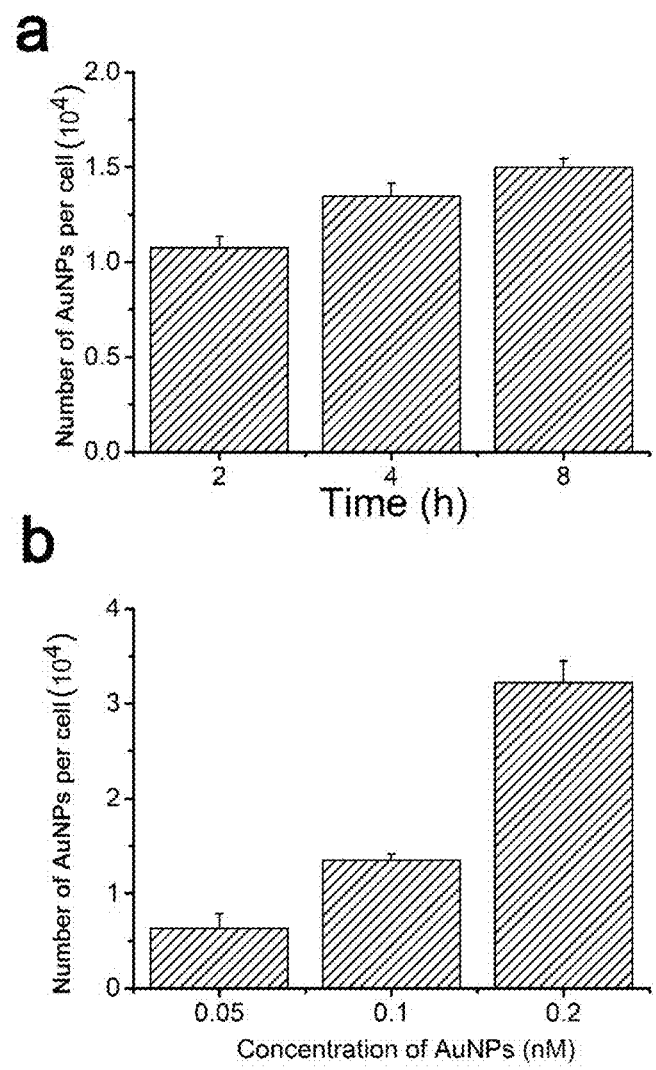

FIG. 24 depicts uptake of DNAzyme motor system into MDA-MB-231 cells as measured by the concentrations of Au in the cells. (Panel a) Effect of the incubation time. (Panel b) Effect of incubation concentration of AuNPs on which the DNAzyme motor system is constructed. Error bars represent one standard deviation from triplicate experiments.

Figure 25:
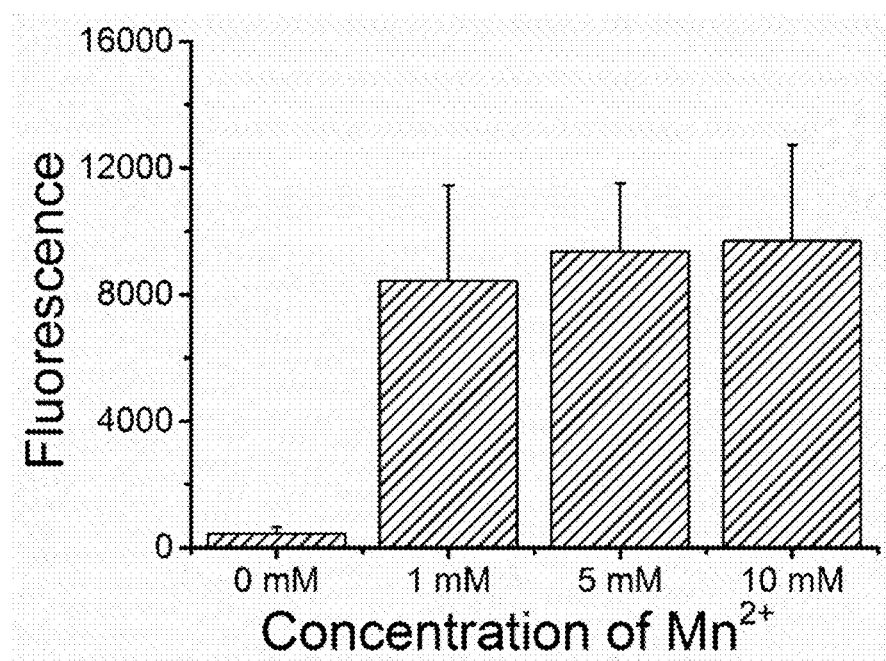

FIG. 25 depicts the effect of treatment concentration of $Mn^{2+}$ on the intracellular operation of the DNAzyme motor. Fluorescence intensity was determined from fluorescence images of cells 60 min after the addition of $Mn^{2+}$. Fluorescence measurement was carried out using ImageJ 1.47. Error bars represent one standard deviation from triplicate experiments.

Figure 26:
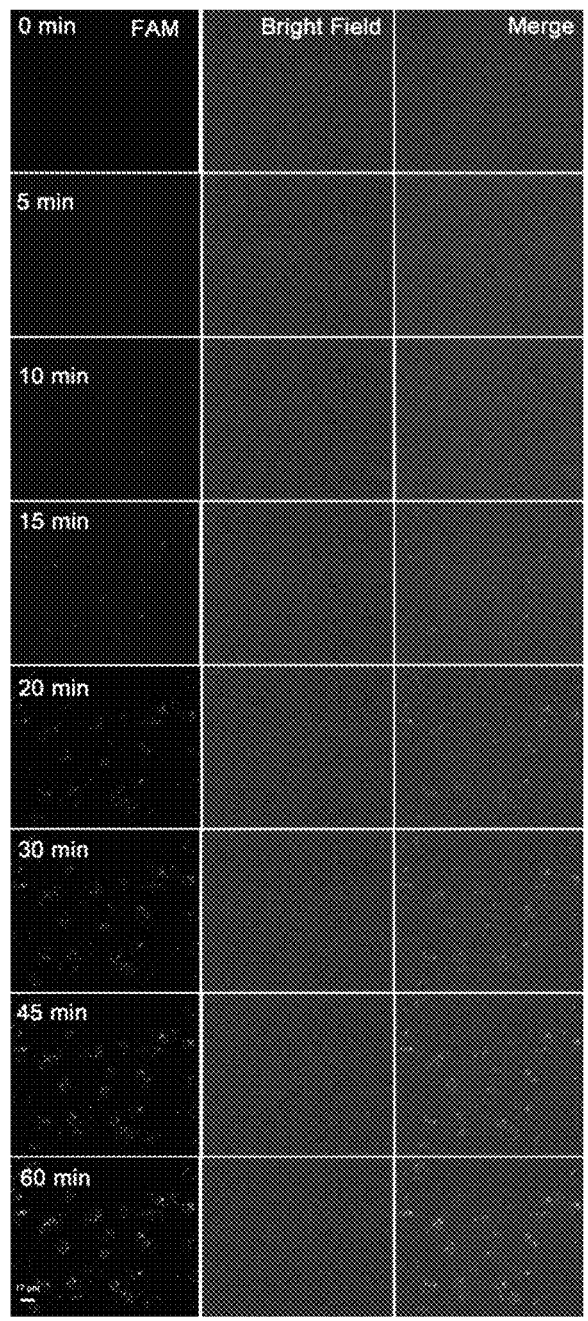

FIG. 26 depicts images of MDA-MB-231 cancer cells following intracellular operation of the DNAzyme motor. MDA-MB-231 cancer cells were incubated with the DNAzyme motor for 2 h. The cells were washed and then $Mn^{2+}$ and the operating buffer were added. Immediately after the addition of $Mn^{2+}$, fluorescence images of the cells were repeatedly acquired for 60 min at a rate of 2 frames per min. The observed fluorescence in the cells is a result of intracellular operation of the DNAzyme motor initialed by the target microRNA (miR-10b) in the cells and activated by the cofactor $Mn^{2+}$. An Olympus IX-81 fluorescence microscope coupled with a Yokagawa CSU×1 spinning disk confocal scan-head was used. LMM5 laser transmission setting was 20 and the laser excitation time was 495 ms for each frame of the fluorescence images.

Figure 27:
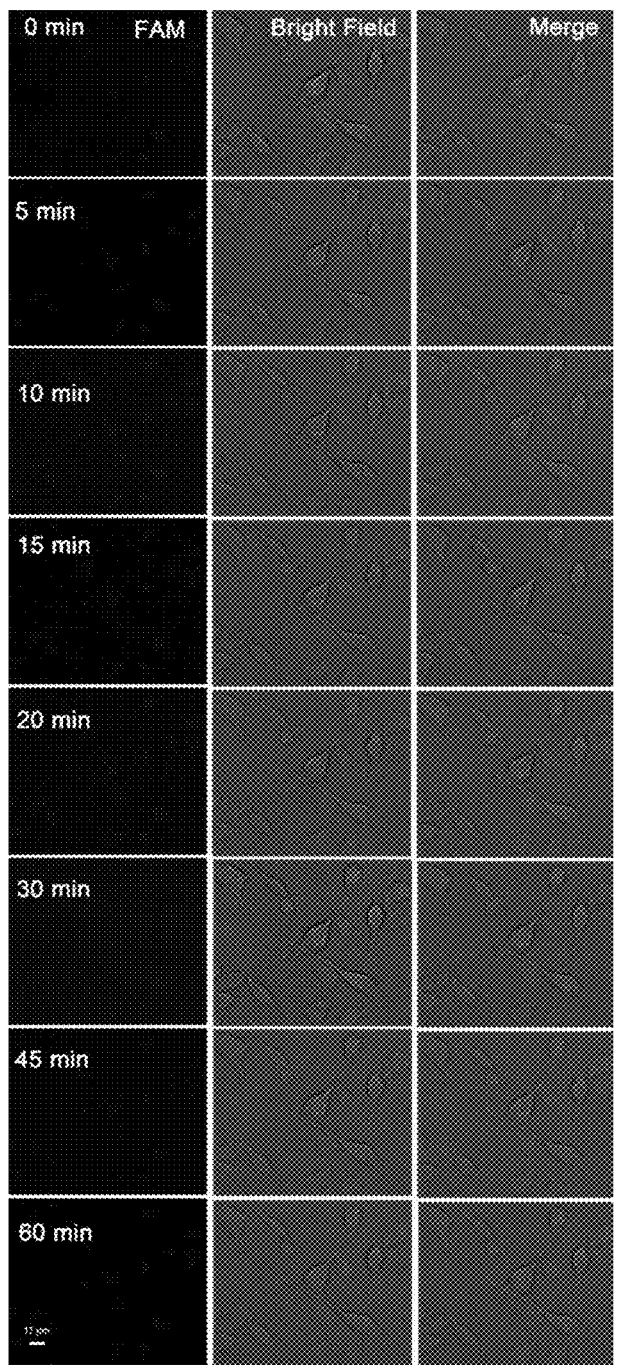

FIG. 27 depicts images of MDA-MB-231 cancer cells after incubation with the mutant DNAzyme motor for 2 h followed by the addition of $Mn^{2+}$ and fluorescence imaging at 0, 5, 10, 15, 20, 30, 45, and 60 min after the addition of $Mn^{2+}$. No fluorescence is observed from the cells, indicating that the mutant DNAzyme motor is inactive in the cells. Same conditions of microscopy as shown in Fig. S18 were used.

Figure 28A:
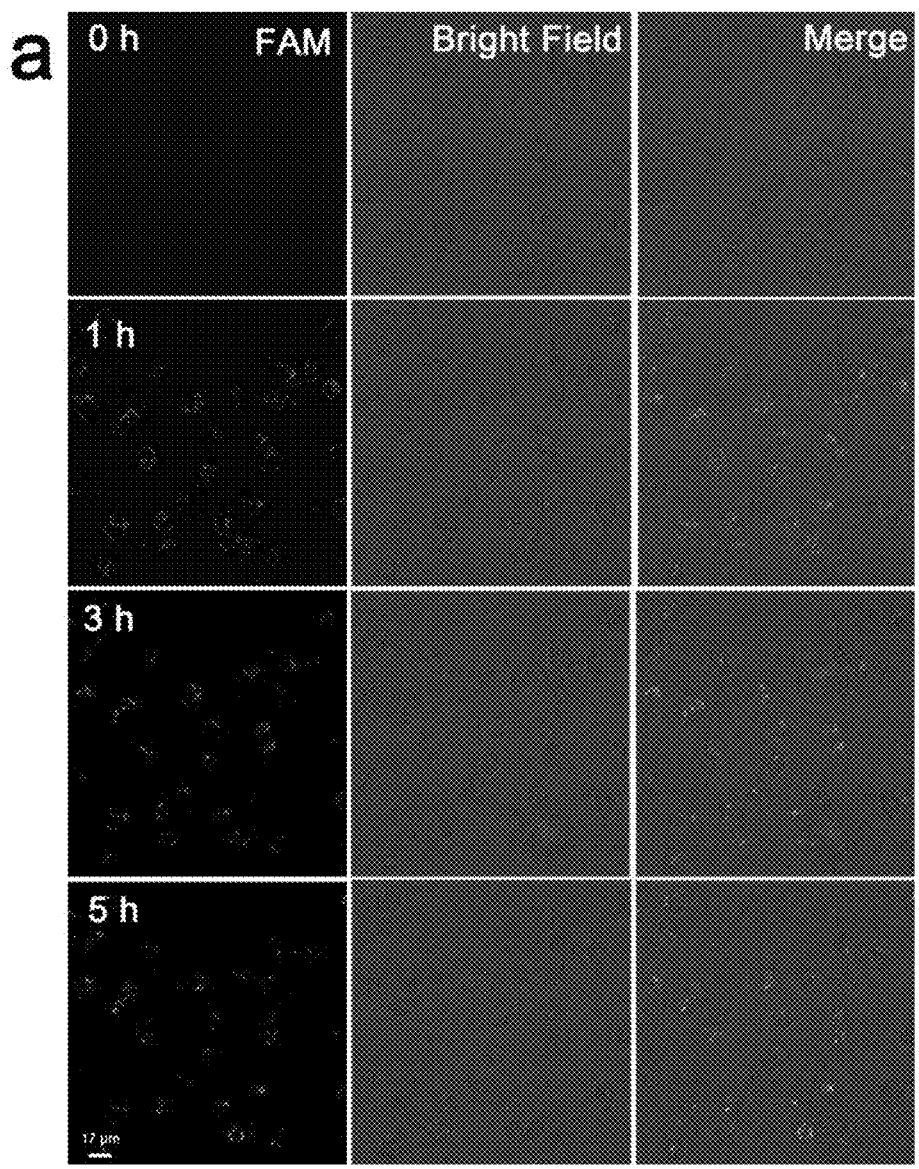

FIG. 28a depicts images of MDA-MB-231 cancer cells after intracellular operation of the DNAzyme motor for 0, 1, 3, and 5 hours. MDA-MB-231 cancer cells were incubated with the DNAzyme motor for 2 h. The cells were washed and then $Mn^{2+}$ in the operating buffer was added. Immediately after the addition of $Mn^{2+}$, fluorescence images of the cells were repeatedly acquired over the 5-h period. The observed fluorescence in the cells is a result of intracellular operation of the DNAzyme motor initialed by the target microRNA (miR-10b) in the cells and activate by the cofactor $Mn^{2+}$. The slight decrease of fluorescence intensity observed after 5 h is probably due to photo bleaching of the fluorescent substrate.

Figure 28B:
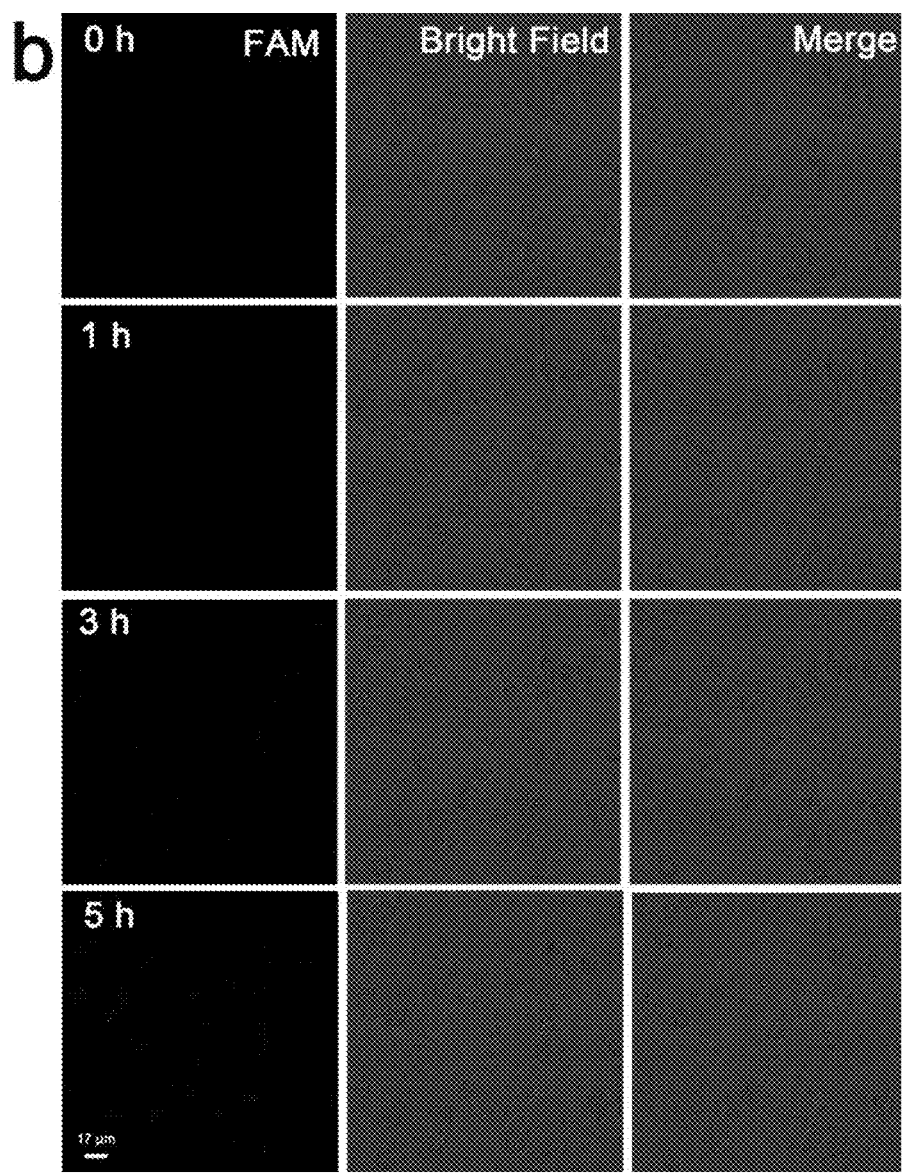

FIG. 28b depicts images of MDA-MB-231 cancer cells after incubation with the mutant DNAzyme motor for 2 h followed by the addition of $Mn^{2+}$ and fluorescence imaging at 0, 1, 3, and 5 h after the addition of $Mn^{2+}$. No fluorescence is detectable from the cells, indicating that the substrate strands on AuNPs are stable in the cells.

Figure 29:
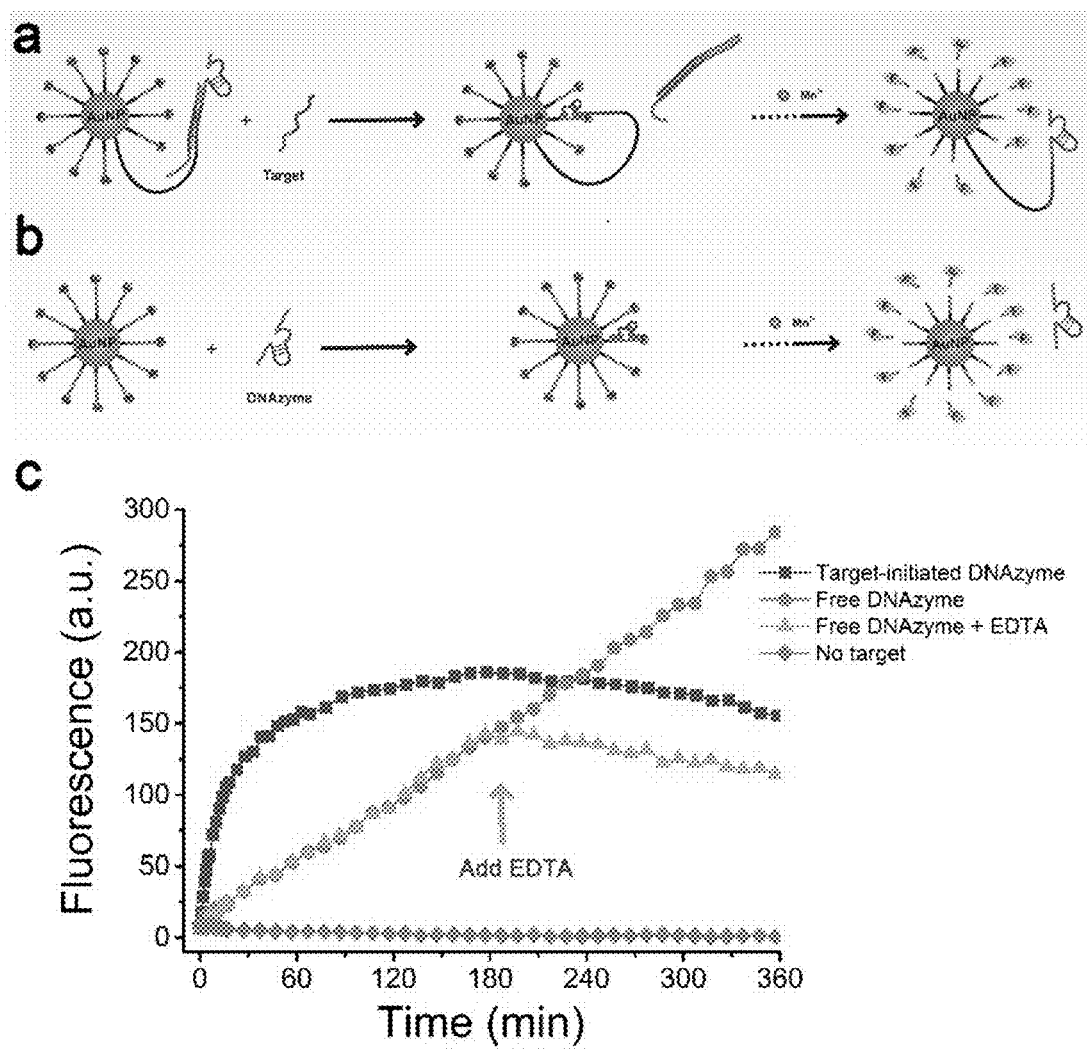

FIG. 29 depicts a comparison of walking and results of catalytic cleavage of the substrate by the miRNA target-initiated DNAzyme motor and by the free control DNAzyme that is not conjugated to AuNP. (Panel a) Scheme showing the operation of target-initiated DNAzyme motor. (Panel b) Scheme showing the operation of the free control DNAzyme. The free control DNAzyme sequence (Table 1) has an 8-nt Arm 1 and an 8-nt Arm 2 to assist its hybridization to the substrate. (Panel c) The operating curves of the target-initiated and the free DNAzyme motors. The operation of motors was monitored for 6 h following the addition of cofactor $Mn^{2+}$. Relative standard deviations from replicate measures were in the range of 1-5%. The small decrease of fluorescence from the target-initiated DNAzyme motor after 3 h is probably due to photo bleaching by extended period of excitation light. Support for this is from the following experiment. 3 h after the operation of the free control DNAzyme, EDTA was added to the solution to chelate the cofactor $Mn^{2+}$ and thus stop the further operation of the DNAzyme. Continued monitoring of the fluorescent substrate fragment produced during the first 3 h by the free DNAzyme shows the same slight decreasing pattern as in the case of the target-initiated DNAzyme motor.

Figure 30:
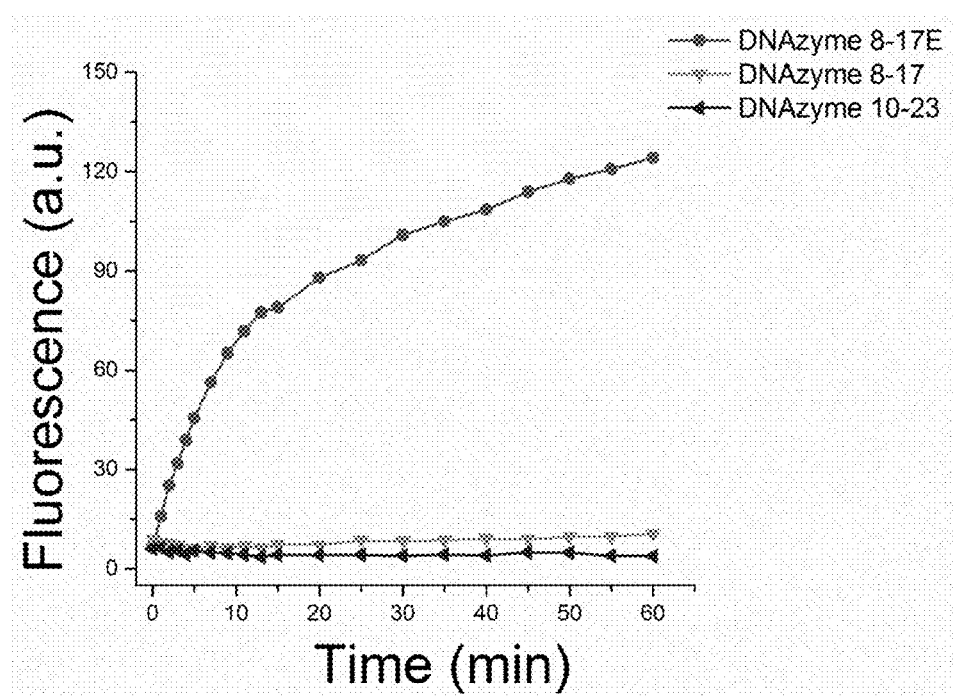

FIG. 30 depicts a comparison of the operation of the motors constructed with three different DNAzymes, 10-23, 8-17, and 8-17E. These DNAzymes were biotin-labeled and their sequences are shown in Table S1. AuNPs were conjugated with hundreds of substrate strands and dozens of biotin-labeled poly thymine (30 T). Streptavidin was then used to link the biotin-labeled DNAzyme onto the AuNPs. Specifically, operation solutions were prepared to contain 230 pM AuNPs, 200 pM streptavidin, 2 nM biotin-labeled DNAzyme strand in 25 mM Tris-acetate (8.0) and 200 mM NaCl. After incubation at room temperature for 20 min, 500 µM $Mn^{2+}$ was then added to the solutions to activate the operation of the motors. The fluorescence of the solutions was then monitored in real-time for 60 min. Relative standard deviations from replicate measures were in the range of 2.2-6.4%.

Figure 31:
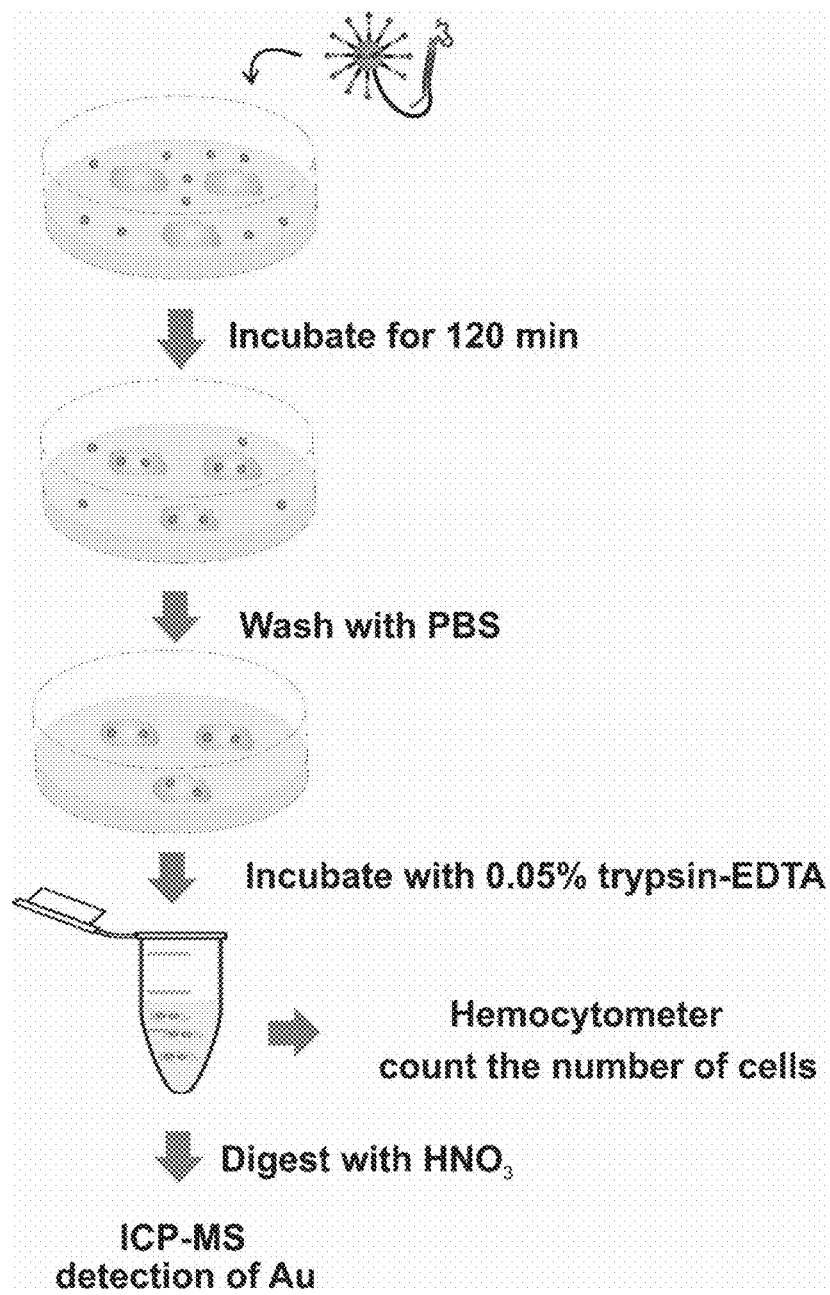

FIG. 31 depicts a schematic showing the experiments conducted to determine cellular uptake of the DNAzyme motor system. The DNAzyme motor system consists of AuNPs functionalized with the substrate and the locked DNAzyme sequences.

Figure 32:
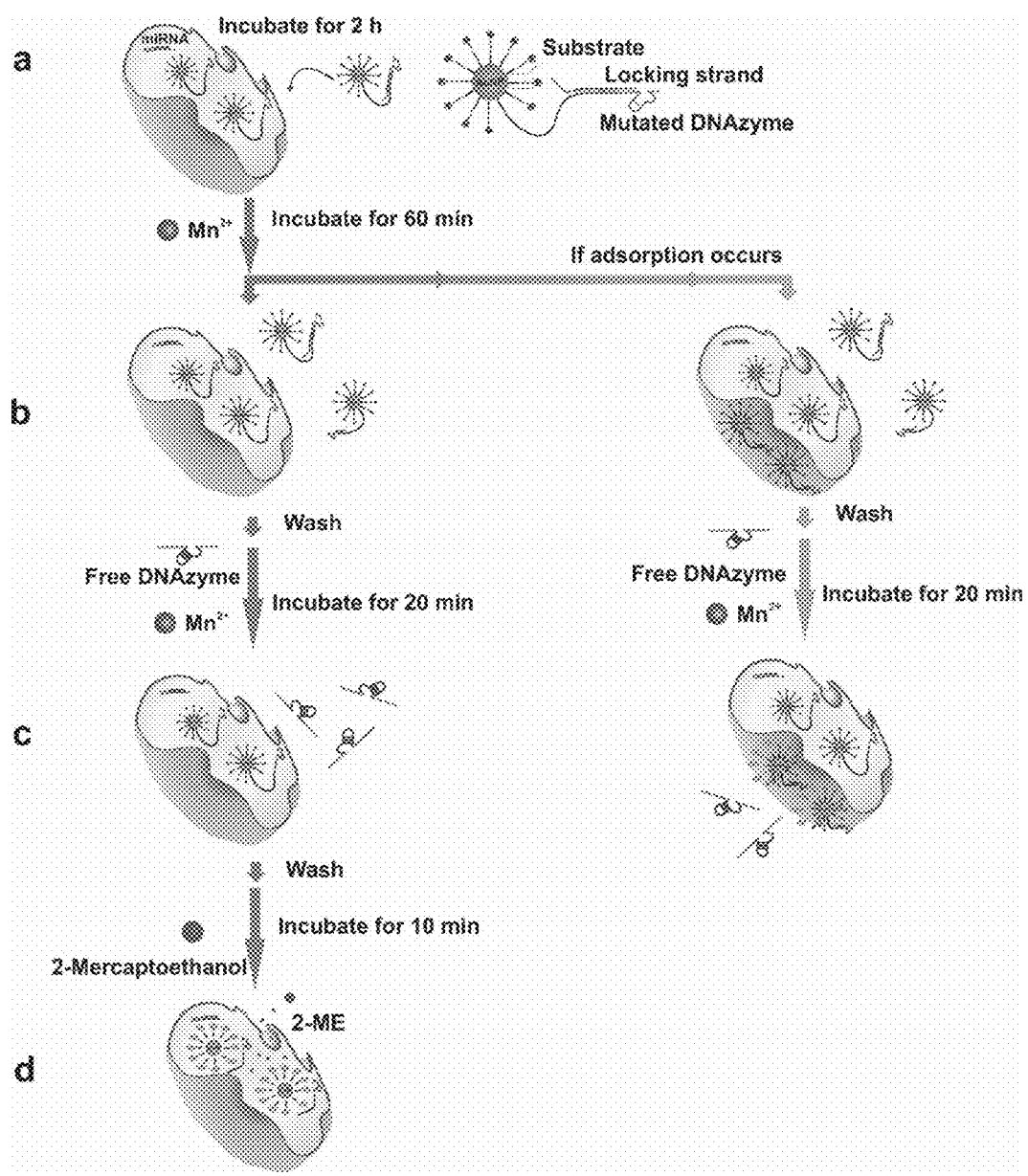
Figure 33:
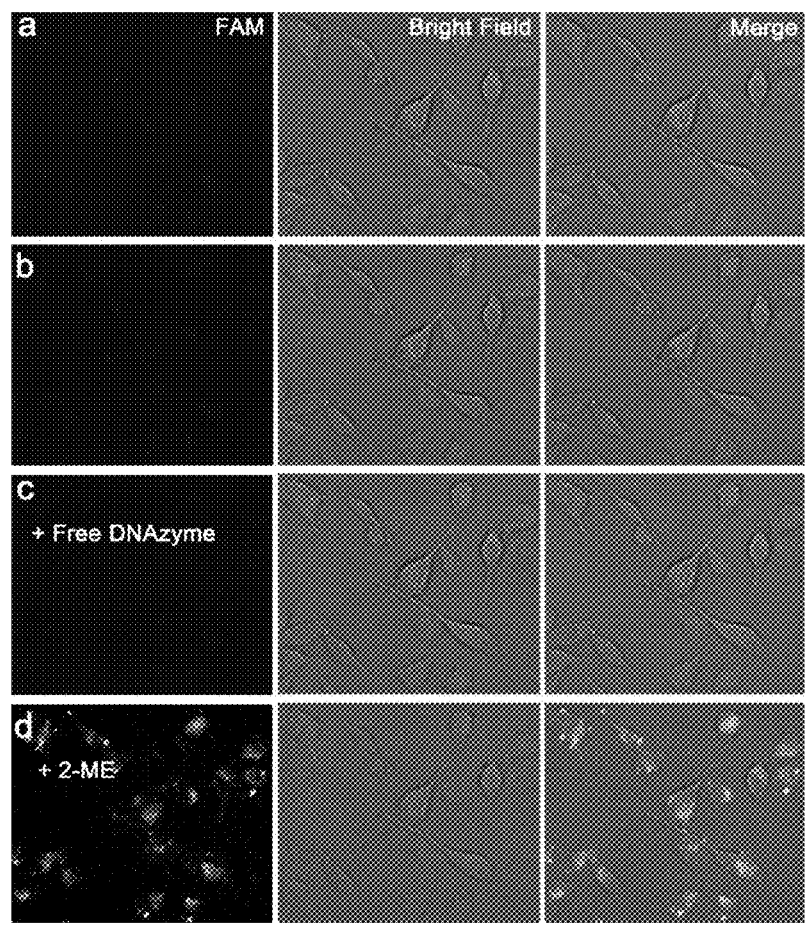

FIG. 32 depicts a schematic showing the experiments conducted to test whether adsorption of the DNAzyme motor system (functionalized AuNPs) could be a confounding issue. Fluorescence from the same set of the target MDA-MB-231 cancer cells were repeatedly measured after each treatment (Panel a, Panel b, Panel c, and Panel d). Results are shown in FIG. 33. If mutant DNAzyme motors (consisting of the functionalized AuNPs) were adsorbed on the cell surface (shown in the right-hand side portion of the schematic), the free control DNAzyme would cleave the fluorescent substrate from the AuNPs and produce fluorescence. Results in FIG. 22c show no detectable fluorescence from the target cells, suggesting that adsorption of the DNAzyme motor system on the cell surface is negligible.

FIG. 33 depicts images showing target MDA-MB-231 cancer cells after incubation with the mutant DNAzyme motor. (Panel a) Images of MDA-MB-231 cancer cells after incubation with the mutant DNAzyme motor for 2 h. (Panel b) Images of the cells after further incubation in the presence of $Mn^{2+}$ cofactor. Little fluorescence was observed, suggesting that the mutant DNAzyme motor is inactive. (Panel c) Images of the same MDA-MB-231 cancer cells after further incubation with 200 pM free control DNAzyme for 20 min. Little fluorescence is observed from the target cells, suggesting that adsorption of the DNAzyme motor system on the cell surface is negligible. (Panel d) Images of the MDA-MB-231 cancer cells from (Panel c) after additional treatment with 10 mM 2-mercaptoethanol (2-ME). Strong fluorescence is observed, suggesting that AuNPs of the mutant DNAzyme motor system have entered the target cells. Experiment procedures are shown in FIG. 32.

Figure 34:
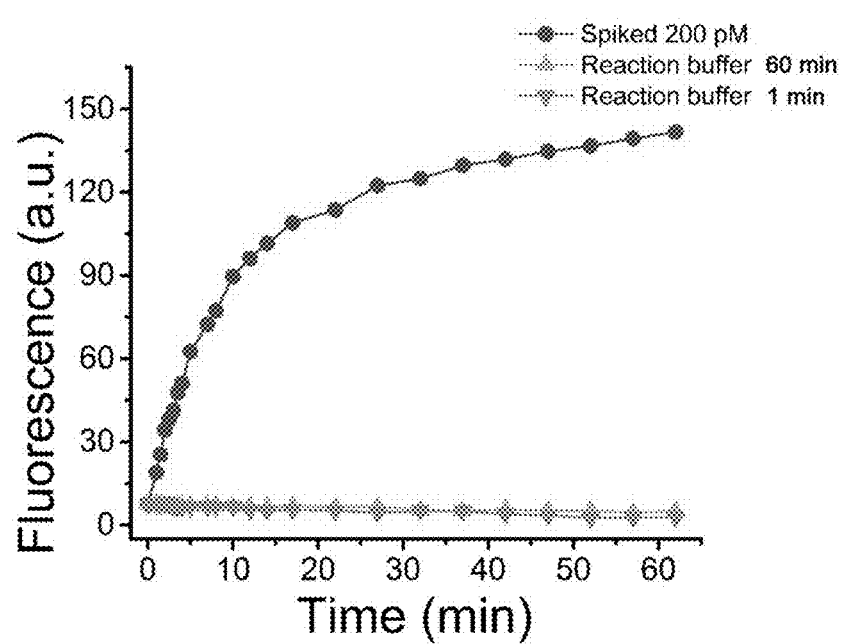

FIG. 34 depicts real-time monitoring of fluorescence generated by the DNAzyme motor in the reaction buffer after separation of the target cells. These experiments were designed to test whether the target miRNA could leak out of the cells and then initiate operation of the DNAzyme motor outside of cells. A DNAzyme reaction buffer, containing 25 mM Tris-acetate (pH 8.0) and 125 mM NaCl, was added to the MDA-MB-231 cells, and this reaction buffer solution was removed either 1 h after incubation with the cells or immediately after its contact with the cells (1 min). The DNAzyme motor system at an equivalent AuNP concentration of 230 pM and 0.5 mM $MnCl_2$ were added to these reaction buffer solutions. Fluorescence was monitored for 60 min. If the target miRNA were leaked out of the cells, then the target miRNA in this solution would initiate operation of the DNAzyme motor and produce fluorescent substrate. However, no fluorescence increase is observed, suggesting that very little target miRNA is present outside of the cells. As a positive control, further addition of 200 pM target miRNA into the solution results in an expected fluorescence increase. Relative standard deviations from replicate measurements were 4.1-8.4%.

DETAILED DESCRIPTION

In one aspect, described herein, is a DNAzyme motor that operates in living cells in response to a specific intracellular target. The whole motor system was constructed on a 20-nm gold nanoparticle (AuNP) decorated with hundreds of substrate strands serving as DNA tracks and dozens of DNAzyme molecules each silenced by a locking strand. Intracellular interaction of a target molecule with the motor system initiated the autonomous walking of the motor on the AuNP. An example DNAzyme motor responsive to a specific microRNA enabled amplified detection of the specific microRNA in individual cancer cells. Activated by specific intracellular targets, these self-powered DNAzyme motors will have diverse applications in the control and modulation of biological functions.

In one aspect, there is described herein, a motor system is constructed on a functionalized AuNP onto which are conjugated hundreds of substrate strands and dozens of DNAzyme molecules that are each silenced by a locking strand. The locking strand is designed to respond to a specific intracellular target. As a proof of principle, we choose a specific microRNA (miRNA) as the cellular target. For imaging purposes, we fluorescently labeled the locking strand with Cy5 (Cyanine 5) and the substrate strand with carboxyfluorescein (FAM). When the DNAzyme motor is inactive, the fluorescence from both Cy5 and FAM is quenched by the AuNP.

Once the DNAzyme motor is taken up by the cells, the intracellular miRNA (target) hybridizes with the locking strand through a strand-displacement reaction, releasing the locking strand from the DNAzyme. The unlocked DNAzyme then hybridizes to its substrate on the AuNP. In the presence of the cofactor $Mn^{2+}$, DNAzyme cleaves a substrate molecule, releasing the FAM-labeled segment. Cleavage of the DNA-RNA chimeric substrate provides the energy needed for the DNAzyme to move from one substrate strand to the next, achieving the autonomous and processive walking along the AuNP. Each walking step and substrate cleavage is accompanied by the release of the fluorescently-labeled segment of the substrate. As these molecules are detached from the AuNP, they become fluorescent. Monitoring of these fluorescent molecules detached from the AuNP enables real-time detection of the intracellular motion of the DNAzyme motor.

Figure 9:
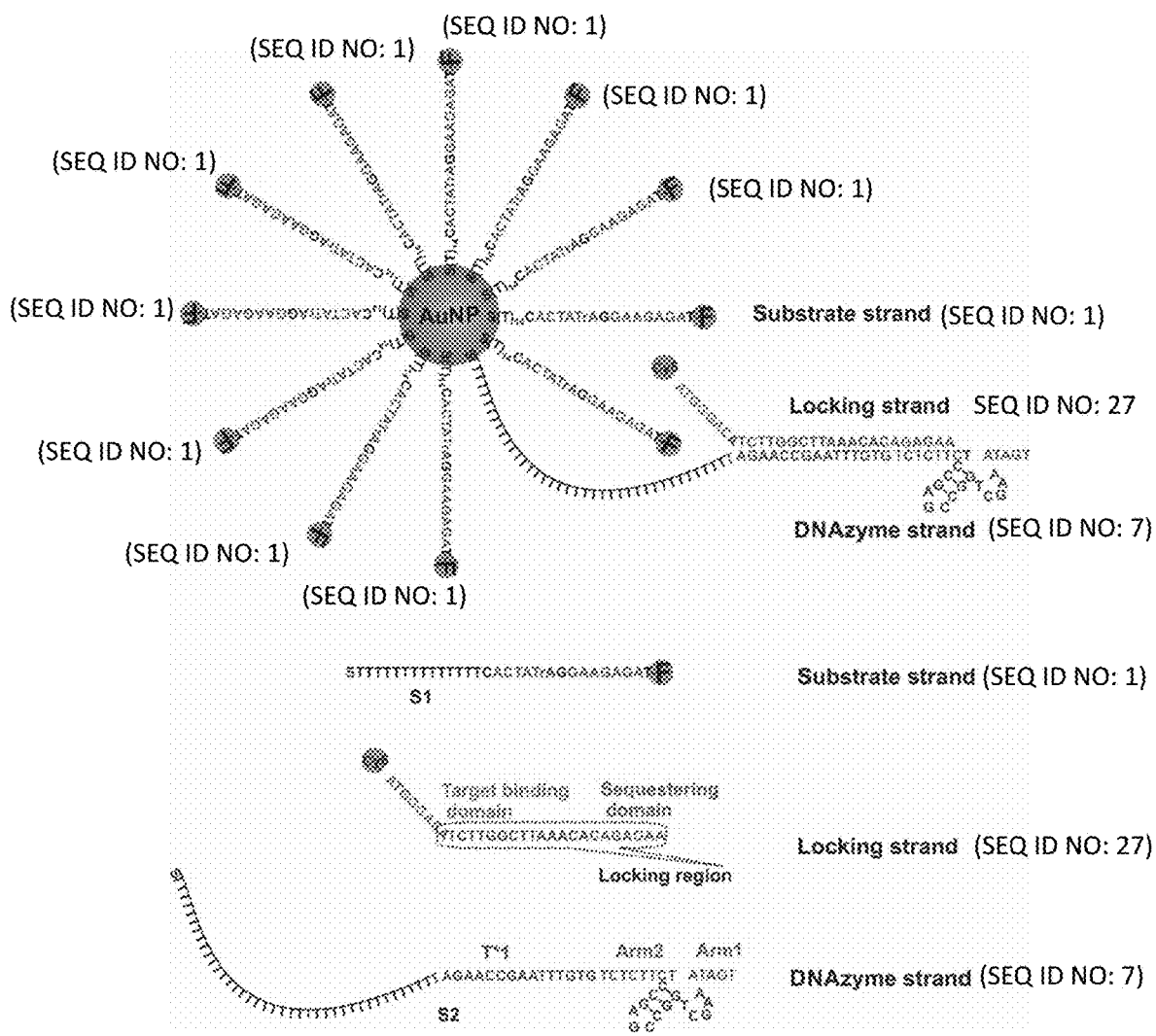
FIG. 9 depicts Design and sequences used in the miRNA-initiated DNAzyme motor. The complete motor system is a functionalized AuNP onto which are conjugated hundreds of substrate strands and dozens of blocked DNAzyme strands. The substrate strand is a DNA-RNA chimeric sequence that is composed of an RNA nucleotide flanked by two DNA domains complementary to Arm 1 and Arm 2 of the DNAzyme. To enhance the accessibility of the substrate strand to the DNAzyme, a 14-thymine spacer S1 is added to the substrate at the 5'-end that is conjugated to AuNP. The 3'-end of the substrate is labeled with a FAM molecule. The fluorescence of the FAM molecules on the substrate strands is quenched by the AuNP. The DNAzyme is extended to include a single-stranded spacer S2 linked to the 3'-end of Arm 2. The spacer S2 comprises a 42-thymine domain that is conjugated to AuNP and a 16-nt domain T*1. T*1 and Arm 2 of the DNAzyme strand form the locking region. A DNA locking strand is designed according to the target sequence and the DNAzyme strand. The locking strand contains a target-binding domain complementary to the target miRNA (miR-10b) and a 6-nt sequestering domain complementary to Arm 2 of the DNAzyme. The hybridization of the locking strand to the domain T*1 and Arm 2 forms a duplex with a 7-nt toehold at the 3'-end of the locking strand, which sequesters Arm 2 and prevents it from binding to the substrate strands, making the DNAzyme motor inactive.

The substrate strand (sequence in Table 1) is a DNA-RNA chimeric sequence that is composed of a RNA nucleotide flanked by two DNA domains. These two DNA domains are binding regions of two arms of the DNAzyme motor (FIG. 9). To enhance the accessibility of the substrate strand to the DNAzyme, we added a 14-thymine (T) spacer S1 to the substrate at the 5'-end that is conjugated to the AuNP. The 3'-end of the substrate is labeled with a FAM molecule whose fluorescence is quenched by the AuNP.

Figure 10:
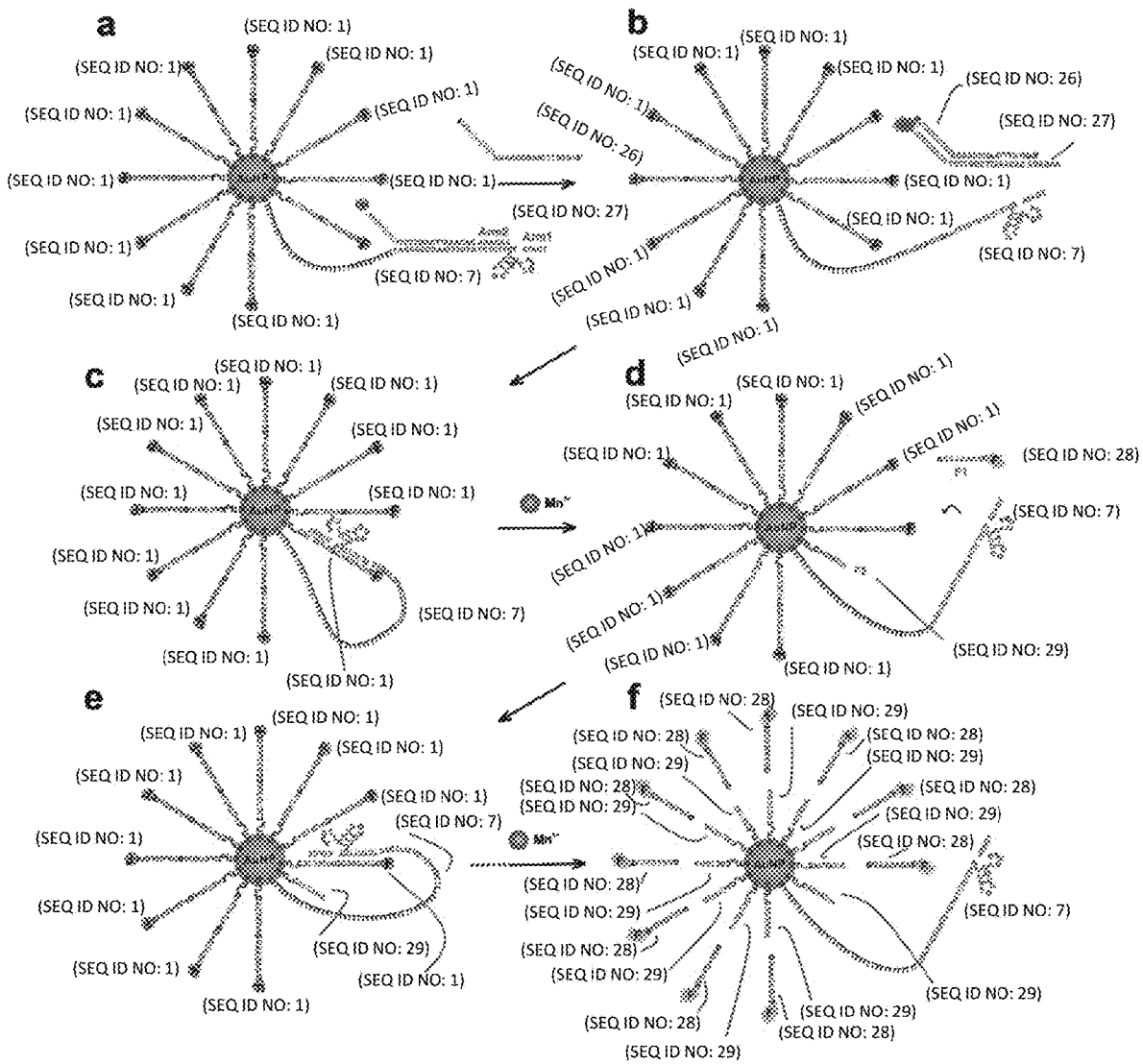
FIG. 10 The operation of the miRNA-initiated DNAzyme motor. In the absence of the target miRNA, the activity of the DNAzyme motor is blocked by the locking strand and the motor is not operational (Panel a). Upon addition of the target miRNA, the target miRNA hybridizes to the locking strand and releases it from the DNAzyme through a toehold-mediated strand displacement reaction, exposing the sequestered Arm 2 of the DNAzyme motor. The strand displacement reaction forms a duplex between the locking strand and target miRNA, making the locking strand stay away from the AuNP surface. Thus, the fluorescence of the Cy5 molecule in the duplex is restored, which is used to signal the location of target miRNA (Panel b). Meanwhile, the liberated DNAzyme motor hybridizes with a substrate strand on the AuNP (Panel c). In the presence of cofactor $Mn^{2+}$, DNAzyme is activated to cleave the substrate at the single-ribonucleotide junction, generating two DNA segments F1 and F2. FAM-containing F1 dissociates from Arm 2 and leaves the AuNP surface, restoring the fluorescence of the FAM molecule (Panel d). Meanwhile, the DNAzyme dissociates from the F2 and subsequently hybridizes to the next substrate strand, achieving the walking of the motor from one substrate strand to the next (Panel e). This stepwise walking is repeated autonomously, driving the DNAzyme motor to traverse along AuNP surface (Panel f).

The DNAzyme, a truncated form of 8-17E DNAzyme[36], consists of a catalytic core sequence flanked with binding Arm 1 and Arm 2 (FIG. 9). The DNAzyme is conjugated to the AuNP through a single-stranded spacer S2 linked to the 3'-end of Arm 2. The spacer S2 comprises a 42-thymine domain that is conjugated to the AuNP and provides the spatial distance needed for the motor walking. A 16-nt domain T*1 and Arm 2 form the locking region. The sequence selection of domain T*1 depends on the specific molecules designed to initiate the motor operation. For example, to construct a DNAzyme motor that is initiated by specific intracellular miRNA, we designed a locking strand that contains a target-binding domain complementary to the target miRNA (miR-10b) and a sequestering domain complementary to Arm 2. The hybridization of the locking strand to the domain T*1 and Arm 2 forms a duplex with a 7-nt toehold at the 3'-end of the locking strand, which sequesters Arm 2 from binding to the substrate strands on the track. With the locking strand hybridized to DNAzyme, the DNAzyme motor is inactive. It is the inactive DNAzyme motor that is introduced to living cells and subsequently switched on by the specific cellular target. When the inactive DNAzyme motor interacts with the target molecule, e.g., miRNA, the target miRNA can hybridize with the locking strand through a strand displacement reaction, exposing Arm 2 and initiating the operation of the DNAzyme motor (FIG. 10, Panel a-f).

In one aspect, there is described a nanomotor system, comprising:

a support;

a substrate strand comprising a first end conjugated to said support; a second end, said second end optionally comprising a first label and/or a moiety; and a substrate portion positioned between said first end and said second end;

a motor strand comprising a first end conjugated to the support; a second end; and a catalytic core positioned between said first end and said second end; said catalytic core is switchable between an active state and an inactive state, in said active state said catalytic core cleaves said substrate portion of said substrate strand; and a locking strand comprising a first end; a second end; and a locking region positioned between said first end and said second end, said locking region adapted to removably bind to said motor strand, said locking strand optionally comprising a label and/or a moiety at said first end or said second end, wherein when said locking strand binds to said motor strand, said catalytic core is in the inactive state, wherein when said locking strand is absent or is displaced from said motor strand by a target, said catalytic core is in the active state.

Support

In some examples, the support is a noble metal. In a specific example, the support is a gold nanoparticle. In a further specific example, the support is a 20 nm gold nanoparticle (AuNP).

In some examples, the support comprises a noble metal. In some examples, the support is gold or nanoparticle gold. In some examples, the support comprises a nanometal particle. In some examples, the support comprises a silica nanoparticle or microparticle.

Substrate Strand

In one example of the nanomotor system the substrate strand comprises a nucleotide sequence.

In a specific example of the nanomotor system, the substrate strand comprises a DNA:RNA chimeric nucleotide sequence.

In a specific example, the substrate strand is a DNA:RNA chimeric nucleotide sequence that is composed of a RNA nucleotide flanked by two DNA domains, a first DNA domain and a second DNA domain. The first DNA domain is complementary to Arm1 present on the motor strand. The second DNA domain is complementary to Arm2 of present on the motor strand.

In one example, the first end of said substrate strand comprises a spacer. In a specific example, the spacer comprises a polynucleotide spacer. In a more specific example, the spacer comprises a poly-thymine spacer. In a more specific example, the spacer comprises a 14-thymine spacer.

The substrate strand may also comprise a label and/or a moiety at it second end.

Specific examples of labels include, but are not limited to, a chemiluminescent group, a chromophore, a dye, a fluorophore, a radiolabel, metals, metal nanoparticles, colloidal metals, non-metal nanoparticle core-shell nanoparticles, such as nanoparticles comprising a dielectric coated with metal. In some examples, the label is FAM. In another example the label is Cy5 (Cyanine 5).

In some examples, the label is biotin or tag peptides.

The term "chemiluminescent group," as used herein, refers to a group which emits light as a result of a chemical reaction without the addition of heat.

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "fluorophore," as used herein refers to a composition that is inherently fluorescent or demonstrates a change in fluorescence upon binding to a biological compound or metal ion, i.e., fluorogenic. Fluorophores may contain substituents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as semiconductor nanocrystals and other fluorophores.

In some examples, the label is a radioactive nuclide (e.g., $^{125}I$, $^{3}H$, $^{14}C$, $^{32}P$).

Additionally or alternatively, in some example, the substrate strand comprises a moiety, such as a therapeutic entity.

In some examples, the moiety comprises nucleic acids (e.g., aptamer or DNAzyme), a siRNA, an antisense DNA, a peptide, a protein, a small molecule, and/or a drug.

The term "DNAzyme" as used herein means a DNA molecule that specifically recognizes and cleaves a distinct target nucleic acid sequence, which may be either DNA or RNA. In certain embodiments, the binding domains of the DNAzyme are complementary to the regions immediately flanking the cleavage site. It will be appreciated by those skilled in the art, however, that strict complementarity may not be required for the DNAzyme to bind to and cleave.

The term "siRNA" as used herein refers to one or more of a siRNA, shRNA, synthetic shRNA; miRNA.

The term "antisense DNA" as used herein refers to a DNA molecule that has a nucleotide sequence complementary to the "sense strand" of DNA and that is transcribed into RNA (the "sense transcript") that may be translated into the protein product of a gene. The term "sense DNA" as used herein refers to a DNA molecule that has a nucleotide sequence complementary to the "antisense strand" of DNA. The term "antisense transcript" is used to mean an RNA transcript that is transcribed from a sense strand DNA. An antisense transcript is capable of hybridizing under stringent conditions with a sense strand DNA.

The term "small molecule", as used herein, refers to a chemical agent including, but not limited to a compound, a chemical compound, a composition, a pharmaceutical composition, nucleobases, nucleosides, polynucleotides, polynucleotide analogs, aptamers, nucleotides, nucleotide analogs, organic or inorganic compounds (i.e., including heteroorganic and organometallic compounds), and salts, esters, carbohydrates, and other pharmaceutically acceptable forms of such compounds.

The term "aptamer" as used herein refers to a single stranded nucleic acid molecule capable of specifically binding to a target (e.g., an aptamer target).

The aptamer-target binding takes place, for example, via the structure compatibility, so-called "stacking interactions" in aromatic ring structures (stacking forces by electron interaction with adjacent bases), electrostatic interactions (e.g. van der Waals, ionic, dipole forces) and hydrogen bridge bonds.

The nucleic acid molecule may be a natural nucleic acid such as a DNA, an RNA, or a combination thereof. Also, the nucleic acid may partially or wholly comprise a non-natural nucleotide or a non-natural nucleic acid.

In a specific example, the nucleic acid is a DNA. Thus, in one example the aptamer is a DNA aptamer.

The term "DNA aptamer" as used herein refers to an aptamer consisting of deoxyribonucleotides.

Aptamers generally comprise between 5 and 120 nucleotides and can be selected in vitro according to the processes described herein, such as using SELEX with a crosslinking agent.

The term "aptamer target" as used herein refers to a substance that can serve as a target to which the nucleic acid aptamer binds.

An aptamer target can be any appropriate entity that can be detected when recognized by an aptamer, for example a biomaterial to which the nucleic acid aptamer can bind. In one example, the aptamer target comprises a protein or polypeptide.

As used herein, "protein," "polypeptide" and "peptide" are used interchangeably unless stated otherwise.

The aptamer target can be a nucleic acid, including DNA, RNA, and various subspecies of any thereof as disclosed herein or known in the art. The aptamer target can comprise a lipid. The aptamer target can comprise a carbohydrate. The aptamer target can comprise a low molecular-weight compound. The aptamer target can also be a complex, e.g., a complex comprising protein, nucleic acids, lipids and/or carbohydrates.

The aptamer target may be selected according to the intended use.

In one example, the aptamer target is a peptide, more preferably a polypeptide (e.g. a protein).

The term "protein" as used herein corresponds to an amino acid polymer. This includes the proteins, protein fragments, genetically modified proteins, oligopeptides and analogs thereof. The target protein may include a protein of therapeutic interest.

In some examples, the substrate strand can be hybridized to a quencher-containing and hairpin-forming further strand.

The moiety on said substrate strand may useful for the treatment of a subject having, or suspected of having, a disease or disorder.

The term "treatment", as used herein, refers to clinical intervention in an attempt to alter the course of the subject or cell being treated. In non-limiting examples, treatment includes preventing or delaying recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "subject" as used herein, refers to any mammal or non-mammal that would benefit from determining the benefit from treatment, treatment, diagnosis, therapeutic monitoring and/or prognosis. In certain examples a subject or patient includes, but is not limited to, humans, farm animals, companion animals (such as cats, dogs and horses), primates and rodent (such as mice and rats). In a specific embodiment, the subject is a human. The subject may be an infant, an adolescent, or an adult.

In one example, said disease or disorder is cancer.

The term "cancer" as used herein, refers to or describes the physiological condition in a mammal that is typically characterized by unregulated cell growth.

In some example, cancers include but are not limited to, breast cancer. Additional examples include, but are not limited to ovarian cancer, lung cancer, lymphoma, leukemia, germ cell cancer and primary of unknown origin (PRUNK).

Other examples of cancers include but are not limited to a cancer of the adrenal gland, appendix, bladder, blood, brain, bone, breast, bronchus, central nervous system, cervix, chest, colon, esophagus, eye, gallbladder, head, intestines, kidney, larynx, liver, lung, lymph nodes, mouth, neck, ovaries, pancreas, pharynx, pituitary, prostate, rectum, skin, stomach, testicles, throat, thymus, thyroid, uterus, urinary tract, or vagina, or is a leukemia, or lymphoma.

Other example of cancer include but are not limited to biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

In a specific example, the subject has breast cancer or is suspected of having breast cancer.

As used herein, "breast cancer" refers to a cancer that starts in a tissue of the breast, such a ductal carcinoma or lobular carcinoma and includes both early stage and late stage breast cancer. Breast cancer may be invasive or non-invasive and/or comprise malignant epithelial cells. Optionally, breast cancer may be classified according to molecular subtypes such as estrogen receptor (ER) and/or Her2 positive or negative as known in the art. In another embodiment, "breast cancer" refers to a cancer that starts in a non-adjacent tissue but which later metastasizes to the breast.

As used herein, "metastasis" refers to the spread of breast cancer from the breast to a non-adjacent part, tissue or organ of the test subject. In one embodiment, metastasis includes "lymph node metastasis" and/or "distant metastasis." As used herein, "lymph node metastasis" refers to the spread of cancer to the lymph system of a test subject. For example, lymph node metastasis includes the presence of malignant cells in one or more lymph nodes of a test subject, such as in the lymph nodes that are proximal to the breast cancer, for example in one or more sentinel lymph nodes. "Distant metastasis" refers to metastasis that is present in another non-adjacent part, tissue or organ of a test subject such as in lung, liver, brain or bone or in a distal lymph node.

In one example, a sample containing cancerous cells or suspected as containing cancerous cells is obtained from the breast cancer patient. Collection of such a sample is well known to the skilled worker. In a specific example, the sample is a breast tissue sample. Methods of obtaining a breast tissue sample, processing and/or storage of such a sample are also well known to the skilled worker.

Samples, also referred to as biological samples, from a subject include, but are not limited to bodily fluids.

As used herein the term "bodily fluid" refers to any fluid found in the body of which a sample can be taken for analysis. Non-limiting examples of bodily fluids include blood, plasma, serum, lymph, sudor, saliva, tears, sperm, vaginal fluid, faeces, urine or cerebrospinal fluid.

Biological samples from a subject also includes samples derived, e.g., by biopsy, from cells, tissues or organs. This also encompasses samples comprising subcellular compartments or organelles, such as the mitochondria, Golgi network or peroxisomes. Biological samples also encompass gaseous samples, such as volatiles of an organism. Biological samples may be derived from a subject.

Techniques for obtaining different types of biological samples are well known in the art.

Biological samples may be pre-treated before use. Pre-treatment may include treatments required to release or separate the compounds or to remove excessive material or waste. Suitable techniques comprise centrifugation, extraction, fractioning, purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art.

Examples of moieties which may be included in the substrate strand and that may be used in the treatment of breast cancer include, but are not limited to, chemotherapeutics such as anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of targeted therapy include trastuzumab (Herceptin), lapatinib (Tykerb), bevacizumab (Avastin), pertuzumab (Perjeta), and everolimus (Afinitor). Additional examples of moieties which may be included in the substrate strand and that may be used in the treatment of breast cancer include, but are not limited to, selective estrogen receptor modulators (SERMs), such as tamoxifen, raloxifene, endoxifene, toremifene, lasofoxifene, pipendoxifene, bazedoxifene, and ospemifene, aromatase inhibitors, such anastrozole, letrozole, exemestane, formestane, fadrozole, aminoglutethimide, and testolactone, a HER2 intervention drug, such as a HER2 inhibitor, such as Herceptin (trastuzumab), pertuzumab, and lapatinib, and estrogen-receptor downregulators, such as fulvestrant (ICI 182,780).

Motor Strand

In one example, the motor strand comprises a first end conjugated to the support, a second end, and a motor positioned between said first end and said second end, said motor is switchable between an active state and an inactive state, in said active state said motor is operable to cleave said substrate portion of said substrate strand.

In one example, the motor comprises a DNAzyme.

In a specific example, the DNAzyme is a truncated form of 8-17E DNAzyme.

It will be appreciated that alternate DNAzymes may be used.

Additional examples of DNAzymes include, but are not limited to, the following:

Metal-Assisted DNAzyme (None Specific to Many Metal Ions including $Pb^{2+}$, $Mn^{2+}$, $Mg^{2+}$, $Zn^{2+}$, $Ca^{2+}$, etc)

Santoro, S. W.; Joyce, G. F., A general purpose RNA-cleaving DNA enzyme. *P Natl Acad Sci USA* 1997, 94, (9), 4262-4266.
DNAzyme 8-17, ($k_{obs}$)~0.5 $min^{-1}$
DNAzyme 8-17E, ($k_{obs}$)~1 $min^{-1}$
DNAzyme Mg5, ($k_{obs}$)~2 $min^{-1}$ Brown, A. K.; Li, J.; Pavot, C. M. B.; Lu, Y., A lead-dependent DNAzyme with a two-step mechanism. *Biochemistry-Us* 2003, 42, (23), 7152-7161.
DNAzyme 10-23, ($k_{obs}$)~0.22 $min^{-1}$ Cairns, M. J.; Hopkins, T. M.; Witherington, C.; Sun, L. Q., The influence of arm length asymmetry and base substitution on the activity of the 10-23 DNA enzyme. *Antisense Nucleic A* 2000, 10, (5), 323-332.

Metal Specific DNAzyme
$Pb^{2+}$, ($k_{obs}$)~1 $min^{-1}$
Breaker, R. R.; Joyce, G. F. A DNA enzyme that cleaves RNA. Chem. Biol. 1994, 1, 223-229
$Zn^{2+}$, ($k_{obs}$)~1.35 $min^{-1}$
Li, J.; Zheng, W. C.; Kwon, A. H.; Lu, Y., In vitro selection and characterization of a highly efficient Zn(II)-dependent RNA-cleaving deoxyribozyme. *Nucleic Acids Res* 2000, 28, (2), 481-488.
$Cu^{2+}$, ($k_{obs}$)~0.2 $min^{-1}$
Carmi, N.; Balkhi, S. R.; Breaker, R. R., Cleaving DNA with DNA. *P Natl Acad Sci USA* 1998, 95, (5), 2233-2237.
$UO2^{2+}$, ($k_{obs}$)~1 $min^{-1}$
Liu, J. W.; Brown, A. K.; Meng, X. L.; Cropek, D. M.; Istok, J. D.; Watson, D. B.; Lu, Y., A catalytic beacon sensor for uranium with parts-per-trillion sensitivity and millionfold selectivity. *P Natl Acad Sci USA* 2007, 104, (7), 2056-2061.
$Cd^{2+}$, ($k_{obs}$)~0.12 $min^{-1}$
Huang, P. J. J.; Liu, J. W., Rational evolution of Cd2+-specific DNAzymes with phosphorothioate modified cleavage junction and Cd2+ sensing. *Nucleic Acids Res* 2015, 43, (12), 6125-6133.
$Hg^{2+}$, ($k_{obs}$)~0.013 $min^{-1}$
Hollenstein, M.; Hipolito, C.; Lam, C.; Dietrich, D.; Perrin, D. M., A highly selective DNAzyme sensor for mercuric ions. *Angew Chem Int Edit* 2008, 47, (23), 4346-4350.
$Na^{+}$, ($k_{obs}$)~0.1 $min^{-1}$
Torabi, S. F.; Wu, P. W.; McGhee, C. E.; Chen, L.; Hwang, K.; Zheng, N.; Cheng, J. J.; Lu, Y., In vitro selection of a sodium-specific DNAzyme and its application in intracellular sensing. *P Natl Acad Sci USA* 2015, 112, (19), 5903-5908.
$Ag^{+}$, ($k_{obs}$)~0.41 $min^{-1}$
Saran, R.; Liu, J. W., A Silver DNAzyme. *Anal Chem* 2016, 88, (7), 4014-4020.

In one example, the motor strand comprises a spacer. In a specific example, the spacer comprises a polynucleotide spacer. In a specific example, the spacer comprises a polythymine spacer. In a specific example, the spacer comprises a 42-thymine spacer.

In some examples, the motor strand comprises a locking region adjacent said spacer, said locking region comprising a first domain (T*1) and a first arm (e.g, Arm2 in FIG. 9); and a second arm (e.g., Arm1 S1), said motor positioned between said first arm and said second arm.

Locking Strand

In one example, the locking strand comprises a first end optionally having a second label and/or a moiety, a second end, and a locking region positioned between said first end and said second end, said locking region adapted to removably bind to said DNA motor strand. For example, the locking strand may removably bind through hybridization, competitive binding, base pairing, and the like.

In one example, said locking region on said locking strand comprises a target binding domain and a sequestering domain, wherein said target binding domain comprises a sequence complementary to said target sequence, wherein said sequestering domain comprises a sequence complementary to said first arm of said motor strand.

Target

As described herein, the nanomotor is activated by a target. In one example, the target is an intracellular target. In one example, the target is extracellular, and is transported across a biological membrane (such as a plasma membrane) to an intracellular location. Such transport of a target across a membrane may be passive or mediated.

In some examples, the target includes but is not limited to small molecules, proteins, and cells nucleic acids, including mRNA, miRNA, and DNA.

In some examples, the target is an intracellular target. In some example, the target is microRNA. In a specific example, the mircoRNA is miR-10b.

In some examples, the target is a prodrug. The term "prodrug" as used herein, refers to a derivative of a substance that, following administration, is metabolized in vivo, e.g. by hydrolysis or by processing through an enzyme, into an active metabolite.

In other examples, the target is an analyte or analyte of interest.

The term "analyte of interest", as used herein, means any molecule, or aggregate of molecules. Also included are fragments of any molecule found in a sample. An analyte of interest can be an organic compound, an organometallic compound, or an inorganic compound.

In some examples, the analyte includes, but is not limited to a metabolite, an amino acid, a herbicide, a pesticide, an environmental pollutant, an analyte, a veterinary drug, a drug, a drug of abuse, and/or a small molecule.

In other examples, the analyte includes, but is not limited to a nucleic acid (e.g., DNA, RNA), an antigen, a receptor, a receptor ligand, or a peptide, a lipoprotein, a glycoprotein, a ribo- or deoxyribonucleoprotein, a polysaccharide, a lipopolysaccharide, a lipid, a fatty acid, a vitamin, a pharmaceutical compound (e.g., tranquilizers, barbiturates, opiates, alcohols, tricyclic antidepressants, benzodiazepines, anti-virals, anti-fungals, steroids, cardiac glycosides, or a metabolite of any of the preceding), a hormone, a growth factor, an enzyme, a coenzyme, an apoenzyme, haptens, lechtins, a substrate, a cellular metabolite, a cellular component or organelle (e.g., a membrane, a cell wall, a ribosome, a chromosome, a mitochondria, or a cytoskeleton component). Also included are environmental pollutants.

The term "analog of the analyte of interest", as used herein, means a substance that competes with the analyte of interest for binding to a specific binding partner. An analog of the analyte of interest can be a known amount of the analyte of interest itself that is added to compete for binding to a specific binding partner with analyte of interest present in a sample.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound.

The term "amino acid" as used herein refers to a group or compound that consists of an amino group, a carboxyl group, an H atom and a distinctive R group (or side chain). "Amino acid" includes, α-amino acids, β-amino acids, σ-amino acids, and γ-amino acids. α-Amino acids consists of an amino group, a carboxyl group, a H atom and a distinctive R group which is bonded to the α-carbon atom. "Amino acid" includes natural amino acids, unnatural amino acids, amino acid analogs, amino acid mimics, and the like.

The term "natural" as used herein refers to a group or compound that is present in or produced by nature.

The term "unnatural" or "non-natural" refers to a group or compound that is not present in or produced by nature. An "unnatural" or "non-natural" group or compound is typically produced by human intervention. An "unnatural" or "non-natural" group or compound is artificial.

In one example, the term "amino acid" refers to one of the naturally occurring twenty amino acids (i.e. α-amino acids), as shown below. Amino acids consist of an amino group, a carboxyl group, an H atom and a distinctive R group (or side chain), all of which are bonded to an α-carbon atom. As a result of containing three differing groups on the α-carbon atom, amino acids contain a chiral center, and therefore may exist as either of two optically active enantiomers, the D- and the L-. Naturally occurring acids are found as their L-derivatives.

In another example, the amino acid is an "unnatural amino acid", "non-natural amino acid", "amino acid analog", "amino acid mimic". "Unnatural amino acid", "non-natural amino acid", "amino acid analog", "amino acid mimic" and the like, as used herein, refer to an amino acid that is not one of the 20 natural amino acids. These terms refer to amino acids wherein the fundamental amino acid molecule has been modified in some way. Such modifications include, though are not limited to side chain variations; substitutions on, or alterations to, the amino-CH-carboxyl backbone; D-enantiomers; combinations thereof and the like.

These terms also include, but are not limited to, amino acids which occur naturally but are not naturally incorporated into a growing polypeptide chain. Further, these terms also include, but are not limited to, amino acids which do not occur naturally and may be obtained synthetically or may be obtained by modification of natural, naturally occurring or non-natural amino acids.

Administration

The nanomotor systems described herein may be used in vitro or in vivo.

The nanomotor system may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

A nanomotor system may be administered alone or in combination with other treatments, either simultaneously or sequentially, dependent upon the condition to be treated.

In treating a subject, a therapeutically effective amount may be administered to the subject.

As used herein, the term "therapeutically effective amount" refers to an amount that is effective for preventing, ameliorating, or treating a disease or disorder.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

Nanomotor systems disclosed herein may be used in the methods described herein in combination with standard treatment regimes, as would be known to the skilled worker.

Target Detection

A nanomotor system as described herein may be used to provide in vitro or in vivo detection or imaging of a target, to provide a diagnostic readout (e.g., prognosis, diagnosis, therapeutic monitoring, or theranostic).

The term "prognosis" as used herein refers to the prediction of the likelihood of cancer-attributable death or progression, including recurrence, metastatic spread, and drug resistance, of a neoplastic disease, such as breast cancer.

The term "prognostic marker" as used herein refers to a marker that informs about the outcome of a patient in the absence of systemic therapy or portends an outcome different from that of the patients without the marker, despite empiric (not targeted to the marker) systemic therapy.

The term "predictive marker" as used herein refers to a marker that predicts that differential efficacy (benefit) of a particular therapy based on marker status.

The term "diagnosis" as used herein refers to the identification of a molecular and/or pathological state, disease or condition, such as the identification of breast cancer, or other type of cancer.

The term "therapeutic monitoring" as used herein refers to the observation of the response of the subject to the treatment administered to it.

Thus, in another aspect, there is described a method for biomarker detection using a nanomotor system. In one example, there is described a method for biomarker detection in a subject. In another example, there is described a method for biomarker detection in a sample from a subject.

The term "biomarker" refers, in the most general sense, to a biological metric of the condition of a cell or patient health or disease status. A non-limiting listing of general biomarkers includes biologically derived molecules found in a mammal, cell surface markers, differential expression of, for example, a protein, protein truncations, phosphorylations, dephosphorylations, ubiquitination, de-ubiquitination, metabolites, hormones at any stage of biosynthesis, cytokines, chemokines, and combinations thereof. A subset of biomarkers are used for diagnostic and therapeutic selection purposes to help pathologists diagnose disease and to help doctors prescribe therapy.

In some aspects, the target is useful for prognosis, diagnosis, or therapeutic monitoring. In some aspects, the target is useful as a biomarker or a predictive marker.

Kits

Method of the invention are conveniently practiced by providing the compounds and/or compositions used in such method in the form of a kit. Such kit preferably contains the composition. Such a kit preferably contains instructions for the use thereof.

In some example, the kit comprises one or more of the following:

a support;

a substrate strand comprising a first end conjugated to said support; a second end, said second end optionally comprising a first label and/or a moiety; and a substrate portion positioned between said first end and said second end;

a motor strand comprising a first end conjugated to the support; a second end; and a catalytic core positioned between said first end and said second end; said catalytic core is switchable between an active state and an inactive state, in said active state said catalytic core cleaves said substrate portion of said substrate; and a locking strand comprising a first end; a second end; and a locking region positioned between said first end and said second end, said locking region adapted to removably bind to said motor strand, said locking strand optionally comprising a label and/or a moiety at said first end or said second end, wherein when said locking strand binds to said motor strand, said catalytic core is in the inactive position, wherein when said locking strand is absent or is displaced from said motor strand by a target, said catalytic core is in the active position.

It will be appreciated that the kit may comprise one or more of the individual components, namely: a support a substrate strand comprising a first end which may be conjugated to said support; a second end, said second end optionally comprising a first label and/or a moiety; and a substrate portion positioned between said first end and said second end; a motor strand comprising a first end which may be conjugated to the support; a second end; and a catalytic core positioned between said first end and said second end; said catalytic core is switchable between an active state and an inactive state, in said active state said catalytic core cleaves said substrate portion of said substrate; and a locking strand comprising a first end; a second end; and a locking region positioned between said first end and said second end, said locking region adapted to removably bind to said motor strand, said locking strand optionally comprising a label and/or a moiety at said first end or said second end.

To gain a better understanding of the invention described herein, the following examples are set forth. It should be understood that these examples are for illustrative purposes only. Therefore, they should not limit the scope of this invention in anyway.

EXAMPLES

Figure 1:
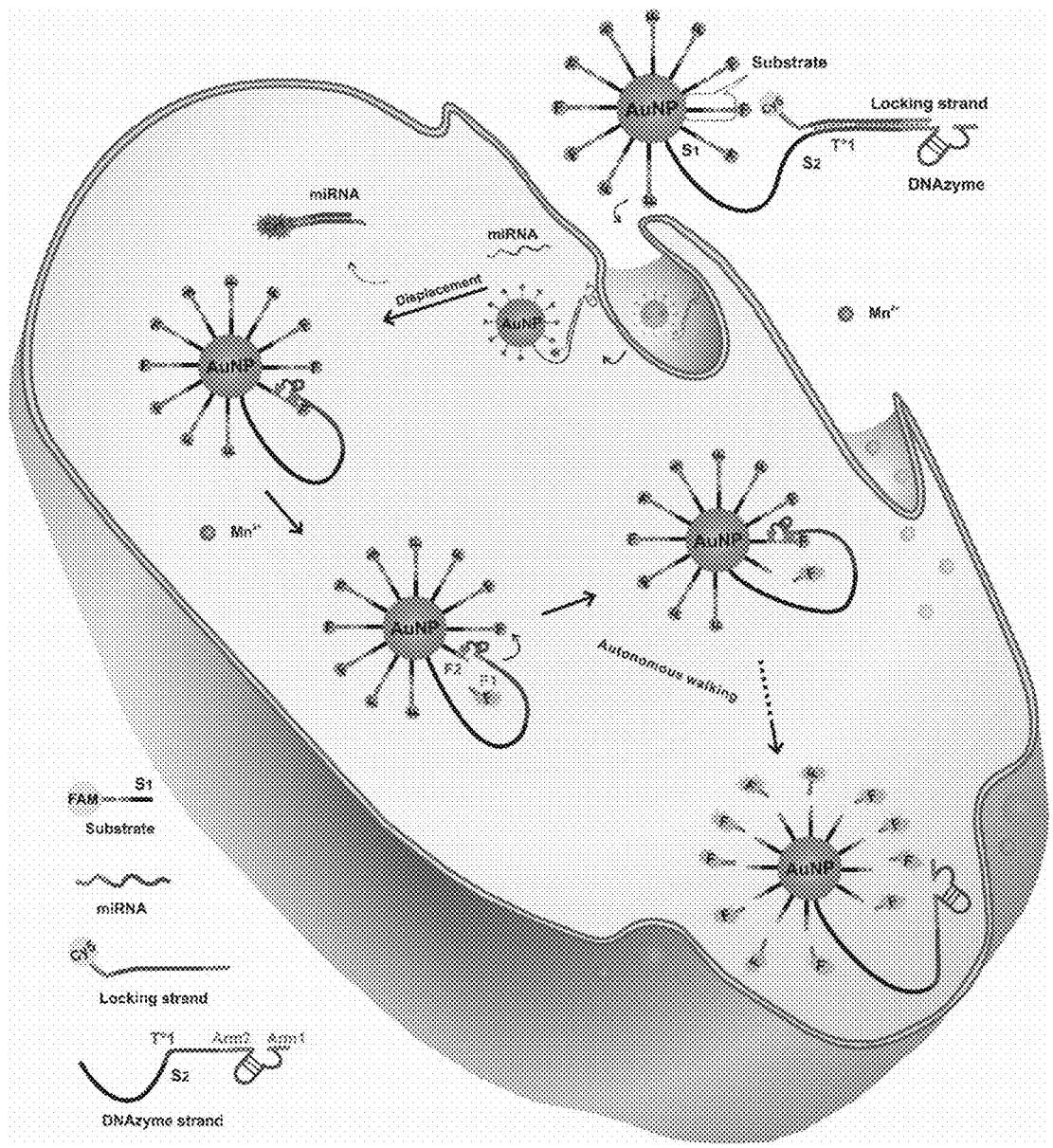
FIG. 1 depicts intracellular operation of a DNAzyme motor initiated by a specific microRNA (miRNA). The DNAzyme motor system is constructed on the gold nanoparticle (AuNP). The AuNP is functionalized with hundreds of substrate strands and dozens of DNAzyme molecules that are each silenced by a locking strand. Inside the cells, the target microRNA hybridizes to the locking strand and releases the locking strand from the DNAzyme through a strand displacement reaction. The unlocked DNAzyme subsequently hybridizes to its substrate. The cofactor $Mn^{2+}$ activates the DNAzyme, which cleaves the substrate, generating two DNA segments F1 and F2. The FAM-containing F1 segment is released from the AuNP surface, restoring its fluorescence that is previously quenched by the AuNP. Meanwhile, the DNAzyme dissociates from F2 and subsequently hybridizes to the next substrate strand, achieving the walking of the motor from one substrate strand to the next. This stepwise walking is repeated autonomously, driving the DNAzyme motor to traverse along the AuNP surface. Monitoring the fluorescence of FAM provides real-time imaging of the intracellular operation of the motor in live cells.

Design Principle of the DNAzyme Motor Enabling Target-Initiated Intracellular Operation FIG. 1 depicts the overall concept and the intracellular operation of a DNAzyme motor. The motor system is constructed on a functionalized AuNP onto which are conjugated hundreds of substrate strands and dozens of DNAzyme molecules that are each silenced by a locking strand (FIG. 9). The locking strand is designed to respond to a specific intracellular target. As a proof of principle, we choose a specific microRNA (miRNA) as the cellular target. For imaging purpose, we fluorescently labeled the locking strand with Cy5 and the substrate strand with carboxyfluorescein (FAM). When the DNAzyme motor is inactive, the fluorescence from both Cy5 and FAM is quenched by the AuNP.

Once the DNAzyme motor is taken up by the cells, the intracellular miRNA hybridizes with the locking strand through a strand-displacement reaction, releasing the locking strand from the DNAzyme. The unlocked DNAzyme then hybridizes to its substrate on the AuNP. In the presence of the cofactor $Mn^{2+}$, DNAzyme cleaves a substrate molecule, releasing the FAM-labeled segment. Cleavage of the DNA-RNA chimeric substrate provides the energy needed for the DNAzyme to move from one substrate strand to the next, achieving the autonomous and processive walking along the AuNP. Each walking step and substrate cleavage is accompanied by the release of the fluorescently-labeled segment of the substrate. As these molecules are detached from the AuNP, they become fluorescent. Monitoring of these fluorescent molecules detached from the AuNP enables real-time detection of the intracellular motion of the DNAzyme motor.

The substrate strand (sequence in Table 1) is a DNA-RNA chimeric sequence that is composed of a RNA nucleotide flanked by two DNA domains. These two DNA domains are binding regions of two arms of the DNAzyme motor (FIG. 9). To enhance the accessibility of the substrate strand to the DNAzyme, we added a 14-thymine (T) spacer S1 to the substrate at the 5'-end that is conjugated to the AuNP. The 3'-end of the substrate is labeled with a FAM molecule whose fluorescence is quenched by the AuNP.

TABLE 1

Oligonucleotide sequences used in the study

| Oligonucleotides | Sequences (5'→3') | SEQ ID NO: |
|---|---|---|
| Substrate strand | HS-(T)$_{14}$CACTATrAGGAAGAGAT-6-Carboxyfluorescein (FAM) | 1 |

TABLE 1-continued

Oligonucleotide sequences used in the study

| Oligonucleotides | Sequences (5'→3') | SEQ ID NO: |
|---|---|---|
| Lock -4 | GAGACACAAATTCGGTTCTACAGGGTA | 2 |
| Lock -5 | AGAGACACAAATTCGGTTCTA CAGGGTA | 3 |
| Lock -6 | AAGAGACACAAATTCGGTTCTACAGGGTA-Cy5 | 4 |
| Lock -7 | GAAGAGACACAAATTCGGTTCTACAGGGTA | 5 |
| Free control DNAzyme | ATCTCTTCTCCGAGCCGGTCGAAATAGTGAA<br>Arm 1 Catalytic core Arm2 | 6 |
| DNAzyme strand linked to AuNP | HS-(T)$_{43}$AGAACCGAATTTGTGTCTCTTCTCCGAGCCGGTC GAAATAGT<br>Arm 1 Catalytic core Arm2 | 7 |
| Mutant DNAzyme strand linked to AuNP | HS-(T)$_{43}$AGAACCGAATTTGTGTCTCTTCTCCGATCCGGTC TAAATAGT | 8 |
| Target microRNA-10b | UACCCUGUAGAACCGAAUUUGUG | 9 |
| DNA Target | TACCCTGTAGAACCGAATTTGTG | 10 |
| Mismatch-1 | TACACTGTAGAACCGAATTTGTG | 11 |
| Mismatch-2 | TACCATGTAGAACCGAATTTGTG | 12 |
| Mismatch-3 | TACCCTGTAGAAGCGAATTTGTG | 13 |
| Mismatch-4 | TACCCTGTAGAACCTAATTTGTG | 14 |
| Mismatch-5 | TACCCTGTAGAACCGAATTTTTG | 15 |
| Biotin-DNAzyme 8-17E | Biotin-TTTTTTTTTTTTTTTTTTTTTTTTTTTTTTTTTTTTTTG TCTCTTCTCCGAGCCGGTCGAAATAGT | 16 |
| Biotin-DNAzyme 8-17 | Biotin-TTTTTTTTTTTTTTTTTTTTTTTTTTTTTTTTTTTTTTG TCTCTTCTCCGAGCCGGACGAATAGT | 17 |
| Biotin-DNAzyme 10-23 | Biotin-TTTTTTTTTTTTTTTTTTTTTTTTTTTTTTTTTTTTTTT TCTCTTCAGGCTAGCTACAACGATAGT | 18 |
| Poly(T)-biotin | HS-TTTTTTTTTTTTTTTTTTTTTTTTTTT-Biotin | 19 |
| Substrate strand for DNAzyme 10-23 | HS-TTTTTTTTTTTTTACTAT rGrU GAAGAGAT-FAM | 20 |

The DNAzyme, a truncated form of 8-17E DNAzyme[36], consists of a catalytic core sequence flanked with binding Arm 1 and Arm 2 (FIG. 9). The DNAzyme is conjugated to the AuNP through a single-stranded spacer S2 linked to the 3'-end of Arm 2. The spacer S2 comprises a 42-thymine domain that is conjugated to the AuNP and provides the spatial distance needed for the motor walking. A 16-nt domain T*1 and Arm 2 form the locking region. The sequence selection of domain T*1 depends on the specific molecules designed to initiate the motor operation. For example, to construct a DNAzyme motor that is initiated by specific intracellular miRNA, we designed a locking strand that contains a target-binding domain complementary to the target miRNA (miR-10b) and a sequestering domain complementary to Arm 2. The hybridization of the locking strand to the domain T*1 and Arm 2 forms a duplex with a 7-nt toehold at the 3'-end of the locking strand, which sequesters Arm 2 from binding to the substrate strands on the track. With the locking strand hybridized to DNAzyme, the DNAzyme motor is inactive. It is the inactive DNAzyme motor that is introduced to living cells and subsequently switched on by the specific cellular target. When the inactive DNAzyme motor interacts with the target molecule, e.g., miRNA, the target miRNA can hybridize with the locking strand through a strand displacement reaction, exposing Arm 2 and initiating the operation of the DNAzyme motor (FIG. 10a-10f).

Labeling of a Cy5 molecule at the 3'-end of the locking strand is for the purpose of detecting the intracellular location of the target molecule. When the locking strand hybridizes to the DNAzyme strand, the fluorescence of the Cy5 molecule is quenched by the AuNP. However, when the target miRNA forms a duplex with the locking strand through the strand displacement reaction, the locking strand is removed from the AuNP surface. Thus, the fluorescence of the Cy5 molecule in the duplex is restored, signaling the location of the target miRNA.

To ensure efficient sequestering of the DNAzyme and high mobility of the motor after initiation, we designed Arm 1 and Arm 2 to contain 5 nt and 7 nt, respectively (FIG. 9). A 7-nt Arm 2 allows the locking strand to occupy most or all nt of Arm 2, thus efficiently inhibiting Arm 2 from binding to substrate strands on the AuNP. Additionally, when the duplex between the target miRNA and the locking strand is formed through the strand displacement reaction, the duplex can be efficiently dissociated from Arm 2 because the hybrid (<7 nt) between Arm 2 and the sequestering domain is unstable. Importantly, the 7-nt Arm 2 is sufficient for the DNAzyme to form a stable complex between the DNAzyme and the substrate strand conjugated on the same AuNP. Confining the DNAzyme and its substrate on a 20-nm AuNP surface leads to a high local concentration of DNAzyme and substrate, enhancing their hybridization. The estimated melting temperature ($T_m$) is 41° C. for the hybrid of the DNAzyme with its substrate on the same AuNP. Therefore, when the locking strand is liberated by the target miRNA, the DNAzyme motor is available to interact with a substrate stand on the AuNP track. In the presence of divalent metal cofactors, such as $Mn^{2+}$, the DNAzyme cleaves the substrate at the single-ribonucleotide junction, generating two DNA segments F1 and F2. The FAM-containing F1 then dissociates from Arm 2 and escapes from the AuNP surface, and therefore its fluorescence is restored. Because Arm 1 only contains 5 nt, the remaining hybrid between Arm 1 and F2 (the substrate segment attached to AuNP) becomes unstable ($T_m$=7° C.). The DNAzyme therefore dissociates from F2 and subsequently hybridizes to the second substrate strand, achieving the walking of the DNAzyme motor from one substrate strand to the next. This stepwise walking, fueled by DNAzyme-catalyzed cleavage of the substrate, is repeated, driving the DNAzyme motor to traverse along the AuNP surface (FIG. 10). Like other DNA motors that use DNA tracks built on nano- and micro-materials[8, 30, 31], walking of the DNAzyme motor along the AuNP is stochastic.

Each walking step of the DNAzyme motor releases one F1 from the AuNP surface, restoring the fluorescence of the FAM molecule in F1. Therefore, the fluorescence increase corresponds to the steps that DNAzyme motors have moved during the specific operating time. The intracellular operation of the DNAzyme motor can be imaged in real-time by measuring the fluorescence increase. Additionally, the fluorescence increase is proportional to the amount of the target miRNA strand in the cell, enabling in situ amplified detection of miRNA in living cells.

Evaluation of the DNAzyme Motor in Test Tubes

Figure 2:
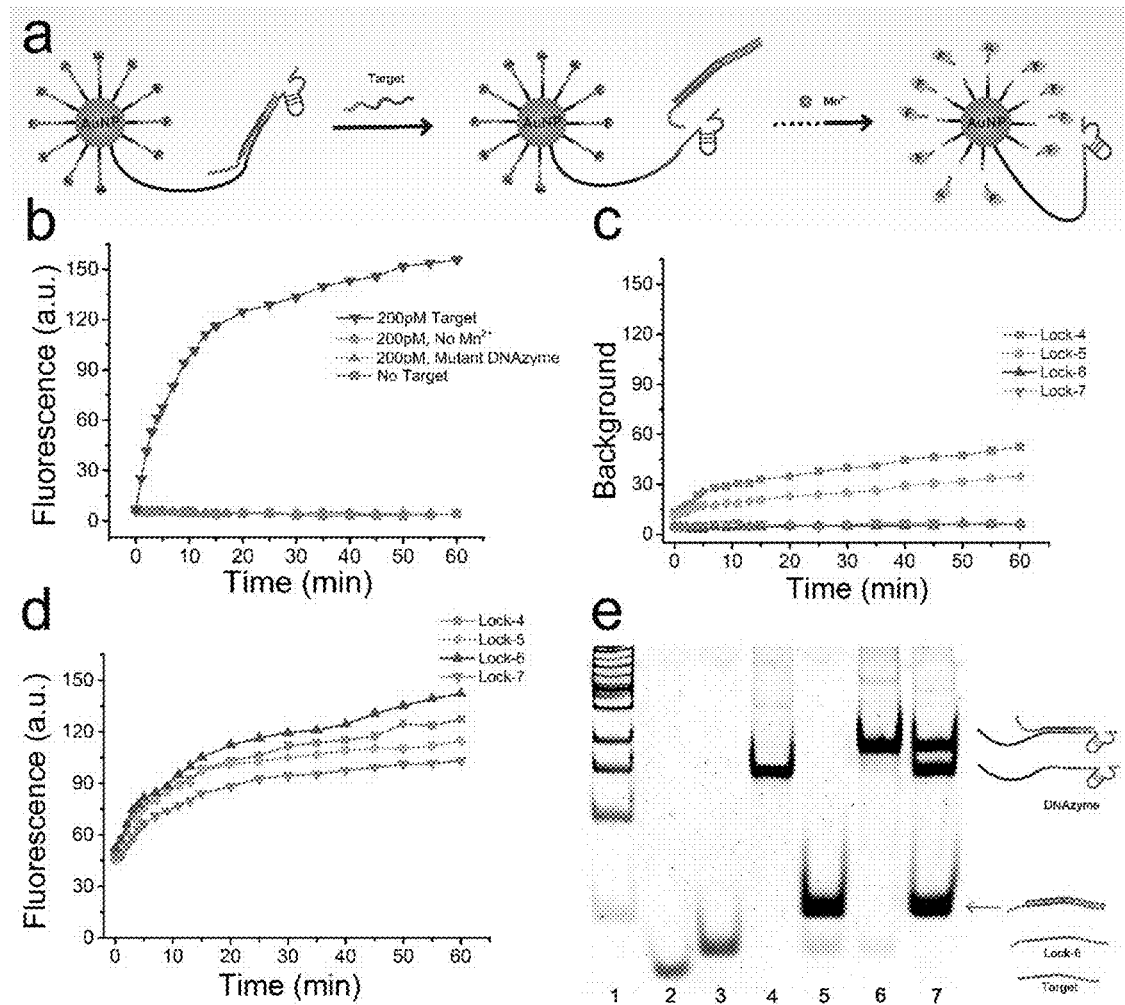
FIG. 2 depicts evaluation of a DNAzyme motor for its performance in solution. (Panel a) Operation of DNAzyme motor initiated by the specific nucleic acid target. (Panel b) Real-time monitoring of fluorescence generated by the DNAzyme motor in response to the target sequence and cofactor $Mn^{2+}$. The relative standard deviations (RSDs) from replicate experiments were 2.1-5.4%. (Panel c) Background fluorescence generated by four motors that vary by the locking strand. RSDs were 3.5-7.2%. (Panel d) Real-time monitoring of fluorescence generated by the four DNAzyme motors in response to 200 pM target sequence. RSDs were 4.1-8.3%. (Panel e) Gel images showing strand displacement of the DNAzyme strand by the target DNA, forming a duplex between the target and the locking strand. Lane 1: DNA ladder; lane 2: target DNA; lane 3: locking strand; lane 4: DNAzyme strand; lane 5: mixture of locking strand and target DNA at 1:1 molar ratio; lane 6: mixture of locking strand and DNAzyme strand at 1:1 molar ratio; lane 7: mixture of locking strand-DNAzyme strand complex and target DNA at 1.1:1 molar ratio. The strong band marked a red arrow corresponds to the hybrid between the locking strand and the target strand, resulting from the strand displacement reaction.

Before applying the DNAzyme motor to intracellular operation, we first optimized and evaluated the operation of the motor in the test tube (FIG. 2a). To facilitate the optimization and evaluation, we used a DNA strand with the same sequence as miR-10b to initiate the operation of the DNAzyme motor. FIG. 2b shows typical operating curves of the DNAzyme motor. In the absence of a target sequence, Arm 2 of the DNAzyme is sequestered by the locking strand and the DNAzyme motor is inactive, which is demonstrated by no observable fluorescence increase over the operating time. Upon addition of 200 pM target sequence, the target-triggered strand displacement exposes Arm 2 of the DNAzyme, thereby enabling the DNAzyme to hybridize to one substrate strand on the track. In the presence of cofactor $Mn^{2+}$, the DNAzyme is activated to cleave the substrate strand, initiating autonomous walking of the motor along AuNP. The continuous fluorescence increase over the 60 min operating time suggests the autonomous walking of the motor. When the cofactor is absent, no fluorescence increase is observed, confirming that the operation of the DNAzyme motor relies on both the specific target sequence and the cofactor for the DNAzyme.

Figure 11:
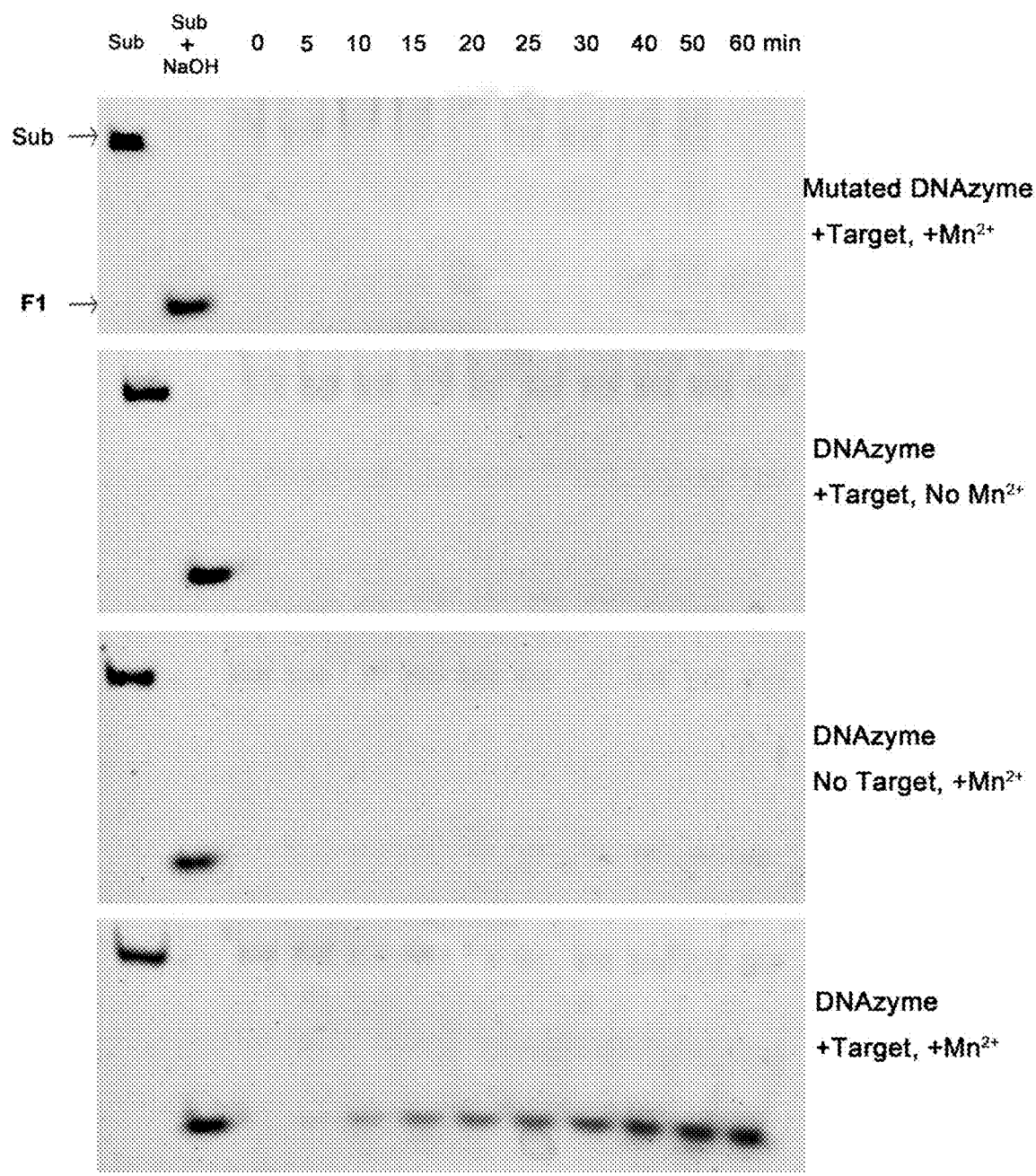
FIG. 11 depicts gel images showing the expected fluorescent substrate fragment (F1) cleaved by the DNAzyme motor (the bottom gel), no cleavage of the fluorescent substrate by a mutant DNAzyme motor (the top gel), and no cleavage of the fluorescent substrate by the DNAzyme motor in the absence of the target or the cofactor $Mn^{2+}$ (middle two gels). The DNAzyme or mutant DNAzyme motor system at a concentration equivalent to 7 nM AuNPs was mixed with 16 nM target DNA sequence in the autoclaved buffer (pH 8.0), containing 25 mM Tris-acetate and 200 mM NaCl. After incubation at room temperature for 20 min, 0.5 mM $Mn^{2+}$ was added. Following the addition of $Mn^{2+}$ (referred to as time 0), 5 µL of the reaction solution was sampled repeatedly, to which 5 µL of 50 mM EDTA was added to chelate the cofactor $Mn^{2+}$ and thus stop the catalytic reaction. The reaction solution was then analyzed by gel electrophoresis. The far left lane is from the full-length FAM-substrate in the autoclaved buffer. No cleavage product (F1) is detectable, suggesting that the substrate is stable. The second lane from left is the control showing the fluorescent substrate fragment (F1) obtained by hydrolysis of the single ribonucleotide bond of the substrate using 2 M NaOH.

To examine the function of the DNAzyme, we mutated two nucleotides (G to T) of its catalytic core and used this mutated DNAzyme sequence to construct a mutant DNAzyme motor system. No fluorescence increase was observed (FIG. 2b) from the incubation mixture of the mutant motor system, 200 pM target sequence, and 0.5 mM cofactor $Mn^{2+}$. These results further support that the fluorescence increase of the functional DNAzyme motor results from its selective response to the target sequence and rule out the possibility of target-independent substrate degradation (e.g. RNase cleavage). The fluorescence results are also consistent with results of gel electrophoresis (FIG. 11).

Figure 12:
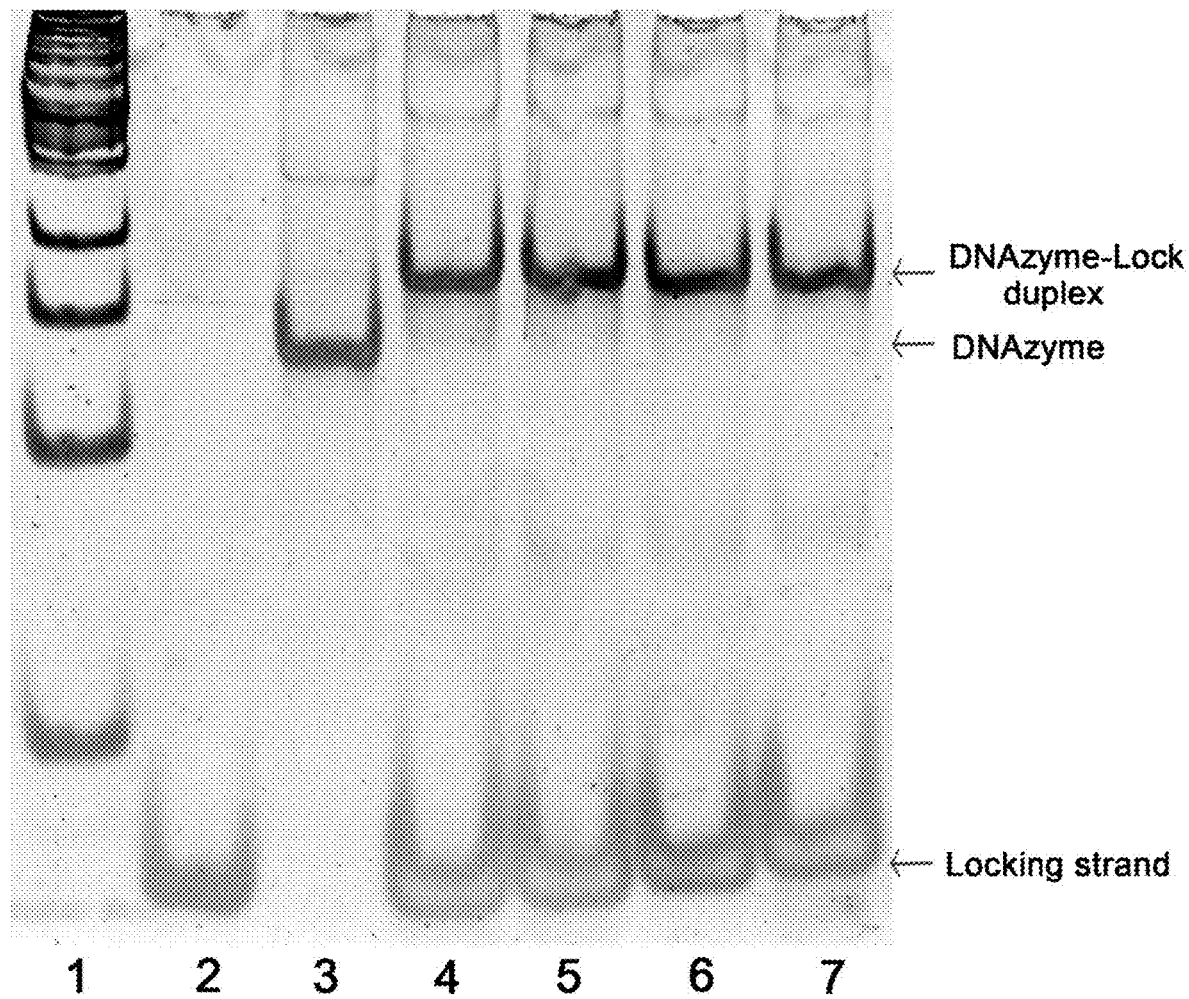
FIG. 12 depicts Gel images showing the formation of the duplexes between the DNAzyme strand and four different locking strands. Lane 1: DNA ladder from 25 nt to 766 nt; lane 2: Lock-4 (27 nt); lane 3: DNAzyme strand (85 nt); lane 4: mixture of the DNAzyme strand and Lock-4 at 1:3 molar ratio; lane 5: mixture of the DNAzyme strand and Lock-5 at 1:3 molar ratio; lane 6: mixture of the DNAzyme strand and Lock-6 at 1:3 molar ratio; lane 7: mixture of the DNAzyme strand and Lock-7 at 1:3 molar ratio. In lanes 4, 5, 6, and 7, the darkest band corresponds to the duplexes formed between the DNAzyme strand and the locking strand, Lock-4, Lock-5, Lock-6 and Lock-7, respectively. The lengths of Lock-4, Lock-5, Lock-6 and Lock-7 are 27 nt, 28 nt, 29 nt, and 30 nt, respectively. With the use of Lock-6 and Lock-7, no free DNAzyme is visible from the gel (lanes 6 and 7), suggesting complete formation of the duplexes between the DNAzyme and either Lock-6 or Lock-7.

The locking strand is used to silence DNAzyme and respond to target miRNA. An effective locking strand should completely sequester Arm 2 of the DNAzyme and efficiently expose it in response to the specific target. Incomplete sequestering of Arm 2 would result in unwanted target-independent operation of the DNAzyme motor, whereas ineffective exposing of Arm 2 by target miRNA would decrease the sensitivity of the motor. We designed four locking strands (Lock-4, 5, 6, and 7, Table 1) consisting of a conserved target-binding domain and a sequestering domain having different lengths: 4, 5, 6, and 7 nt, respectively. We used these four locking strands to construct the DNAzyme motor and compared their efficiencies of sequestering and target-response. Good efficiency of sequestering, as indicated by negligible background, is achieved using sequestering domains of 6 nt and 7 nt (FIG. 2c, FIG. 12). The efficiency in initiating operation of the DNAzyme motor, as indicated by the fluorescence intensity, is the highest using Lock-6 in the motor system (FIG. 2d). We then used gel electrophoresis to test the strand displacement efficiency of Lock-6 (FIG. 2e). In lane 7, the presence of a strong band corresponding to the hybrid of Lock-6 with the target sequence and the absence of a band corresponding to the single-stranded target sequence further support that the use of Lock-6 allows for complete displacement of the DNAzyme strand by the target sequence. To explain why Lock-6 is a better locking strand than Lock-6, we further estimated the Gibbs free energy (ΔG) of hybridization of Lock-6 and Lock-7 with the DNAzyme strand and target miRNA. The ΔG values of hybridization of Lock-6 and Lock-7 with the target miRNA are the same, −30.6 kcal/mol, whereas the ΔG values of hybridization of Lock-6 and Lock-7 with the DNAzyme strand are −27.1 kcal/mol and −28.7 kcal/mol, respectively. Thus, the ΔG of hybridization between Lock-7 and the target miRNA is slightly higher than that of hybridization between Lock-7 and the DNAzyme strand, consistent with the decreased strand displacement efficiency.

Figure 13:
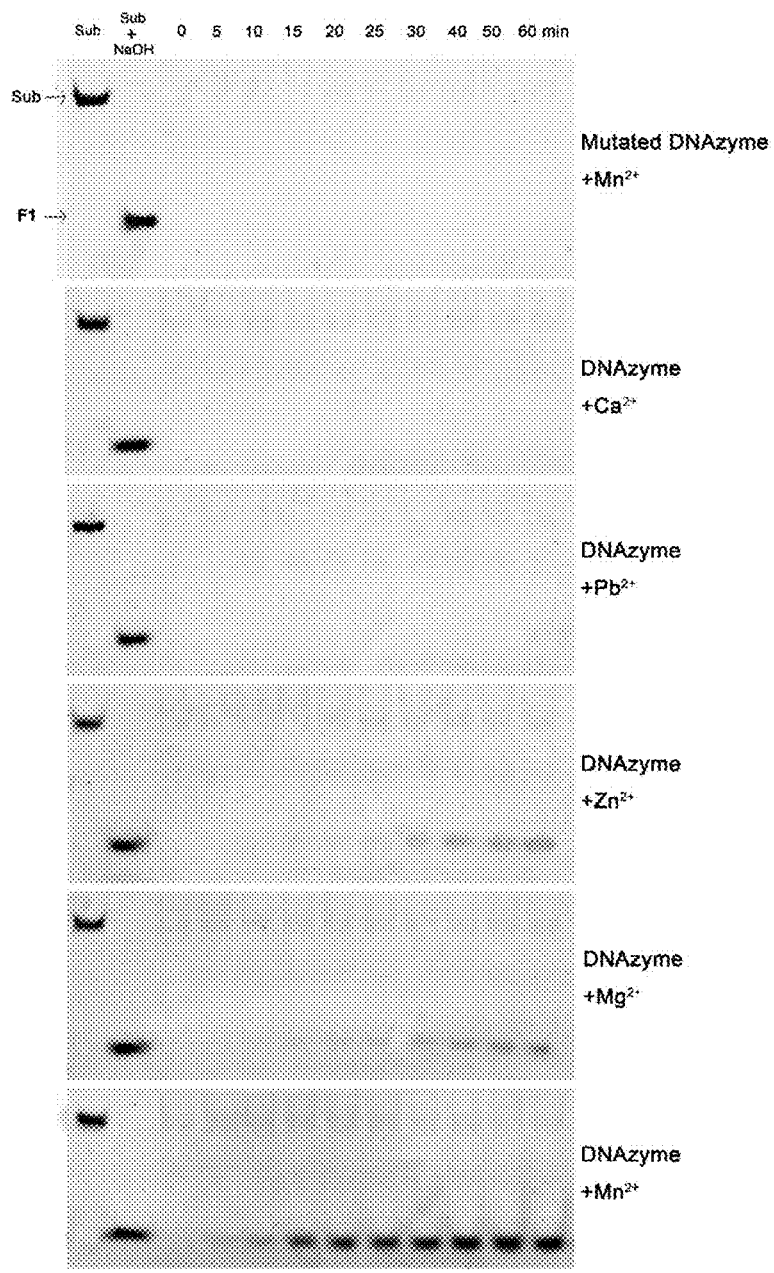
FIG. 13 Gel images showing the expected fluorescent substrate fragment (F1) cleaved by the DNAzyme motor in the presence of cofactor $Mn^{2+}$ (bottom gel), no cleavage of the fluorescent substrate by a mutated DNAzyme motor (top gel), and various degrees of cleavage of the fluorescent substrate by the DNAzyme motor in the presence of $Ca^{2+}$, $Pb^{2+}$, $Zn^{2+}$, or $Mg^{2+}$, as alternative cofactors. The DNAzyme or mutated DNAzyme motor system at a concentration equivalent to 7 nM AuNPs was mixed with 16 nM target DNA sequence in autoclaved buffer (pH 8.0), containing 25 mM Tris-acetate and 200 mM NaCl. After incubation at room temperature for 20 min, 0.5 mM $Mn^{2+}$, 10 mM $Ca^{2+}$, 0.2 mM $Pb^{2+}$, 0.01 mM $Zn^{2+}$, or 10 mM $Mg^{2+}$ was added. Following the addition of cofactor (referred to as time 0), 5 µL of the reaction solution was sampled repeatedly, to which 5 µL of 50 mM EDTA was added to chelate the cofactor ion and thus stop the catalytic reaction. The solution was then analyzed by gel electrophoresis. The far left lane is from the FAM-substrate in the autoclaved buffer. No cleavage product (F1) is detectable, suggesting that the substrate is stable. The second lane from left is the control showing the fluorescent substrate fragment (F1) obtained by hydrolysis of the ribonucleotide bond of the substrate using 2M NaOH.
Figure 14:
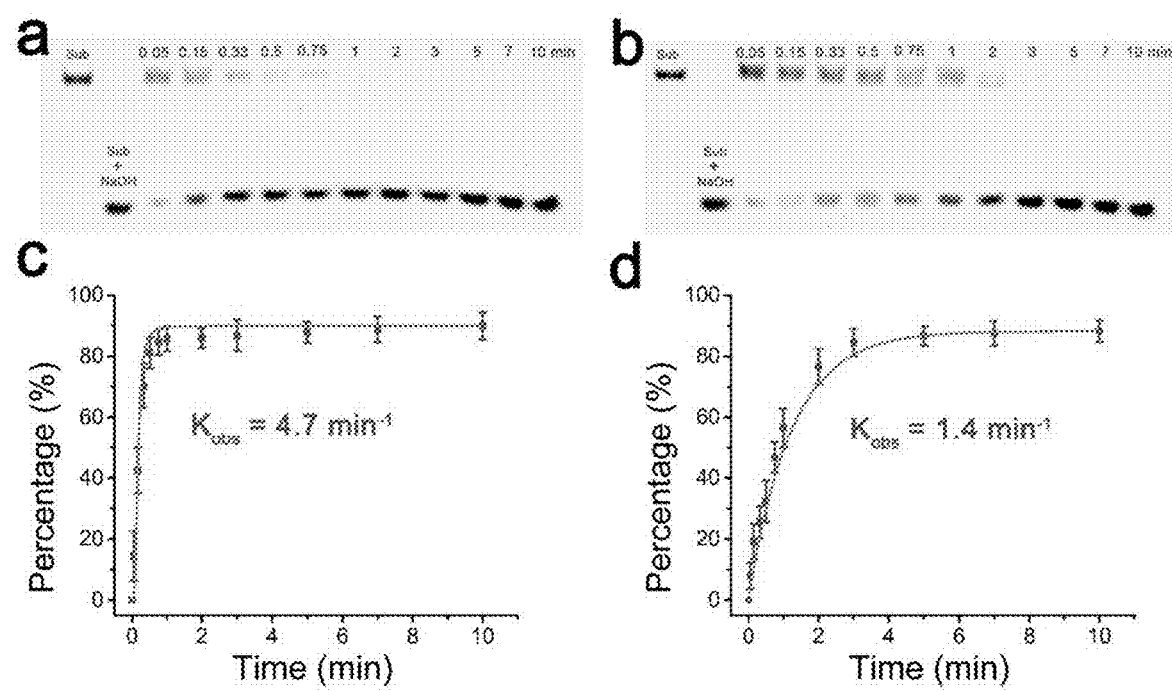
FIG. 14 depicts a comparison of single-turnover cleavage rate of the substrate by the DNAzyme motor tested using either $Mn^{2+}$ or $Mg^{2+}$ as the cofactor. (Panel a) Gel images showing the single-turnover cleavage of the substrate by the DNAzyme in the presence of 0.5 mM $Mn^{2+}$. (Panel b) Gel images showing the single-turnover cleavage of the substrate by the DNAzyme in the presence of 10 mM $Mg^{2+}$. (Panel c) Curve fitting showing a single-turnover cleavage rate ($K_{obs}$) of 4.7 $min^{-1}$ for the DNAzyme with 0.5 mM $Mn^{2+}$ as the cofactor. (Panel d) Curve fitting showing a single-turnover cleavage rate ($K_{obs}$) of 1.4 $min^{-1}$ for the DNAzyme with 10 mM $Mg^{2+}$ as the cofactor. 10 µM of the free control DNAzyme (sequence in Table S1, containing an 8-nt Arm 1 and an 8-nt Arm 2) was mixed with 1 µM FAM-labeled substrate autoclaved buffer (pH 8.0) containing 25 mM Tris-acetate and 200 mM NaCl. After incubation for 10 min, 0.5 mM $Mn^{2+}$ or 10 mM $Mg^{2+}$ was added to initiate the catalytic cleavage of the substrate by the DNAzyme. From 0.05 min to 10 min following the addition of either $Mn^{2+}$ or $Mg^{2+}$, 10 µL of reaction solution was sampled, to which 10 µL of 50 mM EDTA and 8 M urea was added. The solution was subjected to PAGE analysis. Intensity of the bands in the gel images was measured using ImageJ 1.47. The sum of the intensity of the substrate band and the product band in the first lane at 0.05 min was used to represent the total amount of the fluorescent substrate and product, serving as the denominator in the calculation of the percentage cleaved. The intensity of the cleaved product band in each lane from 0.05 to 10 min was used as the numerator in the calculation of the percentage cleaved. In the gel images of (Panel a) and (Panel b), the far left lane is from the FAM-substrate in the autoclaved buffer. No cleavage product is detectable, suggesting that the substrate is stable in the autoclaved buffer. The second lane from left is the control showing the fluorescent substrate fragment (F1) obtained by hydrolysis of the ribonucleotide bond of the substrate using 2M NaOH.

The metal cofactors are usually required to achieve the catalytic activity of the DNAzyme[37, 38]. We tested the operation of the DNAzyme motor in response to 200 pM target sequence and different divalent metal ions. Although $Pb^{2+}$ is the most effective cofactor for the original 8-17E DNAzyme, we found that $Mn^{2+}$ was the best cofactor for the truncated form of the DNAzyme. (Arm 1 and Arm 2 of the original 8-17E DNAzyme were truncated from 9 nt to 5 nt and 7 nt, respectively). The multiple turnover cleavage rate Kobs follows the order of $Mn^{2+}>Mg^{2+}>Zn^{2+}>Pb^{2+}>Ca^{2+}$ (FIG. 3a), which is consistent with results of gel electrophoresis (FIG. 13). We further compare single turnover cleavage rates of DNAzyme when using $Mn^{2+}$ and $Mg^{2+}$ as the cofactor. Similarly, $Mn^{2+}$ led to a stronger catalytic activity than $Mg^{2+}$ (FIG. 14a-14d). We then examined the effect of $Mn^{2+}$ concentration on the operation of the DNAzyme motor. The DNAzyme motor operates reliably in the presence of 250 μM to 2000 μM $Mn^{2+}$ (FIG. 3b, FIGS. 15 and 16). Therefore, intracellular operation of the DNAzyme motor is feasible because cellular uptake of hundreds of μM $Mn^{2+}$ does not impact the viability of cells[39]. We also tested the operation of the DNAzyme motor under different pH conditions. The motor showed reliable performance in the pH range from 7.0 to 9.0 (FIG. 17).

Figure 4:
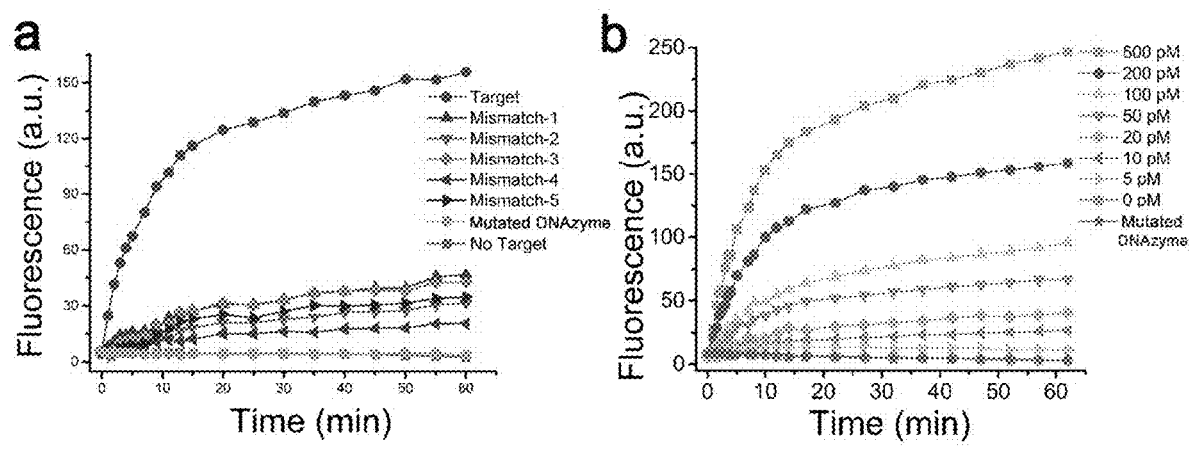
FIG. 4 depicts real-time monitoring of fluorescence generated by DNAzyme motors responding to the target DNA sequence or mismatch DNA sequences (Panel a) and to a target miRNA sequence of varying concentrations (Panel b). (Panel a) Operating curves of the DNAzyme motor tested with the target DNA sequence and five variants of single-base mismatch. Relative standard deviations were 1.4-7.6%. (Panel b) Operating curves of the DNAzyme motor in response to varying concentrations (0-500 pM) of the target miRNA. Relative standard deviations were 1.1-9.3%.
Figure 5:
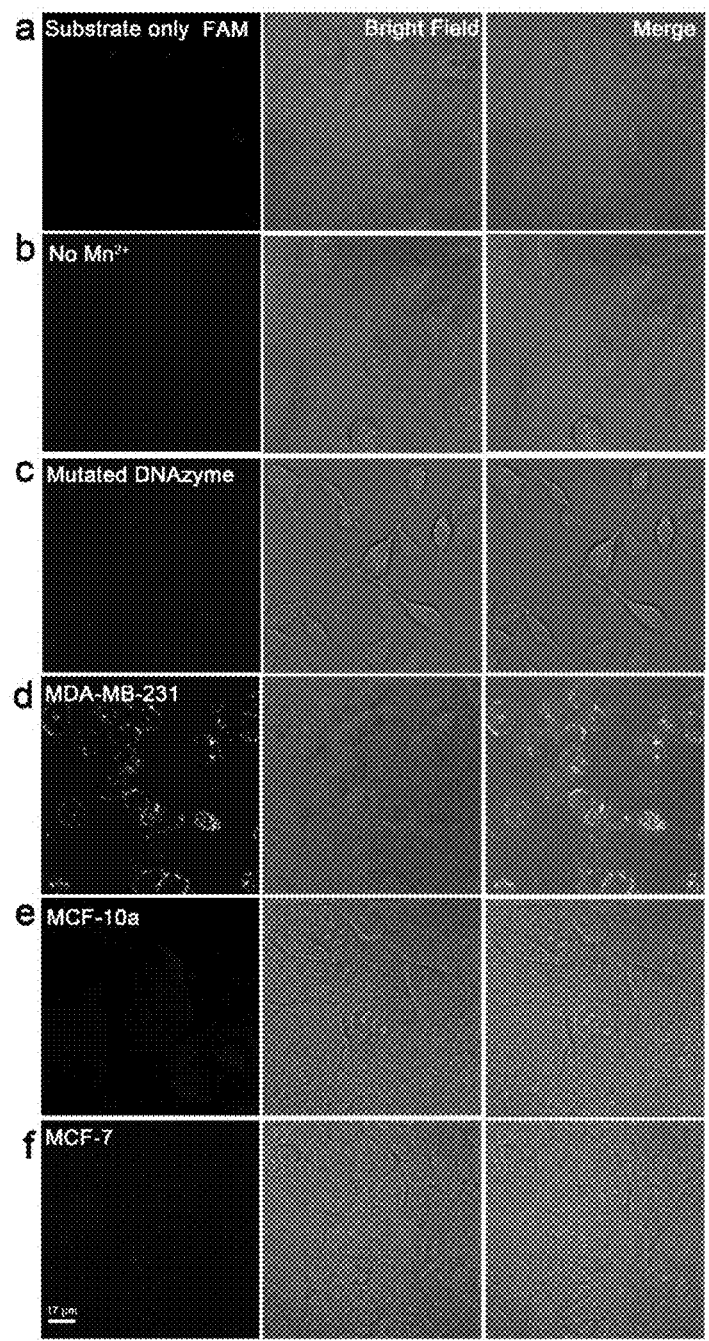
FIG. 5 depicts Imaging of live cells after uptake of a DNAzyme motor system that was designed to be initiated by a specific microRNA (miR-10b). (Panel a) Images showing MDA-MB-231 cells after incubation with AuNPs functionalized with the substrate strand but not the DNAzyme strand (negative control). (Panel b) Images showing MDA-MB-231 cells after incubation with the DNAzyme motor system but not subsequently treated with the cofactor $Mn^{2+}$ (negative control). (Panel c) Images showing the target MDA-MB-231 cancer cells after incubation with a mutant DNAzyme motor system and the subsequent treatment with the cofactor $Mn^{2+}$ (negative control). (Panel d) Images showing the target MDA-MB-231 cancer cells after incubation with the DNAzyme motor system and the subsequent treatment with the cofactor $Mn^{2+}$. Fluorescence images of the target cells are the result of intracellular operation of the DNAzyme motor. (Panel e) Images showing the negative control MCF-10a cells after the same treatment as for the MDA-MB-231 cells in (Panel d). (Panel f) Images showing the negative control MCF-7 cells after the same treatment as for the MDA-MB-231 cells in (Panel d). All images were collected at the end of 60 min operation time (i.e., 60 min after the addition of the cofactor $Mn^{2+}$).

We examined the specificity of the DNAzyme motor by using five variants of single-base mismatch to initiate the operation of the motor. These five variants were designed to have the mismatch base at different representative sites (Table 1). The fluorescence increase resulting from 200 pM target sequence is significantly larger than those increases from the five variants at the same concentration (FIG. 4a), which indicates that far fewer motors are initiated by the mismatch variants. Thus, the DNAzyme motor can effectively differentiate the fully matched target from these variants of single-base mismatch. The selection factor ranges from 5.1 to 16.7 depending on the mismatch site (Table 2). The high specificity of the DNAzyme motor is attributed to the design of the locking strand that contains a sequestering domain in addition to the target-binding domain[40]. The Lock-6 has a 7-nt toehold to ensure highly efficient strand displacement and a 6-nt sequestering domain that is first bound and then exposed after the strand displacement reaction, reducing the ΔG of the reaction and thereby improving the specificity. The ΔG of hybridization between Lock-6 and the target miRNA is −30.6 kcal/mol, and that between Lock-6 and the DNAzyme strand is −27.1 kcal/mol. Thus, the ΔG of strand displacement reaction is only −3.5 kcal/mol, leading to the high specificity of the reaction (FIG. 18).

TABLE 2

Selection factor of the DNAzyme motor for five variants of single-base mismatch.

| Mismatch variants | 1 | 2 | 3 | 4 | 5 |
|---|---|---|---|---|---|
| Selection factor | 5.1 | 8.8 | 5.2 | 16.7 | 6.8 |

The selection factor was calculated by using the following equation:

$$\text{Selection factor} = \frac{F_{[Target]} - F_{[Control]}}{F_{[Mismatch]} - F_{[Control]}}$$

Having optimized the operating conditions of the DNAzyme motor responding to the DNA target, we further examined the operation of the DNAzyme motor in response to various concentrations of the target miRNA. We added different concentrations of the target miRNA into motor solutions each containing equivalent 230 pM AuNP. We incubated the solutions for 20 min to ensure the complete strand displacement reaction. We then added 500 μM $Mn^{2+}$ into the solutions to activate the DNAzyme. As expected, higher concentrations of the target miRNA led to larger fluorescence increases (FIG. 4b), consistent with more DNAzyme motors being initiated by the higher concentrations of the target miRNA. A linear relationship was observed between fluorescence intensity and target miRNA concentration from 5 to 200 pM (FIG. 19). The operation of the motor initiated by 1 pM target can generate a fluorescence increase distinguishable from blank, indicating the high sensitivity of the motor. The motor responds similarly to both the target miRNA (FIG. 4b and FIG. 19) and DNA (FIGS. 20a and 20b).

We have determined that on average approximately 12 locked DNAzyme motors were conjugated on each AuNP. With a concentration of 230 pM AuNPs used in the operation, the total number of the DNAzyme motors are in large excess over the target miRNA when the concentrations of miRNA are lower than that of AuNPs, Therefore, only one (or none) of the DNAzyme motors on each AuNP is activated by the target miRNA. We reason that these activated DNAzyme motors operate similarly and independently. To test this, we monitored the operating curves resulting from 50, 100, and 200 pM target miRNA (FIG. 21). The operation of individual DNAzyme motors follows a similar profile for three target miRNA concentrations. We further calculated the walking steps of individual DNAzyme, and our results indicate that a single DNAzyme motor walks about 30 steps within 30 min (FIG. 21).

To trace the operation of the DNAzyme motor on individual AuNPs, we designed an alternative system that enables each walking step of the motor to turn on the fluorescence of a Cy5 molecule on the AuNP (FIG. 22). We designed the substrate strand to have a hairpin structure with a long single-stranded overhang that hybridizes to a Cy5-labeled DNA strand. The end of the substrate strand without the overhang is labeled with a black hole quencher so that hybridization of the substrate strand to the Cy5-labeled strand quenches the fluorescence of Cy5. We conjugated onto each AuNP dozens of locked DNAzyme strands and hundreds of Cy5-labeled strands to which the hairpin substrates are hybridized. In the presence of the target miRNA, the locked DNAzyme is activated to cleave the substrate at the single-ribonucleotide junction in the hairpin loop. The cleavage disrupts the hairpin structure and releases a quencher-containing fragment from the AuNP, restoring the fluorescence of the Cy5 molecule. The DNAzyme dissociates from the cleaved substrate and hybridizes to the next substrate, achieving the walking of the DNAzyme motor from one substrate strand to the next. Each walking step restores the fluorescence of a Cy5 molecule that remains attached to the AuNP. Our results (FIG. 23a) indeed show that the fluorescence of Cy5 from individual AuNPs increases over time, representing the stepwise walking of the DNAzyme motor on the AuNP and the corresponding catalytic cleavage of the quencher-labeled substrate. In the absence of the target miRNA, there is very little fluorescence background (FIG. 23b), consistent with the fact that the DNAzyme motor is inactive.

Intracellular Operation of the DNAzyme Motor

Having constructed the DNAzyme motor and optimized its operation in the buffer solution, we then applied the motor to its operation in living cells (FIG. 5a-f). We used the MDA-MB-231 cell line, derived from human breast adenocarcinoma cells, to test the intracellular operation of the DNAzyme motor. The target miRNA miR-10b is present in this cell line at a very low concentration and it would be difficult to image it using other methods[41-43]. We functionalized the DNAzyme motor and its track on AuNPs, which facilitates the cellular uptake of the motor system. Previous studies have demonstrated that DNA-functionalized AuNPs can be efficiently taken up by cells without the need for transfection reagents[44-46]. We determined the cellular uptake of the DNAzyme motor system by measuring the concentration of Au inside cells by using inductively coupled plasma mass spectrometry (ICP-MS) (FIG. 31). The measured amount of Au, equivalent to the number of DNAzyme motors in the cells, increases with increase in concentration and time of incubation (FIG. 24a-b). When 0.2 nM AuNP and 2 h incubation were used, each cell took up about $3.2 \times 10^4$ AuNPs, which is approximately equivalent to 13 nM AuNP in the cell.

Inside the cells, the specific miR-10b miRNA hybridizes to the locking strand of the motor system through the strand displacement reaction, exposing the sequestered Arm 2 of the DNAzyme motor and freeing the DNAzyme to interact with a substrate strand. Further treatment of the cells with 5 mM $MnCl_2$ initiated the DNAzyme motor to walk along the AuNP autonomously and processively. Each walking step restores the fluorescence of one FAM molecule, which can be used for imaging the operation of the motor. After 60 min operation, the fluorescence is detectable from the MDA-MB-231 cancer cells (FIG. 5d), suggesting that the intracellular operation of the DNAzyme motor is accomplished. These cells show various fluorescence intensities, suggesting that the intracellular miR-10b levels are different among these cells. When cells were not treated with $Mn^{2+}$ solution, no fluorescence was observed (FIG. 5b), confirming that the operation of the DNAzyme motor requires both the target miRNA and the cofactor. This control experiment also suggests that the substrate strand on the AuNPs is stable and is not released without the active operation of the DNAzyme motor. We also tested the mutant DNAzyme motor incubated with the target MDA-MB-231 cells. As expected, no fluorescence was observed (FIG. 5c), proving the high stability of the substrate strand on AuNPs in the absence of an active DNAzyme motor. We further tested another control, using AuNPs conjugated with the substrate strands but not with the DNAzyme. No fluorescence is observed (FIG. 5a), further proving that substrate strands on the AuNP are stable within the cells. To examine whether the operation of the DNAzyme is responsive to the specific miRNA, we introduced the motor system into two control cells deficient in miR-10b, MCF-10a and MCF-7 cells[41]. After 60 min incubation, little fluorescence is observed from these two cells (FIGS. 5e and 5f), proving the specificity of the DNAzyme motor for the specific target.

$Mn^{2+}$ is required to achieve operation of the DNAzyme motor. Although native cellular $Mn^{2+}$ levels are not sufficient to activate the DNAzyme motor, the levels of $Mn^{2+}$ required can be readily taken up by cells through simple incubation of the cells with $Mn^{2+}$ solution.[39] We tested the intracellular operation of the DNAzyme motor by treating cells with different concentrations of $Mn^{2+}$, 1, 5, and 10 mM. Similar fluorescence intensities were obtained, suggesting that the DNAzyme motor operates in a similar manner for these three cases (FIG. 25). The reliable operation of the DNAzyme motor within a wide range of $Mn^{2+}$ concentrations make intracellular operation of the motor practical.

Figure 6:
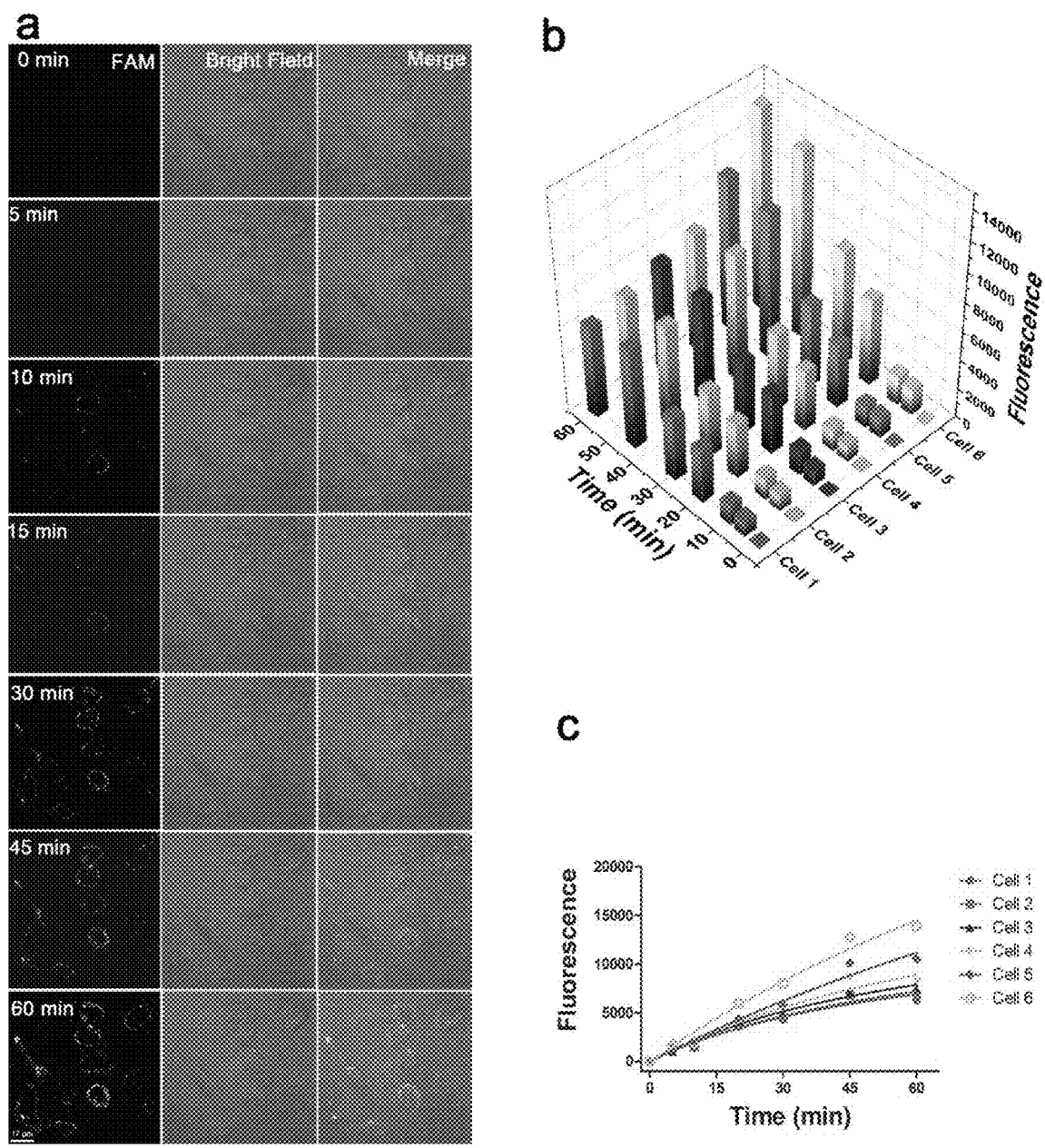
FIG. 6 depicts images and fluorescence intensity of MDA-MB-231 cancer cells following intracellular operation of the DNAzyme motor. The DNAzyme motor was designed to respond to the intracellular microRNA miR-10b. (Panel a) Images of MDA-MB-231 cancer cells after intracellular operation of the DNAzyme motor for 0, 10, 30 and 60 min. 0 min refers to the time point when $Mn^{2+}$ is added into the operating buffer. LMM5 laser transmission setting was 85 and the laser excitation time was 185 ms for each image. (Panel b) and (Panel c) Fluorescence intensity of six cells over the 60 min operation time of the DNAzyme motor. The fluorescence intensity was measured using ImageJ 1.47.

To examine the autonomy and processivity of the motor walking, we imaged cellular fluorescence at different time points of the 60 min operation (FIG. 6a-c). The fluorescence increases steadily for all cells over the operating time, indicating that the DNAzyme motor walks along AuNP autonomously and processively in living cells (FIG. 6, FIG. 26). We further quantified the fluorescence increase in individual cells (FIG. 6c). The different slopes of the fluorescence increase imply that the target miRNA is present at different levels in these cells. This target-initiated operation of the motor can be used for in situ amplified detection of target miRNA in living cells. No fluorescence was observed from the target cells (FIG. 27) when the DNAzyme motor system was constructed with the mutant DNAzyme.

We further detected fluorescence of the target MDA-MB-231 cells after the cells were incubated with either the functional DNAzyme motor system (FIG. 28a) or the mutant DNAzyme motor system (FIG. 28b) for 1 h, 3 h, and 5 h. Cells treated with the functional DNAzyme motor system showed fluorescence throughout the 5 hour period (FIG. 28a). The slight decrease in fluorescence intensity over the longer time could be due to fluorescence bleaching. Non-detectable fluorescence from the cells treated with the mutant DNAzyme motor system throughout the 5 hour period (FIG. 28b) indicates negligible release of the fluorescent substrate from the AuNPs, i.e., good stability of the DNAzyme motor system in the target cells.

Figure 7:
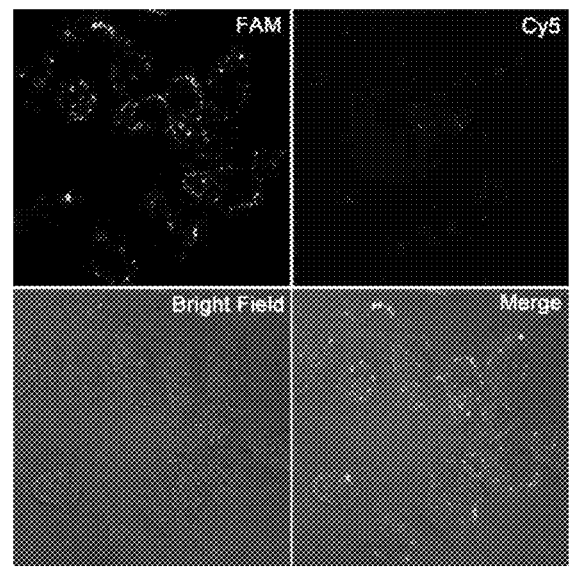
FIG. 7 depicts images of MDA-MB-231 cancer cells obtained from the fluorescence detection of FAM and Cy5 after intracellular operation of the DNAzyme motor. The higher intensity from FAM is due to the autonomous walking of the DNAzyme motor, with each walking step restoring fluorescence of a FAM molecule. Therefore the DNAzyme motor results in the amplified imaging of the intracellular miRNA target. The Cy5 image is much weaker because there is no amplification involved.

In addition to accomplishing autonomous operation and amplified detection of the target miRNA in living cells, the DNAzyme motor system enables fluorescence determination of the cellular location of the target miRNA. The target miRNA displaces the DNAzyme strand to form a duplex with the locking strand (FIG. 10). The fluorescence of the Cy5 molecule in the duplex is then restored and can be used to indicate the location of the target miRNA. We imaged fluorescence of both Cy5 and FAM in the cells (FIG. 7). Fluorescence intensity from the Cy5 image is much weaker than fluorescence intensity from the FAM image at the end of 60 min operation. This is consistent with the fact that the DNAzyme motor amplifies the signals for imaging, because the DNAzyme motor generates multiple FAM-labeled F1 molecules (~30) in response to a single target miRNA strand.

Figure 8:
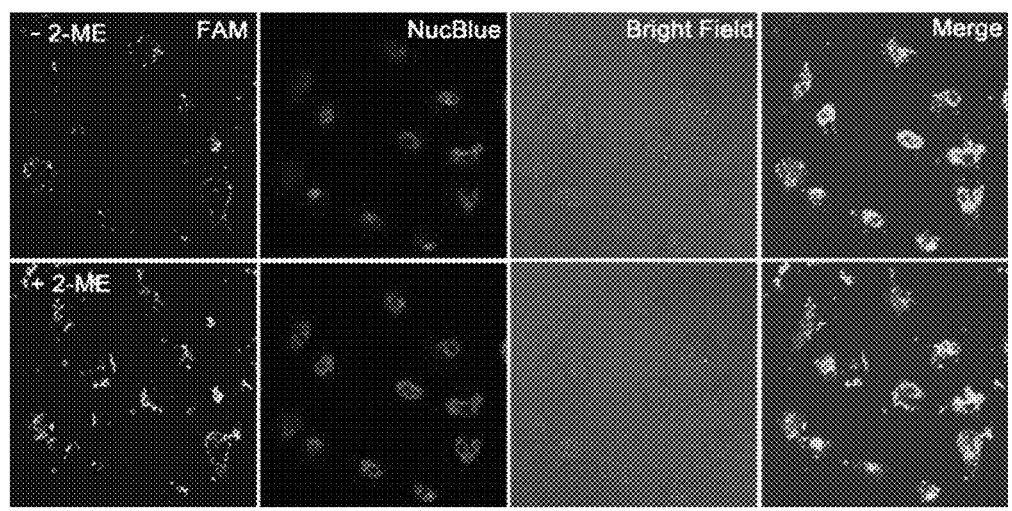
FIG. 8 depicts Images of MDA-MB-231 cancer cells after intracellular operation of the DNAzyme motor for 60 min (top images) followed by additional treatment with 10 mM 2-mercaptoethanol (2-ME) (bottom images). 4',6-diamidino-2-phenylindole (DAPI) was used to stain the nucleus of the cells.

We also determined the relative amount of substrate strands that were cleaved in response to the DNAzyme motor operation (FIG. 8). For comparison, we subsequently treated cells with 10 mM 2-mercaptoethanol to release all remaining substrate strands from AuNPs, and then imaged the total FAM fluorescence. These results indicate that on average 22% of the total substrate strands on the AuNP are cleaved as a result of the DNAzyme motor action.

Discussion

We demonstrate, for the first time, the accomplishment of operation of a synthetic DNA motor in living cells. This DNAyzme motor system has several important features desirable for intracellular operation and characterization. First, the entire motor system is a functionalized AuNP that is decorated with both the DNA motor and its track. The integration of the motor and its track on a single AuNP facilitates the cellular uptake of the motor system. DNA-functionalized AuNPs can be efficiently taken up by cells without the need for transfection reagents that would usually be required for cellular uptake of DNA strands[47]. Additionally, previous studies have shown that AuNPs similar to the concentration as we used had little effect on the cytotoxicity and viability of cells[48, 49]. Second, the motor is self-powered, enabling autonomous motion without the need for adding fuel DNA strands and/or protein enzymes. This is of great importance for intracellular operation because the external addition of fuel DNA strands and/or protein enzymes is not practical. Third, the intracellular operation of the motor is initiated by the specific cellular target, e.g., miRNA. Outside the cells, the DNAzyme motor is silenced by a purposely designed locking strand. But once inside the cells, the specific cellular miRNA hybridizes to the locking strand, initiating the operation of the motor. The motor system is highly specific, enabling differentiation of the fully matching target from various sequences containing a single-base mismatch at different sites. Fourth, the motor operates reliably under physiological pH conditions and reasonable cofactor concentrations, which enables meaningful applications to live cells. Furthermore, 30 walking steps of the motor can be accomplished within 30 min. This high walking speed of the motor is achieved by the rational control of the arm length of the DNAzyme and by the construction of high-density tracks on AuNP. Finally, the result of the intracellular operation of the motor can be monitored in real-time by using fluorescence imaging. Each walking step of the motor restores the fluorescence of a previously quenched FAM molecule, enabling real-time imaging of the progression of the motor. Importantly, the motor system enables amplified detection of specific miRNA in living cells. The operation of the motor can release many FAM-containing F1 strands from AuNP in response to a single miRNA target. Furthermore, labeling of the locking strand with a second fluorophore, Cy5, allows the motor system to signal the location of the target miRNA.

Each walking step involves three actions, hybridization of the DNAzyme to one substrate strand to form a DNAzyme-substrate complex, cleavage of the substrate strand to create a DNAzyme-product complex, and release of the DNAzyme from cleavage products to regenerate the free DNAzyme[50]. The cleavage of the substrate is not the rate-determining step because the single-turnover cleavage rate (4.7 $min^{-1}$) is higher than the multiple-turnover cleavage rate (3.1 $min^{-1}$) of the first 5 min operation and much higher than the cleavage rate of the subsequent operation time. The cleavage products, F1 and F2, are constant for all walking steps, thus the release rate of DNAzyme from cleavage products is also constant. However, the walking speed of the motor various over time, faster in the first 10 min and slower afterwards. This mainly results from the varying hybridization rate of the DNAzyme to the substrate strand. In the initial stage of walking, many substrate strands are near the conjugation site of the DNAzyme strand. Therefore, hybridization of the DNAzyme to the substrate strands is fast, leading to a high walking speed. As the nearby substrates are cleaved, the hybridization of the DNAzyme to the substrate becomes slower because the hybridization requires stretching of the spacer S2 to access the distant substrate strands. Finally, no substrate strand is accessible to the DNAzyme; and the walking of the motor stops. We compared the walking of the miRNA-initiated DNAzyme motor and a control DNAzyme motor that is not conjugated to AuNP (FIG. 29*a-c*). The miRNA-initiated motor has an initial faster response to the target (FIG. 29*c*) and then slowed and finally stopped after 3 h. The free control DNAzyme has a constant speed over the 6 h operation (FIG. 29*c*) because in the absence of the spacer S2, the hybridization rate of the control motor to the substrate remains constant. The initial walking speed of the miRNA-initiated motor is significantly higher than that of the control motor because the walking of the control motor from the cleaved substrate to the next substrate involves a strand displacement reaction, slowing the walking speed.

The response of the DNAzyme motor is not limited to the miR-10b miRNA. Similar motor systems can be readily constructed to respond to other miRNA and messenger RNA targets. A modification to the design is by simply altering the target binding domain of the locking strand. Diverse DNAzyme motors can also be designed to respond to small molecules and proteins in cells. A strategy may involve adapting aptamers into the locking strand. In addition, by incorporating functional molecules (e.g., therapeutic molecules and antisense strands) into the substrate strands, the DNAzyme motor system can be further used for target-triggered drug release and modulation of cellular activity. Applications of the DNAzyme motor strategy, such as sensing intracellular molecules, imaging live cells, regulating cellular functions, and facilitating drug delivery, may be achieved.

Methods

Construction of the miRNA-Initiated DNAzyme Motor System.

The DNAzyme motors were constructed on 20-nm AuNPs by functionalizing the AuNPs with the pre-blocked DNAzyme and its substrate. The sequences of the DNAzyme, substrate, and locking strand are summarized in Table 1, with complementary sequences showing in identical matching colors. The DNAzyme strand and the substrate strand that require direct conjugation to the AuNPs were thiolated. Prior to conjugation to the AuNPs, the DNAzyme was blocked (silenced) by using a locking strand. For the preparation of the blocked DNAzyme strand, the locking strand and the DNAzyme strand in a molar ratio of 3:1 was mixed in 1×PBS buffer (pH 7.4). The use of three-time molar excess of the blocking strand was to ensure the complete blocking of the DNAzyme strand by the locking strand. The mixture was heated to 75° C. and gradually cooled to 4° C. at a rate of 1.2° C./min. The blocked DNAzyme strand and the substrate strand were then conjugated to the AuNPs. For the purpose of controlling the ratio of the DNAzyme and the substrate on the AuNPs, AuNPs (20 nm diameter), the blocked DNAzyme strand, and the FAM-labeled substrate strand were mixed at a molar ratio of 1:50:1000. This solution was incubated at room temperature for 12 h. Tween 20 (1%) was then added to make the final solution containing 0.05% Tween 20. The use of Tween 20 was to reduce adsorption and aggregation of AuNPs. To enhance the DNA loading amounts, NaCl was added in increments of 0.05 M for the first two times and thereafter in the increment of 0.1 M for six more times. After each addition of NaCl, the solution was sonicated for 1 min followed by incubation for 40 min at room temperature. After incubation at room temperature for an additional 24 h, the solution was centrifuged at 16,000 g for 20 min to separate the AuNPs from the unconjugated DNA. The AuNPs were washed four times using 1 mL of Tris-HCl (pH 7.4) containing 0.05% Tween 20. The AuNPs were resuspended in 25 mM Tris-HCl (pH 7.4) at a concentration of 2.3 nM, and stored at 4° C. until use.

Determination of the Number of Substrate Molecules per AuNP.

For the purpose of determining the average number of the substrate molecules on each AuNP, the conjugated substrate strands were first released from the AuNPs using 2-mercaptoethanol. The solution was then centrifuged to precipitate the AuNPs, and the supernatant containing the released substrate strands was measured by fluorescence. Specifically, 10 μL of 2.3 nM AuNP solution was mixed with 10 μL of 35 mM 2-mercaptoethanol and the mixture was then diluted to 100 μL by using 1×PBS buffer. The mixture was placed in the dark. After an overnight incubation at room temperature, the solution was centrifuged at 16,000 g for 10 min to precipitate AuNPs. A 95-μL supernatant was transferred onto a 96-well plate (Fisher Scientific, Ottawa, ON), which was then loaded onto a fluorescence microplate reader (Beckman Coulter, DTX 800) for fluorescence detection. Molar concentrations of the substrate were determined against a calibration of the FAM-labeled substrate strand.

The average number of substrates per AuNP was then derived from the concentrations of AuNPs and substrate. Our results show that on average, 232 substrate molecules were conjugated to each AuNP. On the basis of a molar ratio of 1:20 for the DNAzyme strand and the substrate strand used together in the conjugation reaction, approximately 12 DNAzyme molecules were conjugated to each AuNP. Thus, the densities of the substrate and DNAzyme strands are $1.85 \times 10^{-1}/nm^2$ and $9.24 \times 10^{-3}/nm^2$ on the 20-nm AuNPs.

Examination of Blocking Efficiency of the DNAzyme Strand

The blocking efficiency of the DNAzyme strand by the locking strand was examined by using native polyacrylamide gel electrophoresis (PAGE) (FIG. 12). Three microliters of 10 µM DNAzyme strand and 9 µL of 10 µM locking strand were mixed and 18 µL of 1×PBS was then added to make a total volume of 30 µL. The mixture was then heated to 75° C. by using a Bio-Rad thermal cycler (Bio-Rad, Hercules, Calif.) and cooled down to 4° C. at a rate of 1.2° C./min. PAGE on 10% polyacrylamide gel was used to separate the blocked DNAzyme strand from the excess locking strand. Electrophoresis was carried out at 80 V for 90 min. After separation, the gel was stained with ethidium bromide for 30 min and imaged by a fluorescence gel imaging system (ImageQuant LAS 4000, GE Healthcare Life Sciences, Pittsburgh, Pa.).

Examination of Strand Displacement Efficiency of the DNAzyme Strand by the Target Sequence The strand displacement efficiency of the DNAzyme strand by the target sequence was examined by using native PAGE. Three microliters of 10 µM DNAzyme strand and 3 µL of 10 µM locking strand were mixed and annealed by using the temperature program as described above. After the DNAzyme strand was bound by the locking strand, 2.7 µL of 10 µM target sequence was added and 1×PBS buffer was used to make a final volume of 30 µL. After incubation at room temperature for 30 min to ensure the completion of the strand displacement reaction, 5 µL of the solution was mixed with 5 µL 2×loading buffer, and then loaded onto 10% polyacrylamide gel for separation.

Determination of Single-Turnover Cleavage Rate of the DNAzyme

To determine the single-turnover cleavage rate of the DNAzyme (FIG. 14a-d), the full-length DNAzyme (containing a 8-nt Arm 1 and a 8-nt Arm 2) was used to ensure the formation of a stable DNAzyme-substrate complex. One hundred and ninety microliters of a mixture was prepared to contain the DNAzyme and FAM-labeled substrate strand at a molar ratio of 1:1.5 in 25 mM Tris-acetate (8.0) and 200 mM NaCl. The use of 1.5 molar excess DNAzyme was to ensure the complete hybridization of the substrate strand to the DNAzyme. After incubation for 30 min, 10 µL of 200 mM $Mg^{2+}$ or 10 mM $Mn^{2+}$ was added to initiate the DNAzyme-catalyzed cleavage. At designated time points, 10 µL aliquot of reaction solution was sampled and quenched by using 10 µL of 50 mM EDTA and 8 M urea. Reaction solutions were loaded onto 14% denaturing polyacrylamide gel for separation. Electrophoresis was carried out at 80 V for 80 min in a water bath set at 50° C.

Comparison of DNAzymes for Construction of the DNAzyme Motor

The selection of the DNAzyme to construct the motor is of fundamental importance for accomplishing the intracellular motion of the motor. DNAzymes with high rate of catalytic cleavage, short catalytic core sequence, and editable arm sequences are preferred. The high rate of catalytic cleavage can allow the motor to have a fast walking speed. The short catalytic core provides options for the DNAzyme to have longer spacers that may be needed for the walking of the motor. The editable arms make it possible to truncate the arms of the DNAzyme for the motor construction. We compared features of three DNAzyme candidates, 10-23, 8-17 and 8-17E. The 10-23 and 8-17 DNAzymes require high concentrations (>50 mM) of $Mg^{2+}$ to achieve their optimal activity. It is challenging for cells to take up such high levels of $Mg^{2+}$ ion[51, 52]. We chose 8-17E, a variant of the 8-17 DNAzyme, to construct the DNAzyme motor, because previous work has shown that 8-17E DNAzyme could reach its best activity in the presence of 200 µM $Pb^{2+}$. We found that truncation of Arm 1 and Arm 2 of the original 8-17E DNAzyme from 9 nt to 5 nt and 7 nt alters the dependence of the DNAzyme on divalent metal ions. Instead of $Pb^{2+}$, $Mn^{2+}$ leads to the highest activity of this DNAzyme and the optimal concentration of $Mn^{2+}$ is 500 µM. This alteration is much more favorable for intracellular operation, because $Mn^{2+}$ is much less cytotoxic than $Pb^{2+}$ and cells can quickly and readily take up the amount of $Mn^{2+}$ required for the operation of the motor. We further compared the operation of DNAzyme motors constructed from the use of 10-23, 8-17, and 8-17E DNAzymes. Although the binding arms are the same for these three DNAzyme motors, in the presence of 500 µM $Mn^{2+}$, the motor constructed from 8-17E showed a significantly higher walking speed than the other two DNAzyme motors (FIG. 30).

Evaluation of the Operation of the DNAzyme Motor in Buffer

A DNA strand having the same sequence as miR-10b microRNA was used as the initial target to turn on the operation of the DNAzyme motor. The impact of key parameters on the operation of the DNAzyme motor was examined, including locking strands, cofactors, operating pH, and DNAzymes. Unless otherwise stated, 200 pM target sequence and 230 pM functionalized AuNPs were used to evaluate the operation of the DNAzyme motor in buffer. Ninety-five microliters of the operating solutions were prepared to contain 200 pM target sequence (or no target sequence in parallel experiments to serve as reagent blanks) and 230 pM functionalized AuNP in 25 mM Tris-acetate buffer and 200 mM NaCl. After incubation at room temperature for 20 min, a cofactor solution (5 µL) was added to initiate the operation of the motor. Fluorescence was measured at 515 nm in real-time for 60 min with excitation at 485 nm.

The response of the motor to varying concentrations of the target sequence was evaluated under the optimized conditions. Ninety-five microliters of the operating solutions were prepared to contain 230 pM functionalized AuNP and varying concentrations of the target sequence in 25 mM Tris-acetate buffer (8.0) and 200 mM NaCl. After incubation at room temperature for 20 min, 5 µL of 10 mM $MnCl_2$ solution was added to initiate the operation of the motor. The fluorescence of the solutions was then measured in real-time with excitation at 485 nm and emission at 515 nm.

Examination of Cellular Uptake of the Motor System

The cellular uptake of the DNAzyme motor system, consisting of AuNPs functionalized with substrate and locked DNAzyme sequences, was determined by using inductively coupled plasma mass spectrometry (ICP-MS) (FIG. 31). Cells were seeded onto an 18-mm round glass slide. When cultured to 80-90% confluence, cells were washed with 1×PBS three times. To the glass slide was added 100 µL of the uptake medium prepared by suspending different concentrations of the DNAzyme motor system into Opti-MEM Reduced Serum Medium (Fisher Scientific, Ottawa, ON). After incubation at room temperature for two, six, or eight hours to allow cells to take up the DNAzyme motor system, cells were thoroughly washed with 1×PBS six times. Cells were then detached by using 0.05% trypsin-EDTA and collected using centrifugation. The number of cells was counted by using a hemocytometer. Collected cells were lysed and digested with 10% ultrapure nitric acid at 60° C. overnight. The amount of AuNPs was measured by detecting Au at m/z 197 using ICP-MS (Agilent 7500 cs, Japan), against a calibration of acid-digested AuNP standards. The uptake number of AuNPs per cell was then derived from the total amount of AuNPs and cell number. Based on the results of cell imaging, the cell size of 20 μm diameter was used to estimate the intracellular AuNP concentrations.

Evaluation of Intracellular Operation of the DNAzyme Motor

All the cell lines were cultured in a humidified incubator at 37° C. containing 5% $CO_2$. The MCF10a cell line was obtained from the American Type Culture Collection (ATCC, Manassas, Va.) and was cultured in DMEM/F12 medium (Invitrogen Life Technologies, Carlsbad, Calif.) supplemented with 20 ng/ml EGF, 100 ng/ml cholera toxin, 500 ng/ml hydrocortisone, 2 mM L-glutamine, and 20 ng/ml gentamicin. The MCF-7 cell line was cultured in DMEM (Dulbecco's modified Eagle's medium), supplemented with 10% fetal bovine serum, penicillin and streptomycin, and 2.5 mM L-glutamine (GIBCO-Invitrogen, Carlsbad, Calif.).

Cells were seeded onto an 18-mm round glass slide. When cultured to 80-90% confluence, cells were washed with 1×PBS twice, and incubated with Opti-MEM reduced serum medium containing the DNAzyme motor (equivalent to 0.2 nM functionalized AuNP) for 2 h, to allow the cellular uptake of the DNAzyme motor. To remove the DNAzyme motor not taken up, cells were washed with 1×PBS three times and with 25 mM Tris-acetate buffer (pH 8.0) containing 125 mM NaCl another three times. Cells were treated with the 25 mM Tris-acetate buffer (pH 8.0) containing 125 mM NaCl and 5 mM $MnCl_2$ to allow the cellular uptake of $Mn^{2+}$. Fluorescence imaging of living cells was carried out on an Olympus IX-81 microscope that was coupled with a Yokagawa CSU×1 spinning disk confocal scan-head and Hamamatsu EMCCD cameras with 40×/1.3 Oil and 20×/0.85 Oil objective lenses. Two pumped diode lasers at 491 nm and 630 nm were used for the excitation of FAM and Cy5, respectively. The exposure time was set to be 180 ms for FAM and 100 ms for Cy5.

To test whether possible adsorption of the DNAzyme motor on the cell surface could produce fluorescence signals that would confound the detection of intracellular targets, we conducted the following control experiment (as schematically depicted in FIG. 32a-d). We first incubated MDA-MB-231 cancer cells with an inactive DNAzyme motor system constructed with the mutated DNAzyme. We then added 0.5 mM $Mn^{2+}$, incubated for 60 min, and obtained fluorescence images of the cells (FIG. 33a-d). No fluorescence signal was detected (FIG. 33b), which is as expected because the mutated DNAzyme is not able to cleave the substrate. After washing the cells 3 times with 1×PBS, we further incubated the cells with 200 pM free control DNAzyme sequence and then measured cellular fluorescence after incubation for additional 20 min. Because the free control DNAzyme has 8 nt in both Arm 1 and Arm 2 complementary to its substrate strand (Table 1), it can readily hybridize to and cleave the substrate strand. Therefore, if the DNAzyme motor system were adsorbed on the surface of the cells, the free control DNAzyme would hybridize to the substrate strands and cleave them off from the DNAzyme motor system, generating fluorescence signal. Our results showed no detectable fluorescence (FIG. 33c), ruling out possible interference from potential adsorption of the DNAzyme motor on the cell surface. As a confirmation that the mutant DNAzyme motor system entered the cells, we finally treated the cells with 2-mercaptoethanol to release all fluorescent substrate from the AuNPs of the mutant DNAzyme motor and monitored the fluorescence in the cells (FIG. 33d). The detectable fluorescence signals in the cells confirm the presence of the DNAzyme motor system. The fluorescence signals are due to the chemical cleavage of the Au—S linkage, releasing the fluorescent substrate from the AuNP. These results confirm that DNAzyme motors were taken up by the cells and that non-specific interaction of the DNAzyme motor system with the cells did not confound the detection of specific miRNA target.

To examine whether the target miRNA could leak out of the cells and then initiate operation of the DNAzyme motor outside of cells, we conducted the following control experiment. We added a DNAzyme reaction buffer, containing 25 mM Tris-acetate (pH 8.0) and 125 mM NaCl, to the MDA-MB-231 cells, and removed the buffer either 1 h after incubation with the cells or immediately after its contact with the cells (1 min). We then added 230 pM of the DNAzyme motor and 0.5 mM $MnCl_2$ to these reaction buffer solutions and monitored fluorescence (the operation of the DNAzyme motor) for 60 min (FIG. 34). If the target miRNA were leaked out of the cells, they would initiate operation of the DNAzyme motor and generate fluorescence signals. However, there was no detectable fluorescence increase (FIG. 34), suggesting that leaking of the target miRNA from the cells into the reaction buffer was negligible. As a positive control, further addition of 200 pM target miRNA to the solution resulted in an expected fluorescence increase (FIG. 34).

TABLE 3

Oligonucleotide sequences used to construct the DNAzyme motor for tracing the operation of the DNAzyme motor on individual AuNPs.

| Oligonucleotides | Sequences (5'→3') | SEQ ID NO: |
|---|---|---|
| Signal reporter | Cy5-TCT GTG ACG TAC CTT CTC TGA TCA TCC TGT TT-HS | 21 |
| Substrate strand | ACAGGATGATCAGAGAAGGTACGTCACAGA TCTCACTATrAGGAAGAGAT-/5IAbRQ/ | 22 |
| Lock-6 | AAGAGACACAAATTCGGTTCTACAGGGTA | 23 |

TABLE 3-continued

Oligonucleotide sequences used to construct the DNAzyme motor for tracing the operation of the DNAzyme motor on individual AuNPs.

| Oligonucleotides | Sequences (5'→3') | SEQ ID NO: |
|---|---|---|
| DNAzyme strand | HS-(T)$_{43}$AGAACCGAATTTGTG<u>TCTCTTC</u>TCCGAGCCGGTCGAAATAGT<br>Arm1 Catalytic core Arm2 | 24 |
| Target microRNA-10b | UACCCUGUAGAACCGAAUUUGUG | 25 |
| Target DNA | TACCCTGTAGAACCGAATTTGTG | 26 |
| Locking Strand | AAGAGACACAAATTCGGTTCTACAGGGTA-Cy5 | 27 |
| Cleaved substrate strand 1 (F1) | GGAAGAGAT-6-Carboxyfluorescein (FAM) | 28 |
| Cleaved substrate strand 2 (F2) | HS-TTTTTTTTTTTTTCACTATrA | 29 |

REFERENCES

1. Hirokawa N, Noda Y, Tanaka Y, Niwa S. Kinesin superfamily motor proteins and intracellular transport. *Nat Rev Mol Cell Bio* 10, 682-696 (2009).
2. Hancock W O. Bidirectional cargo transport: moving beyond tug of war. *Nat Rev Mol Cell Bio* 15, 615-628 (2014).
3. Vale R D. The molecular motor toolbox for intracellular transport. *Cell* 112, 467-480 (2003).
4. Buxbaum A R, Haimovich G, Singer R H. In the right place at the right time: visualizing and understanding mRNA localization. *Nat Rev Mol Cell Bio* 16, 95-109 (2015).
5. Yildiz A, Tomishige M, Vale R D, Selvin P R. Kinesin walks hand-over-hand. *Science* 303, 676-678 (2004).
6. Rock R S, Rice S E, Wells A L, Purcell T J, Spudich J A, Sweeney H L. Myosin V I is a processive motor with a large step size. *Proc Natl Acad Sci USA* 98, 13655-13659 (2001).
7. Yehl K, et al. High-speed DNA-based rolling motors powered by RNase H. *Nat Nanotechnol* 11, 184-190 (2016).
8. Jung C, Allen P B, Ellington A D. A stochastic DNA walker that traverses a microparticle surface. *Nat Nanotechnol* 11, 157-163 (2016).
9. Zhou C, Duan X Y, Liu N. A plasmonic nanorod that walks on DNA origami. *Nat Commun* 6, doi:10.1038/ncomms9102 (2015).
10. Cha T G, et al. Design principles of DNA enzyme-based walkers: translocation kinetics and photoregulation. *J Am Chem Soc* 137, 9429-9437 (2015).
11. Wickham S F J, et al. A DNA-based molecular motor that can navigate a network of tracks. *Nat Nanotechnol* 7, 169-173 (2012).
12. Pan J, Li F R, Cha T G, Chen H R, Choi J H. Recent progress on DNA based walkers. *Curr Opin Biotech* 34, 56-64 (2015).
13. Bath J, Green S J, Turberfield A J. A free-running DNA motor powered by a nicking enzyme. *Angew Chem Int Edit* 44, 4358-4361 (2005).
14. Yin P, Yan H, Daniell X G, Turberfield A J, Reif J H. A unidirectional DNA walker that moves autonomously along a track. *Angew Chem Int Edit* 43, 4906-4911 (2004).
15. Zhang D Y, Seelig G. Dynamic DNA nanotechnology using strand-displacement reactions. *Nat Chem* 3, 103-113 (2011).
16. Zhang F, Nangreave J, Liu Y, Yan H. Structural DNA nanotechnology: state of the art and future perspective. *J Am Chem Soc* 136, 11198-11211 (2014).
17. Yurke B, Turberfield A J, Mills A P, Simmel F C, Neumann J L. A DNA-fueled molecular machine made of DNA. *Nature* 406, 605-608 (2000).
18. Venkataraman S, Dirks R M, Rothemund P W K, Winfree E, Pierce N A. An autonomous polymerization motor powered by DNA hybridization. *Nat Nanotechnol* 2, 490-494 (2007).
19. Chen Y, Wang M S, Mao C D. An autonomous DNA nanomotor powered by a DNA enzyme. *Angew Chem Int Edit* 43, 3554-3557 (2004).
20. You M X, et al. An autonomous and controllable light-driven DNA walking device. *Angew Chem Int Edit* 51, 2457-2460 (2012).
21. He Y, Liu D R. Autonomous multistep organic synthesis in a single isothermal solution mediated by a DNA walker. *Nat Nanotechnol* 5, 778-782 (2010).
22. Wang Z G, Elbaz J, Willner I. DNA machines: bipedal walker and stepper. *Nano Lett* 11, 304-309 (2011).
23. Tian Y, He Y, Chen Y, Yin P, Mao C D. Molecular devices—A DNAzyme that walks processively and autonomously along a one-dimensional track. *Angew Chem Int Edit* 44, 4355-4358 (2005).
24. Sherman W B, Seeman N C. A precisely controlled DNA biped walking device. *Nano Lett* 4, 1203-1207 (2004).
25. Shin J S, Pierce N A. A synthetic DNA walker for molecular transport. *J Am Chem Soc* 126, 10834-10835 (2004).
26. Wickham S F J, et al. Direct observation of stepwise movement of a synthetic molecular transporter. *Nat Nanotechnol* 6, 166-169 (2011).
27. Lund K, et al. Molecular robots guided by prescriptive landscapes. *Nature* 465, 206-210 (2010).
28. Gu H Z, Chao J, Xiao S J, Seeman N C. A proximity-based programmable DNA nanoscale assembly line. *Nature* 465, 202-205 (2010).
29. Cha T G, et al. A synthetic DNA motor that transports nanoparticles along carbon nanotubes. *Nat Nanotechnol* 9, 39-43 (2014).

30. Zhang H Q, Lai M D, Zuehlke A, Peng H Y, Li X F, Le X C. Binding-induced DNA nanomachines triggered by proteins and nucleic acids. *Angew Chem Int Edit* 54, 14326-14330 (2015).
31. Yang X L, Tang Y A, Mason S D, Chen J B, Li F. Enzyme-Powered Three-dimensional DNA nanomachine for DNA walking, payload release, and biosensing. *ACS Nano* 10, 2324-2330 (2016).
32. Muscat R A, Bath J, Turberfield A J. A programmable molecular robot. *Nano Lett* 11, 982-987 (2011).
33. Chen Y J, Groves B, Muscat R A, Seelig G. DNA nanotechnology from the test tube to the cell. *Nat Nanotechnol* 10, 748-760 (2015).
34. Bath J, Turberfield A J. DNA nanomachines. *Nat Nanotechnol* 2, 275-284 (2007).
35. Cha T G, et al. Optical nanosensor architecture for cell-signaling molecules using DNA aptamer-coated carbon nanotubes. *ACS Nano* 5, 4236-4244 (2011).
36. Brown A K, Li J, Pavot C M B, Lu Y. A lead-dependent DNAzyme with a two-step mechanism. *Biochemistry-US* 42, 7152-7161 (2003).
37. Zhou W H, Chen Q Y, Huang P J J, Ding J S, Liu J W. DNAzyme hybridization, cleavage, degradation, and sensing in undiluted human blood serum. *Anal Chem* 87, 4001-4007 (2015).
38. Cepeda-Plaza M, Null E L, Lu Y. Metal ion as both a cofactor and a probe of metal-binding sites in a uranyl-specific DNAzyme: a uranyl photocleavage study. *Nucleic Acids Res* 41, 9361-9370 (2013).
39. Nofiele J T, Czarnota G J, Cheng H L M. Noninvasive manganese-enhanced magnetic resonance imaging for early detection of breast cancer metastatic potential. *Mol Imaging* 13, doi: 10.2310/7290.2013.00071 (2014).
40. Zhang D Y, Chen S X, Yin P. Optimizing the specificity of nucleic acid hybridization. *Nat Chem* 4, 208-214 (2012).
41. Ma L, Teruya-Feldstein J, Weinberg R A. Tumour invasion and metastasis initiated by microRNA 10b in breast cancer. *Nature* 449, 682-688 (2007).
42. M'hamed I F, Privat M, Ponelle F, Penault-Llorca F, Kenani A, Bignon Y J. Identification of miR-10b, miR-26a, miR-146a and miR-153 as potential triple-negative breast cancer biomarkers. *Cell Oncol* 38, 433-442 (2015).
43. Tang J, Ahmad A, Sarkar F H. The Role of microRNAs in breast cancer migration, invasion and metastasis. *Int J Mol Sci* 13, 13414-13437 (2012).
44. Seferos D S, Giljohann D A, Hill H D, Prigodich A E, Mirkin C A. Nano-flares: probes for transfection and mRNA detection in living cells. *J Am Chem Soc* 129, 15477-15479 (2007).
45. Hwang K, et al. Photocaged DNAzymes as a general method for sensing metal ions in living cells. *Angew Chem Int Edit* 53, 13798-13802 (2014).
46. Giljohann D A, Seferos D S, Patel P C, Millstone J E, Rosi N L, Mirkin C A. Oligonucleotide loading determines cellular uptake of DNA-modified gold nanoparticles. *Nano Lett* 7, 3818-3821 (2007).
47. Dykman L A, Khlebtsov N G. Uptake of engineered gold nanoparticles into mammalian cells. *Chem Rev* 114, 1258-1288 (2014).
48. Lim Z Z J, Li J E J, Ng C T, Yung L Y L, Bay B H. Gold nanoparticles in cancer therapy. *Acta Pharmacol Sin* 32, 983-990 (2011).
49. Kim C, Agasti S S, Zhu Z J, Isaacs L, Rotello V M. Recognition-mediated activation of therapeutic gold nanoparticles inside living cells. *Nat Chem* 2, 962-966 (2010).
50. Santoro S W, Joyce G F. Mechanism and utility of an RNA-cleaving DNA enzyme. *Biochemistry-US* 37, 13330-13342 (1998).
51. Wolf F I, Trapani V. Cell (patho) physiology of magnesium. *Clin Sci* 114, 27-35 (2008).
52. Maguire M E, Cowan J A. Magnesium chemistry and biochemistry. *Biometals* 15, 203-210 (2002).

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A nanomotor system, comprising:
a support, wherein said support is nanoparticle gold;
a substrate strand comprising a first end conjugated to said support; a second end, said second end comprising a first label; and a substrate portion positioned between said first end and said second end, wherein said first label is a fluorophore;
a motor strand comprising a first end conjugated to the support; a second end; and a catalytic core positioned between said first end and said second end; said catalytic core is switchable between an active state and an inactive state, in said active state said catalytic core is operable to cleave said substrate portion of said substrate strand; and
a locking strand comprising a first end; a second end; and a locking region positioned between said first end and said second end, said locking region adapted to removably bind to said motor strand, said locking strand optionally comprising a label and/or a moiety at said first end or said second end,
wherein when said locking strand binds to said motor strand, said catalytic core is in the inactive state,
wherein when said locking strand is absent or is displaced from said motor strand by a target, said catalytic core is in the active state
wherein said substrate strand comprises a nucleotide sequence,
wherein when the motor strand cleaves a substrate strand, it is released from the substrate strand and can interact with and cleave additional substrate strands on the same support in succession.

2. The nanomotor system of claim 1 wherein said substrate strand comprises a DNA:RNA chimeric sequence.

3. The nanomotor system of claim 1, wherein the first end of said substrate strand comprises a spacer, wherein said spacer is conjugated to said support.

4. The nanomotor of claim 1, wherein the substrate strand can be hybridized to a quencher-containing and hairpin-forming further strand.

5. The nanomotor system of claim 1, wherein said catalytic core comprises a DNAzyme.

6. The nanomotor system of claim 1, wherein said first end of said motor strand comprises a spacer, wherein said spacer is conjugated to said support.

7. The nanomotor system of claim 1, wherein said motor strand comprises a locking region adjacent said spacer, said locking region comprising a first domain (T*1) and a first arm (Arm2); and a second arm (Arm1), said catalytic core positioned between said first arm and said second arm.

8. The nanomotor system of claim 1, wherein said locking region on said locking strand comprises a target binding domain and a sequestering domain, wherein said target binding domain comprises a sequence which removably binds to said target, wherein said sequestering domain comprises a sequence which removably binds to said first arm of said motor strand.

9. The nanomotor system of claim 8, wherein said locking region on said locking strand comprises a target binding domain and a sequestering domain, wherein said target binding domain comprises a sequence which is complementary to said target, wherein said sequestering domain comprises a sequence complementary to said first arm of said motor strand.

10. The nanomotor system of claim 8, wherein said target is a small molecule, a protein, nucleic acid, a metabolite, an amino acid, a herbicide, a pesticide, an environmental pollutant, an antigen, a receptor, a receptor ligand, a peptide, a polysaccharide, a lipopolysaccharide, a lipid, a fatty acid, a vitamin, a pharmaceutical compound, a hormone, a growth factor, an enzyme, a coenzyme, an apoenzyme, haptens, lechtins, or a cellular component or organelle.

11. A nanomotor system, comprising:
a support, wherein said support is nanoparticle gold;
a substrate strand comprising a first end conjugated to said support; a second end, said second end comprising a first label; and a substrate portion positioned between said first end and said second end, wherein said first label is a fluorophore;
a motor strand comprising a first end conjugated to the support; a second end; and a catalytic core positioned between said first end and said second end; said catalytic core is switchable between an active state and an inactive state, in said active state said catalytic core is operable to cleave said substrate portion of said substrate strand; and
a locking strand comprising a first end; a second end; and a locking region positioned between said first end and said second end, said locking region adapted to removably bind to said motor strand, said locking strand is not covalently bound to said motor strand said locking strand optionally comprising a label and/or a moiety at said first end or said second end,
wherein when said locking strand binds to said motor strand, said catalytic core is in the inactive state,
wherein when said locking strand is absent or is displaced from said motor strand by a target, said catalytic core is in the active state
wherein said substrate strand comprises a nucleotide sequence,
wherein when the motor strand cleaves a substrate strand, it is released from the substrate strand and can interact with and cleave additional substrate strands on the same support in succession.

12. The nanomotor system of claim 11, wherein said substrate strand comprises a DNA:RNA chimeric sequence.

13. The nanomotor system of claim 11, wherein the first end of said substrate strand comprises a spacer, wherein said spacer is conjugated to said support.

14. The nanomotor of claim 11, wherein the substrate strand can be hybridized to a quencher-containing and hairpin-forming further strand.

15. The nanomotor system of claim 11, wherein said catalytic core comprises a DNAzyme.

16. The nanomotor system of claim 11, wherein said first end of said motor strand comprises a spacer, wherein said spacer is conjugated to said support.

17. The nanomotor system of claim 11, wherein said motor strand comprises a locking region adjacent said spacer, said locking region comprising a first domain (T*1) and a first arm (Arm2); and a second arm (Arm1), said catalytic core positioned between said first arm and said second arm.

18. The nanomotor system of claim 11, wherein said locking region on said locking strand comprises a target binding domain and a sequestering domain, wherein said target binding domain comprises a sequence which removably binds to said target, wherein said sequestering domain comprises a sequence which removably binds to said first arm of said motor strand.

19. The nanomotor system of claim 17, wherein said locking region on said locking strand comprises a target binding domain and a sequestering domain, wherein said target binding domain comprises a sequence which is complementary to said target, wherein said sequestering domain comprises a sequence complementary to said first arm of said motor strand.

20. The nanomotor system of claim 17, wherein said target is a small molecule, a protein, nucleic acid, a metabolite, an amino acid, a herbicide, a pesticide, an environmental pollutant, an antigen, a receptor, a receptor ligand, a peptide, a polysaccharide, a lipopolysaccharide, a lipid, a fatty acid, a vitamin, a pharmaceutical compound, a hormone, a growth factor, an enzyme, a coenzyme, an apoenzyme, haptens, lechtins, or a cellular component or organelle.

\* \* \* \* \*

SEQUENCE LISTING

```
<160> NUMBER OF SEQ ID NOS: 29

<210> SEQ ID NO 1
<211> LENGTH: 33
<212> TYPE: DNA
<213> ORGANISM: Artificial Sequence
<220> FEATURE:
<223> OTHER INFORMATION: substrate strand
<220> FEATURE:
<221> NAME/KEY: 6-Carboxyfluorescein
<222> LOCATION: (33)..(33)

<400> SEQUENCE: 1
hstttttttt tttttcact atraggaaga gat                              33

<210> SEQ ID NO 2
```

```
<211> LENGTH: 27
<212> TYPE: DNA
<213> ORGANISM: Artificial Sequence
<220> FEATURE:
<223> OTHER INFORMATION: Lock -4

<400> SEQUENCE: 2
gagacacaaa ttcggttcta cagggta                                          27

<210> SEQ ID NO 3
<211> LENGTH: 28
<212> TYPE: DNA
<213> ORGANISM: artificial sequence
<220> FEATURE:
<223> OTHER INFORMATION: Lock -5

<400> SEQUENCE: 3
agagacacaa attcggttct acagggta                                         28

<210> SEQ ID NO 4
<211> LENGTH: 29
<212> TYPE: DNA
<213> ORGANISM: artificial sequence
<220> FEATURE:
<223> OTHER INFORMATION: Lock -6
<220> FEATURE:
<221> NAME/KEY: Cy5
<222> LOCATION: (29)..(29)

<400> SEQUENCE: 4
aagagacaca aattcggttc tacagggta                                        29

<210> SEQ ID NO 5
<211> LENGTH: 30
<212> TYPE: DNA
<213> ORGANISM: artificial sequence
<220> FEATURE:
<223> OTHER INFORMATION: Lock -7

<400> SEQUENCE: 5 gaaagagacac aaattcggtt ctacagggta                                      30

<210> SEQ ID NO 6
<211> LENGTH: 31
<212> TYPE: DNA
<213> ORGANISM: Artificial Sequence
<220> FEATURE:
<223> OTHER INFORMATION: Free Control DNAzyme

<400> SEQUENCE: 6
atctcttctc cgagccggtc gaaatagtga a                                     31

<210> SEQ ID NO 7
<211> LENGTH: 87
<212> TYPE: DNA
<213> ORGANISM: Artificial Sequence
<220> FEATURE:
<223> OTHER INFORMATION: DNAzyme strand linked to AuNP

<400> SEQUENCE: 7 hsttttttt tttttttttt tttttttttt tttttttttt ttttagaac cgaatttgtg        60 tctcttctcc gagccggtcg aaatagt                                          87

<210> SEQ ID NO 8
<211> LENGTH: 87
<212> TYPE: DNA
```

```
<213> ORGANISM: artificial sequence
<220> FEATURE:
<223> OTHER INFORMATION: Mutant DNAzyme strand linked to AuNP

<400> SEQUENCE: 8
hstttttttt tttttttttt tttttttttt tttttttttt ttttagaac cgaatttgtg        60 tctcttctcc gatccggtct aaatagt                                           87

<210> SEQ ID NO 9
<211> LENGTH: 23
<212> TYPE: RNA
<213> ORGANISM: artificial sequence
<220> FEATURE:
<223> OTHER INFORMATION: Target microRNA-10b

<400> SEQUENCE: 9
uacccuguag aaccgaauuu gug                                               23

<210> SEQ ID NO 10
<211> LENGTH: 23
<212> TYPE: DNA
<213> ORGANISM: artificial sequence
<220> FEATURE:
<223> OTHER INFORMATION: DNA Target

<400> SEQUENCE: 10
taccctgtag aaccgaattt gtg                                               23

<210> SEQ ID NO 11
<211> LENGTH: 23
<212> TYPE: DNA
<213> ORGANISM: artificial sequence
<220> FEATURE:
<223> OTHER INFORMATION: Mismatch-1

<400> SEQUENCE: 11
tacactgtag aaccgaattt gtg                                               23

<210> SEQ ID NO 12
<211> LENGTH: 23
<212> TYPE: DNA
<213> ORGANISM: artificial sequence
<220> FEATURE:
<223> OTHER INFORMATION: Mismatch-2

<400> SEQUENCE: 12
taccatgtag aaccgaattt gtg                                               23

<210> SEQ ID NO 13
<211> LENGTH: 23
<212> TYPE: DNA
<213> ORGANISM: artificial sequence
<220> FEATURE:
<223> OTHER INFORMATION: Mismatch-3

<400> SEQUENCE: 13
taccctgtag aagcgaattt gtg                                               23

<210> SEQ ID NO 14
<211> LENGTH: 23
<212> TYPE: DNA
<213> ORGANISM: artificial sequence
<220> FEATURE:
<223> OTHER INFORMATION: Mismatch-4

<400> SEQUENCE: 14
```

```
tacccctgtag aacctaattt gtg                                           23
```

<210> SEQ ID NO 15
<211> LENGTH: 23
<212> TYPE: DNA
<213> ORGANISM: artificial sequence
<220> FEATURE:
<223> OTHER INFORMATION: Mismatch-5

<400> SEQUENCE: 15

```
tacccctgtag aaccgaattt ttg                                           23
```

<210> SEQ ID NO 16
<211> LENGTH: 74
<212> TYPE: DNA
<213> ORGANISM: artificial sequence
<220> FEATURE:
<223> OTHER INFORMATION: Biotin-DNAzyme 8-17E
<220> FEATURE:
<221> NAME/KEY: Biotin
<222> LOCATION: (1)..(1)

<400> SEQUENCE: 16

```
tttttttttt tttttttttt tttttttttt tttttttttt ttttttgtct cttctccgag    60
ccggtcgaaa tagt                                                      74
```

<210> SEQ ID NO 17
<211> LENGTH: 73
<212> TYPE: DNA
<213> ORGANISM: artificial sequence
<220> FEATURE:
<223> OTHER INFORMATION: Biotin-DNAzyme 8-17
<220> FEATURE:
<221> NAME/KEY: Biotin
<222> LOCATION: (1)..(1)

<400> SEQUENCE: 17

```
tttttttttt tttttttttt tttttttttt tttttttttt ttttttgtct cttctccgag    60
ccggacgaat agt                                                       73
```

<210> SEQ ID NO 18
<211> LENGTH: 74
<212> TYPE: DNA
<213> ORGANISM: artificial sequence
<220> FEATURE:
<223> OTHER INFORMATION: Biotin-DNAzyme 10-23
<220> FEATURE:
<221> NAME/KEY: Biotin
<222> LOCATION: (1)..(1)

<400> SEQUENCE: 18

```
tttttttttt tttttttttt tttttttttt tttttttttt tttttttct cttcaggcta     60 gctacaacga tagt                                                      74
```

<210> SEQ ID NO 19
<211> LENGTH: 32
<212> TYPE: DNA
<213> ORGANISM: artificial sequence
<220> FEATURE:
<223> OTHER INFORMATION: Poly(T)-biotin
<220> FEATURE:
<221> NAME/KEY: Biotin
<222> LOCATION: (32)..(32)

<400> SEQUENCE: 19

```
hstttttttt tttttttttt tttttttttt tt                              32
```

<210> SEQ ID NO 20
<211> LENGTH: 33
<212> TYPE: DNA
<213> ORGANISM: artificial sequence
<220> FEATURE:
<223> OTHER INFORMATION: Substrate strand for DNAzyme 10-23
<220> FEATURE:
<221> NAME/KEY: FAM
<222> LOCATION: (32)..(32)

<400> SEQUENCE: 20

```
hstttttttt tttttttacta trgrugaaga gat                            33
```

<210> SEQ ID NO 21
<211> LENGTH: 34
<212> TYPE: DNA
<213> ORGANISM: artificial sequence
<220> FEATURE:
<223> OTHER INFORMATION: Signal reporter
<220> FEATURE:
<221> NAME/KEY: Cy5
<222> LOCATION: (1)..(1)

<400> SEQUENCE: 21

```
tctgtgacgt accttctctg atcatcctgt tths                            34
```

<210> SEQ ID NO 22
<211> LENGTH: 50
<212> TYPE: DNA
<213> ORGANISM: artificial sequence
<220> FEATURE:
<223> OTHER INFORMATION: Substrate strand
<220> FEATURE:
<221> NAME/KEY: 5IAbRQ
<222> LOCATION: (50)..(50)

<400> SEQUENCE: 22

```
acaggatgat cagagaaggt acgtcacaga tctcactatr aggaagagat            50
```

<210> SEQ ID NO 23
<211> LENGTH: 29
<212> TYPE: DNA
<213> ORGANISM: artificial sequence
<220> FEATURE:
<223> OTHER INFORMATION: Lock-6

<400> SEQUENCE: 23

```
aagagacaca aattcggttc tacagggta                                  29
```

<210> SEQ ID NO 24
<211> LENGTH: 87
<212> TYPE: DNA
<213> ORGANISM: artificial sequence
<220> FEATURE:
<223> OTHER INFORMATION: DNAzyme strand

<400> SEQUENCE: 24

```
hstttttttt tttttttttt tttttttttt tttttttttt ttttagaac cgaatttgtg  60 tctcttctcc gagccggtcg aaatagt                                    87
```

<210> SEQ ID NO 25
<211> LENGTH: 23
<212> TYPE: RNA
<213> ORGANISM: artificial sequence
<220> FEATURE:

<223> OTHER INFORMATION: Target microRNA-10b #2

<400> SEQUENCE: 25
uacccuguag aaccgaauuu gug                                          23

<210> SEQ ID NO 26
<211> LENGTH: 23
<212> TYPE: DNA
<213> ORGANISM: artificial sequence
<220> FEATURE:
<223> OTHER INFORMATION: Target DNA

<400> SEQUENCE: 26
taccctgtag aaccgaattt gtg                                          23

<210> SEQ ID NO 27
<211> LENGTH: 29
<212> TYPE: DNA
<213> ORGANISM: Artificial Sequence
<220> FEATURE:
<223> OTHER INFORMATION: Locking Strang
<220> FEATURE:
<221> NAME/KEY: Cy5
<222> LOCATION: (29)..(29)

<400> SEQUENCE: 27
aagagacaca aattcggttc tacagggta                                    29

<210> SEQ ID NO 28
<211> LENGTH: 9
<212> TYPE: DNA
<213> ORGANISM: Artificial Sequence
<220> FEATURE:
<223> OTHER INFORMATION: Cleaved substrate strand 1 (F1)
<220> FEATURE:
<221> NAME/KEY: FAM
<222> LOCATION: (9)..(9)

<400> SEQUENCE: 28 ggaagagat                                                           9

<210> SEQ ID NO 29
<211> LENGTH: 24
<212> TYPE: DNA
<213> ORGANISM: Artificial Sequence
<220> FEATURE:
<223> OTHER INFORMATION: Cleaved substrate strand 2 (F2)

<400> SEQUENCE: 29
hstttttttt tttttttcact atra                                        24